(12) United States Patent
Ortac

(10) Patent No.: US 12,006,535 B2
(45) Date of Patent: Jun. 11, 2024

(54) METHODS AND DEVICES FOR DETECTING SARS-COV-2

(71) Applicant: Sarmal, Inc., San Diego, CA (US)

(72) Inventor: Inanc Ortac, San Diego, CA (US)

(73) Assignee: SARMAL, INC., San Diego, CA (US)

(*) Notice: Subject to any disclaimer, the term of this patent is extended or adjusted under 35 U.S.C. 154(b) by 0 days.

(21) Appl. No.: 16/888,368

(22) Filed: May 29, 2020

(65) Prior Publication Data

US 2021/0147907 A1 May 20, 2021

Related U.S. Application Data

(60) Provisional application No. 63/022,262, filed on May 8, 2020, provisional application No. 62/937,634, filed on Nov. 19, 2019.

(51) Int. Cl.
*C12Q 1/686* (2018.01)
*C12Q 1/6818* (2018.01)
*G01N 21/66* (2006.01)

(52) U.S. Cl.
CPC ............ *C12Q 1/686* (2013.01); *C12Q 1/6818* (2013.01); *G01N 21/66* (2013.01); *C12Q 2565/301* (2013.01)

(58) Field of Classification Search
CPC .......... C12Q 1/686; C12Q 1/6818; C12Q 2565/301; C12Q 1/701; C12Q 1/6806; C12Q 1/6844; C12Q 2523/307; C12Q 2527/119; C12Q 2527/146; C12Q 2565/519; C12Q 2563/103; G01N 21/66
See application file for complete search history.

(56) References Cited

U.S. PATENT DOCUMENTS

| | | | |
|---|---|---|---|
| 6,017,696 A | 1/2000 | Heller | |
| 6,029,518 A | 2/2000 | Oeftering | |
| 6,242,246 B1* | 6/2001 | Gold | C12Q 1/6837 435/287.1 |
| 6,289,144 B1 | 9/2001 | Neuschafer et al. | |
| 6,917,726 B2 | 7/2005 | Levene et al. | |
| 7,141,370 B2 | 11/2006 | Hassibi et al. | |
| 7,217,542 B2* | 5/2007 | Tyvoll | B01L 3/502715 435/6.11 |
| 7,405,281 B2 | 7/2008 | Xu et al. | |
| 7,455,968 B2* | 11/2008 | Pfistershammer | C12Q 1/6827 435/6.11 |
| 7,714,303 B2 | 5/2010 | Lundquist et al. | |
| 7,763,423 B2 | 7/2010 | Roitman et al. | |
| 7,820,983 B2 | 10/2010 | Lundquist et al. | |
| 8,133,672 B2 | 3/2012 | Bjornson et al. | |
| 8,252,911 B2 | 8/2012 | Bjornson et al. | |
| 8,257,954 B2 | 9/2012 | Clark et al. | |
| 8,530,164 B2 | 9/2013 | Patel et al. | |
| 8,802,424 B2 | 8/2014 | Luong et al. | |
| 8,932,815 B2* | 1/2015 | Krishnan | C12N 15/101 435/6.1 |
| 9,127,259 B2 | 9/2015 | Bjornson et al. | |
| 9,410,171 B2* | 8/2016 | Ortac | C12Q 1/686 |
| 9,447,464 B2 | 9/2016 | Emig et al. | |
| 9,464,107 B2 | 10/2016 | Wegener et al. | |
| 2002/0076825 A1 | 6/2002 | Cheng et al. | |
| 2012/0329042 A1 | 12/2012 | Beechem et al. | |
| 2013/0344539 A1* | 12/2013 | Ortac | B01L 3/50273 435/91.2 |
| 2015/0050657 A1* | 2/2015 | Rigatti | C12Q 2563/155 435/6.12 |
| 2016/0186237 A1* | 6/2016 | Makrigiorgos | C12Q 1/686 506/9 |
| 2019/0137434 A1 | 5/2019 | Seker et al. | |

FOREIGN PATENT DOCUMENTS

| | | |
|---|---|---|
| WO | 2004076683 A2 | 9/2004 |
| WO | 2007075987 A3 | 7/2007 |
| WO | 2007076057 A2 | 7/2007 |
| WO | 2016160131 A1 | 10/2016 |
| WO | 2019178302 A1 | 9/2019 |

OTHER PUBLICATIONS

Goda et al. Label-Free Potentiometry for Detecting DNA Hybridization Using Peptide Nucleic Acid and DNA Probes. Sensors; 2013; 13: 2267-2278. (Year: 2013).*
Goda et al. Sensors; 2013; 13: 2267-2278. (Year: 2013).*
Fontes et al. Biochemical and Biophysical Research Communications; 1997; 237: 445-450. (Year: 1997).*
Fontes et al. Synthesis of Dehydroluciferin by Firefly Luciferase: Effect of Dehydroluciferin, Coenzyme A and Nucleoside Triphosphates on the Luminescent Reaction. Biochemical and Biophysical Research Communications; 1997; 237: 445-450. Article No. RC977161. (Year: 1997).*
Xpert® Xpress SARS-CoV-2, Instructions for use, GeneXpert, Cepheid Innovation, 302-3562, Rev A Mar. 2020:p. 1-22. (Year: 2020).*
Debin Ji et al., ATP-releasing Nucleotides: Linking DNA Synthesis to Luciferase Signaling, Angew Chem Int Ed Engl, Feb. 5, 2016, 55(6): 2087-2091, Stanford University, Stanford.
Edman et al., Electric field directed nucleic and hybridization and microchips. Nucleic Acids Research, Dec. 1, 1997, vol. 25, No. 24, pp. 4907-4914; abstract, p. 4908, col. 2, para 1, Figs, 7-8.
International Search Report and Written Opinion for PCT/US20/61397 dated Apr. 7, 2021, 23 pages.
Russell et al., Gold Nanowire Based Electrical DNA Detection Using Rolling Circle Amplification; Department of Immunology, dated Jan. 16, 2014.
Dodeigne et al., Chemiluminescence as diagnostic tool. A review; Talanta 51 (2000) 415-439.
Marras et al., Selection of Fluorophore and Quencher Pairs for Fluorescent Nucleic Acid Hybridization Probes; Public Health Research Institute, 2006.
Cheng et al; Preparation and Hybridization Analysis of DNA/RNA from *E. coli* on Microfabricated Bioelectronic Chips; Nature Biotechnology, vol. 16, 1998, pp. 541-546.

(Continued)

*Primary Examiner* — Narayan K Bhat
(74) *Attorney, Agent, or Firm* — PROCOPIO, CORY, HARGREAVES & SAVITCH LLP

(57) ABSTRACT

Provided herein are methods and systems for detecting the presence of absence of a target-nucleic acid sequence, including SARS-COV2.

19 Claims, 20 Drawing Sheets
(5 of 20 Drawing Sheet(s) Filed in Color)

(56) References Cited

OTHER PUBLICATIONS

Burgers et al. (2001) "Eukaryotic DNA polymerases: proposal for a revised nomenclature" J Biol Chem. 276 (47):43487-90.
Hubscher et al. (2002) "Eukaryotic DNA Polymerases" Annual Review of Biochemistry vol. 71: 133-163; Alba (2001).
Johansson et al.; Replicative DNA Polymerases Department of Medical Biochemistry and Biophysics, 2013.
Steitz (1999) "DNA polymerases: structural diversity and common mechanisms" J Biol Chem 274:17395-17398.
Seidel, C.A.M., Schulz, A. and Sauer, M.M.H. (1996) Nucleobase-specific quenching of fluorescent dyes. 1. Nucleobase one-electron redox potentials and their correlation with static and dynamic quenching efficiencies. J. Phys. Chem. 100, 5541-5553.
Guo et al., Four-color DNA sequencing with 3'-O-modified nucleotide reversible terminators and chemically cleavable fluorescent dideoxynucleotides, Proc. Natl. Acad. Sci. U.S.A. (2008) 105:9145-9150.
Reimer et al, editors, Scanning Electron Microscopy: Physics of Image Formation and Microanalysis, 2nd Edition (Springer, 1998).
Dielectrophoretic Manipulation of Particles by Wang et al., in IEEE Transaction on Industry Applications, vol. 33, No. 3, May/Jun. 1997, pp. 660-669.

\* cited by examiner

METHODS AND DEVICES FOR DETECTING SARS-COV-2

CROSS-REFERENCE TO RELATED APPLICATIONS

This application claims priority under 35 U.S.C. 119(e) to U.S. Provisional Patent Application No. 62/937,634, filed Nov. 19, 2019, U.S. Provisional Patent Application No. 63/022,262, filed May 8, 2020, the disclosures of which are hereby incorporated herein by reference in their entirety as if set forth in full.

TECHNICAL FIELD

The invention relates to methods of detecting the presence or absence of target-nucleic acid sequences.

INTRODUCTION

Polymerase chain reaction can be used to increase the number of the copies of a particular DNA segment to detect the presence and/or quantify that segment or for further end uses such as increasing the amount of DNA.

For this it uses two oligonucleotide sequences corresponding to forward and reverse primers, that are addressed to the beginning and end of the sequence that one targets. Forward and reverse primers bind to the complementary strands of a double stranded DNA. Polymerase chain reaction utilizes temperature to generate hybridization and denaturation cycles between complementary strands and primer oligonucleotides as well as turning the polymerase enzyme activity on and off.

In PCR there is a repeating loop of a specific sequence of temperature levels (also referred to as thermal cycling). The typical PCR reaction goes through 30-40 cycles. During the PCR process many copies of the starting template DNA sequence defined by reverse and forward primers are generated. If the primers bind to a template sequence they amplify (make many copies) of the section of nucleic acid the primers border. A DNA binding dye that is sensitive to the double stranded DNA is utilized to recognize successful amplification; or a probe that is initially quenched, e.g., taqman, fluoresces in the presence of a particular sequence on the DNA. The product of PCR is confirmed by running a gel or using an intercalating fluorescence dye, in which case, the fluorescence intensity is correlated with the amount of the amplified sequence.

For most of the PCR applications, ending up with many copies of a DNA segment is actually not needed. PCR is performed just for the presence or the quantification of initial copy number of the segment as in quantitative PCR (qPCR). However, such PCR amplification causes additional limitations. For example, high specificity of the amplification cannot be achieved in most cases. In qPCR, use of DNA intercalating dyes can only detect the presence of double stranded DNA. Furthermore in many cases, primer pairs act as templates for each other amplifying unwanted byproducts. To prevent these non-specific artifacts, methods have been developed such as Taqman probes. This method requires the design of an additional probe complementary to a specific region of the generated sequence with a fluorophore attached to one side and a quencher attached to the other side adding another level of complexity to the overall reaction. Taqman or similar methods are specific to the generated sequence, but have different requirements in terms of the actual target sequence and length of the sequence increasing the complexity.

Most viral infections, such as the coronavirus, do not presently have a cure or vaccine. Early and effective testing is crucial to fighting these viral pandemics. The World Health Organization recommends a combination of measures: rapid diagnosis and immediate isolation of cases, rigorous tracking and precautionary self-isolation for individuals who have been in close contact. Exhaustive screening allows for early diagnosis which can be used to effectively isolate infected individuals and help prevent the spread of the virus. With highly contagious viral infections, a lack of adequate testing allows for rapid viral spread and hospitalization of people expressing symptoms, resulting in significant human and economic loss.

Accordingly, there is a need for improved methods for detecting nucleic acids at the point of care of the individuals being tested.

SUMMARY

Provided herein are methods for detecting and/or quantifying the presence of a nucleic acid sequence in a sample comprising:

providing an elongation mixture comprising (i) a polymerase enzyme, (ii) an ATP regenerating enzyme, (iii) a luminescence enzyme (e.g., firefly luciferase), (iv) a template nucleic acid from the sample, (v) a primer-probe that hybridizes to (e.g., that is complementary to) a particular target nucleic acid sequence, and (vi) a polymerase-ATP regenerating enzyme-luminescence reagent solution having the components for carrying out template directed elongation synthesis of a growing nucleic acid strand, wherein said reagent solution includes an ATP-regenerating-enzyme-substrate (e.g., with APS by ATP Sulfurylase; with ADP-glucose by AGPPase; with AMP+PEP by PPDK, and the like), a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;

carrying out nucleic acid elongation synthesis such that one or a plurality of nucleotide analogs are added sequentially to the template if the primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme (e.g., with APS by ATP Sulfurylase; with ADP-glucose by AGPPase; with AMP+PEP by PPDK, and the like) yielding ATP, then c) binding the ATP to a luminescence-enzyme, wherein a luminescence-substrate is catalyzed by the luminescence-enzyme to produce luminescence while regenerating the respective leaving group; and detecting light from the luminescence while nucleic acid synthesis is occurring, whereby detection of light indicates the presence of the particular target nucleic acid sequence. The emitted luminescence light can be detected by an appropriate optical sensor and/or detection device.

Target nucleic acid detection is achieved by detecting the luminescence generated each time a nucleotide is added to the complementary strand revealing the presence of the target by virtue of the binding of the interrogating primer-probe and initiation of the chain elongation reaction. If the target nucleic acid is not present, the primer-probe will not bind, chain elongation will not be initiated, and there will be no luminescence detected. Therefore, if the target nucleic acid is present, it will be bound by the primer-probe initiating chain elongation. In the embodiment referred to herein as the Luminescence Amplification By Continuous Elongation of DNA Strands (LACES) method, each specific nucleotide attachment will generate a luminescence (e.g., detectable light) signal that can be detected by an optical sensor/detector. As a result, detectable light signal is easily and rapidly produced, which can be detected in a suitable point of care (POC) device (FIG. 1).

The invention LACES method provided herein is used to detect the presence of, and the quantification of the copy number of, a target nucleic acid segment. It uses an interrogating primer (e.g., a primer-probe) oligonucleotide in the reaction mixture. When the primer-probe sequence hybridizes with the template sequence, a polymerase binds at the end of the double strand. As the elongation of complementary strand via polymerase occurs, pyrophosphate (PPi) is released as a leaving group. Using an enzyme system in accordance with the present invention (ATP Sulfurylase, PPDK, AGPase etc.), the PPi is converted into ATP. This generated ATP is utilized by luciferase together with luciferin producing luminescence, whereby a pyrophosphate leaving group (PPi) is again released. This released pyrophosphate can be recycled by ATP generating enzyme to form ATP for use again by luciferase to produce another luminescence event, thereby creating an enzymatic loop that runs numerous times with each pyrophosphate. As polymerase attaches more nucleotides via chain elongation to the template nucleic acid, more of these luminescence creating enzymatic loops are added to the total luminescence, which effectively amplifies the detectable light produced as a result of the elongation of the complementary strand; thereby detecting and/or quantifying the presence of the interrogated target nucleic acid sequence.

In another embodiment (set forth in FIG. 11), a fluorescent label is attached to the terminal phosphate of the nucleotide (or to another region on the pyrophoshphate leaving group; PPi). The excitation spectrum of this fluorescent label matches at least partially with the generated luminescence by oxidation of luciferin. This labelled nucleotide can also optionally include a quencher molecule (either removably or non-removably attached to either to the base or sugar of the nucleotide), whose absorption spectrum overlaps with the emission spectrum of fluorescent label (attached to the terminal phosphate of the nucleotide). The nucleotide that is modified with both the fluorescent label and quencher is referred to herein as a quenched nucleotide. Therefore, upon interaction of the nucleotide analog with the polymerase, polymerase releases pyrophosphate with attached fluorophore (labelled pyrophosphate), separating the fluorescent label from the quencher. When separated, quencher would not be able to absorb the emission of the fluorescent label. Labelled pyropshophate then reacts with ATP generating enzyme and is converted into ATP now labelled by the same fluorescent label (labelled ATP). This labelled ATP will then interact with luciferase generating luminescence and releasing labelled pyrophosphate. Generated luminescence excites the fluorescent label on the labelled pyrophosphate and the excited fluorophore emits light in its specific emission range. The quenched nucleotide is produced to have improved specificity towards polymerase, so that the generated light produced in the range of emission spectra of fluorescent label increases the specificity of the generated signal; because the already incorporated nucleotides are distinguished from the other nucleotides in the background that have not reacted with polymerase. For this embodiment, each nucleotide can be labelled with the same label or different labels.

In another embodiment, referred to herein as Fluorescence activation by continuous elongation of strands (FACES), quenched nucleotides are used in a system that includes only polymerase enzyme (FIG. 12). In this case, an external light source is used to excite the fluorophore. When a quenched nucleotide reacts with polymerase on the positive sample target template nucleic acid strand, labelled pyrophosphate is released generating a fluorescent signal that is proportional to the number of attached nucleotides to the template strand. In other words, the fluorescent signal is proportional to the chain elongation length. The quenched nucleotides that are not incorporated into the elongating strand do not show any emission even under excitation due to the close proximity of fluorescent label with quencher molecule. Fluorescent emission for these non-incorporated nucleotides will be quenched, thereby achieving low amounts to 0 amounts of background.

An advantage, of the invention signal amplification nucleic acid sequence detection and/or quantification methods, is detection of a particular sequence without the need for temperature cycling, or substantial increase of the copy number of DNA. Using the invention methods, in certain embodiments, the light produced from the hybridization of DNA is further amplified with an enzymatic loop, converting each signal to many enzymatic events resulting in chain-elongation-light-emitting reaction instead of an exponential increase of the copy number.

Another advantage of the invention light-signal detection methods provide herein, is that they are much quicker than PCR in providing a detectable, actionable signal. For example, a typical PCR typically has up to around 30-40 cycles, where each cycle takes several minutes to complete leading to a total run duration of at least one to a few hours. One can do shorter runs with PCR, but give up specificity; and those shorter run cases are very limited in terms of primer, probe and template configurations. In contrast, the invention light-signal detection methods for detecting and/or quantifying target nucleic acid sequences (e.g. LACES and FACES) starts to produce a detectable signal as soon as elongation begins, such as in the LACES reaction where the amplification loop is engaged right away. The initial signal that is produced very early (e.g., in a matter of minutes, and the like) is the highest and the most specific signal relative to the later signal. Therefore, the evolution of the signal produced by LACES can be described by a rapid initial rise followed by a long decay; whereas with quantitative PCR, it is an exponential increase that becomes detectable after many cycles and a much longer time-frame, eventually reaching a plateau. More particularly, LACES provides a very specific signal in the initial rapid rise period that occurs much earlier compared to qPCR without giving up specificity.

For example, in particular embodiments of the present invention, either a single polymerase or a plurality of polymerases are confined with the nucleic acid chain elongation reaction mixture (e.g, either in a bulk reaction or in a single droplet), wherein the polymerase(s) is not subject to external light excitation to generate the dNTP incorporation signal to be detected.

In particular embodiments, the disclosed invention is a technology for detecting specific target nucleic acids based on hybridizing a specific interrogating primer-probe to the target sequence and monitoring the detectable light signal (e.g., luminescence, fluorescence, and the like) caused by the individual polymerase enzymes as they incorporate dNTPs sequentially. For example, in a particular embodiment, the invention encompasses a process where each time polymerase incorporates a dNTP or nucleotide analog complementary to the template, a pyrophosphate leaving group (PPi) causes a detectable light (e.g., luminescence and/or fluorescence, and the like) signal to be generated during the incorporation process, wherein such detectable light (e.g., luminescence and/or fluorescence) signal is caused by an enzyme based luminescence reaction as described herein. In other words, in these embodiments, the PPi (or PPi+FL) leaving group causes a luminescence reaction, thereby emitting a detectable light signal for a limited amount of time for that particular dNTP. The process repeats for the next dNTP incorporation (FIG. 1).

More particularly, each time a polymerase incorporates a deoxyribonuleoside triphosphate (dNTP) nucleotide analog to the strand complementary to the template DNA, a detectable light (e.g., luminescence and/or fluorescence) signal is generated. There are five types of dNTPs, namely deoxyadenosine triphosphate (dATP), deoxyguanosine triphosphate (dGTP), deoxycytidine triphosphate (dCTP), and deoxythymidine triphosphate (dTTP) and deoxyuridine triphosphate (dUTP). Upon the completion of attachment of the nucleotide analog to the 3' moiety of the previously attached nucleotide analog, the detectable light signal (e.g., luminescence and/or fluorescence) generated by the leaving group entering into the "polymerase-ATP regenerating enzyme-luciferase" 3-enzyme reaction described herein, is detected by an appropriate optical sensor and/or detection device. In other words, each dNTP incorporated into the template strand results in a detectable pulse of light.

In other embodiments, the detectable light signal (e.g., luminescence and/or fluorescence) generated by the leaving group is amplified, or the intensity of signal of an ATP regenerating enzyme/luciferase amplification loop is increased, in the invention nucleic acid elongation synthesis reaction, by adding Coenzyme A to the chain elongation mixture, in a ratio of Coenzyme A to luciferase effective to increase the intensity of signal of an ATP regenerating enzyme/luciferase amplification loop.

Also provided herein are methods for Target Enrichment by Enrichment by Electrical Modulation, referred to herein as TEEM methods. The invention TEEM methods for enriching or isolating a target-nucleic acid from a nucleic acid-containing sample, said method comprises:
  a. receiving an electrolytic fluid solution including ions and a nucleic acid-containing sample in a fluid chamber having a first and second electrode, wherein at least one electrode has attached thereto a plurality of capture-probes complementary to the target-nucleic acid, wherein the capture probes are at the electrode-solution interface;
  b. applying an annealing-voltage to the electrolytic fluid in proximity to the electrode-solution interface to generate an annealing-pH level by the interface, wherein the annealing-pH level causes annealing of any number of complementary base pairs between nucleic acid within the nucleic acid-containing sample and the capture-probes;
  c. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and
  d. modulating voltages between the annealing-voltage and denaturing-voltage, wherein after the final application of the corresponding pH level (e.g., annealing or denaturing), the target-nucleic acid is enriched or isolated from the nucleic acid-containing sample by remaining bound to the capture-probe on the electrode.

In particular embodiments, once the target-nucleic acid is enriched or isolated, it is then detected. The detection can be by a method selected from the group consisting of LACES, direct detection, PCR, rolling circle amplification, combinations of ligation and PCR, and amplification followed by a detection step, labelled probes, intercalating fluorescent dye. In one embodiment, the material not bound to the capture-probe from the nucleic acid-containing sample is washed away prior to detection. In a particular embodiment, the target-nucleic acid is detected by the invention LACES method provided herein.

In particular embodiments, the pH level is generated via migration of ions in solution. In certain embodiments, the modulating voltages between the annealing-voltage and denaturing-voltage is at a modulation frequency in the range of 0.1-1000 Khz (e.g., 100-1,000,000 cycles per second). In particular embodiments, the density of capture-probes on an electrode is 100 to 1,000,000 oligonucleotide probes per $cm^2$. In certain embodiments, the number of complementary base pairs denatured during the modulating step is selected from a range of 1-20, 1-15, 1-10, or 1-5 base pair double-strands. In particular embodiments, the nucleic acid-containing sample is selected from cells, saliva, urine, blood, hair, semen, saliva, bone, tissue, teeth, cell-lysates, viruses, cellular nucleic acid or genomic nucleic acid.

Also provided herein are methods that combine both the invention TEEM and LACES methods for detecting the presence of a target-nucleic acid. For example, provided herein are methods for detecting the presence of a target-nucleic acid sequence in a nucleic acid-containing sample comprising:
  a. receiving an electrolytic fluid solution including ions and a nucleic acid-containing sample in a fluid chamber having a first and second electrode, wherein at least one electrode has attached thereto a plurality of capture/primer-probes complementary to the target-nucleic acid, wherein the capture/primer-probes are at the electrode-solution interface;
  b. applying an annealing-voltage to the electrolytic fluid in proximity to the electrode-solution interface to generate an annealing-pH level by the interface, wherein the annealing-pH level causes annealing of any number of complementary base pairs between nucleic acid within the nucleic acid-containing sample and the capture/primer-probes;
  c. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and d. modulating the annealing-voltage and denaturing-voltage, wherein after the final application of the corresponding pH level (e.g., annealing or denaturing), the target-nucleic acid is enriched or isolated from the nucleic acid-containing sample by remaining bound to the capture/primer-probe on the electrode, wherein the bound target-nucleic acid is a template strand for template directed elongation synthesis;

e. providing an elongation mixture comprising (i) a polymerase enzyme, (ii) an ATP regenerating enzyme, (iii) a luminescence enzyme (e.g., firefly luciferase), and (iv) a polymerase-ATP regenerating enzyme-luminescence reagent solution having the components for carrying out template directed elongation synthesis of a growing nucleic acid strand, wherein said reagent solution includes an ATP-regenerating-enzyme-substrate, a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;

f. carrying out nucleic acid elongation synthesis such that one or a plurality of nucleotide analogs are added sequentially to the template strand if the capture/primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme yielding ATP, then c) binding the ATP to a luminescence-enzyme, wherein a luminescence-substrate is catalyzed by the luminescence-enzyme to produce luminescence while regenerating the respective leaving group; and g. detecting light from the luminescence while nucleic acid synthesis is occurring, whereby detection of light indicates the presence of the particular target nucleic acid sequence. In one embodiment, the material not bound to the capture/primer-probe from the nucleic acid-containing sample is washed away prior to providing an elongation reaction mixture of step (e).

Also provided herein are invention TEEM methods of enriching or isolating a target-nucleic acid starting from a mammalian-cell sample that includes dielectrophoresis to facilitate preparing the sample. For example, provided herein is a method for enriching or isolating a target-nucleic acid from a mammalian-cell sample, said method comprising:

a. receiving an electrolytic fluid including ions and a mammalian-cell sample in a fluid chamber having a first and second electrode;

b. lysing the cells to form a cell-lysate;

c. applying an asymmetric di-electric field to the solution containing the cell-lysate, wherein total-nucleic acid from the cell-lysate sample is captured by at least one electrode;

d. washing the uncaptured cell-lysate from the fluid chamber;

e. resuspending the total-nucleic acid into the electrolytic fluid solution including ions in the fluid chamber, wherein at least one electrode has attached thereto a plurality of capture-probes complementary to the target-nucleic acid, wherein the capture probes are at the electrode-solution interface;

f. applying an annealing-voltage to the electrolytic fluid in proximity to the electrode-solution interface to generate an annealing-pH level by the electrode-solution interface, wherein the annealing-pH level causes annealing of any number of complementary base pairs between the total-nucleic acid and the capture-probes;

g. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and h. modulating the annealing-voltage and denaturing-voltage, wherein after the final application of the corresponding pH level (e.g., annealing or denaturing), the target-nucleic acid is enriched or isolated from the total-nucleic acid by remaining bound to the capture/primer-probe on the electrode.

Also provided herein are invention TEEM methods of enriching or isolating a target-nucleic acid starting from a cell-lysate sample that includes dielectrophoresis to facilitate preparing the sample. For example, provided herein is a method for enriching or isolating a target-nucleic acid from a cell-lysate sample, said method comprising:

a. receiving an electrolytic fluid solution including ions and a cell-lysate sample in a fluid chamber having a first and second electrode;

b. applying an asymmetric di-electric field to the solution containing the cell lysate sample, wherein total-nucleic acid from the cell-lysate sample is captured by at least one electrode (e.g., the first electrode);

c. washing the uncaptured cell-lysate from the fluid chamber;

d. resuspending the total-nucleic acid into the electrolytic fluid solution including ions in the fluid chamber, wherein at least one electrode (e.g., the first electrode) has attached thereto a plurality of capture-probes complementary to the target-nucleic acid, wherein the capture probes are at the electrode-solution interface;

e. applying an annealing-voltage to the electrolytic fluid in proximity to the electrode-solution interface to generate an annealing-pH level by the electrode-solution interface, wherein the annealing-pH level causes annealing of any number of complementary base pairs between the total-nucleic acid and the capture-probes;

f. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and g. modulating the annealing-voltage and denaturing-voltage, wherein after the final application of the corresponding pH level (e.g., annealing or denaturing), the target-nucleic acid is enriched or isolated by remaining bound to the capture/primer-probe on the electrode.

In particular embodiments, the total-nucleic acid is resuspended into the fluid chamber by terminating the asymmetric di-electric field. In certain embodiments, the cell-lysate is obtained by lysing a mammalian cell-sample within the fluid chamber. In particular embodiments, the target-nucleic acid is detected by a method selected from the group consisting of LACES, direct detection, PCR, rolling circle amplification, combinations of ligation and PCR, and amplification followed by a detection step, labelled probes, intercalating fluorescent dye. In particular embodiments, the material not bound to the capture/primer-probe from the nucleic acid-containing sample is washed away prior to detection. In a particular embodiment, the target-nucleic acid is detected by the LACES method. The mammalian cell-sample is obtained from cells, saliva, urine, blood, hair, semen, saliva, bone, tissue, teeth, cell-lysates, viruses, cellular nucleic acid or genomic nucleic acid.

Also provided herein are methods for both enriching target-nucleic acid (via the invention TEEM method) and for detecting and/or quantifying the presence of the enriched-nucleic acid (via the invention LACES method). For example, provided herein are method for enriching or isolating a target-nucleic acid from a mammalian-cell sample, said method comprising:
a. receiving an electrolytic fluid including ions and a mammalian-cell sample in a fluid chamber having a first and second electrode;
b. lysing the cells to form a cell-lysate;
c. applying an asymmetric di-electric field to the solution containing the cell-lysate, wherein total-nucleic acid from the cell-lysate sample is captured by at least one electrode (e.g., the first electrode);
d. washing the uncaptured cell-lysate from the fluid chamber;
e. resuspending the total-nucleic acid into the electrolytic fluid solution including ions in the fluid chamber, wherein at least one electrode has attached thereto a plurality of capture-probes complementary to the target-nucleic acid, wherein the capture probes are at the electrode-solution interface;
f. applying an annealing-voltage to the electrolytic fluid in proximity to the electrode-solution interface to generate an annealing-pH level by the electrode-solution interface, wherein the annealing-pH level causes annealing of any number of complementary base pairs between the total-nucleic acid and the capture-probes;
g. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and
h. modulating the annealing-voltage and denaturing-voltage, wherein after the final application of the corresponding pH level (e.g., annealing or denaturing), the target-nucleic acid is enriched or isolated from the total-nucleic acid by remaining bound to the capture/primer-probe on the electrode (e.g., the first electrode), wherein the bound target-nucleic acid is a template strand for template directed elongation synthesis;
i. providing an elongation mixture comprising (i) a polymerase enzyme, (ii) an ATP regenerating enzyme, (iii) a luminescence enzyme (e.g., firefly luciferase), and (iv) a polymerase-ATP regenerating enzyme-luminescence reagent solution having the components for carrying out template directed elongation synthesis of a growing nucleic acid strand, wherein said reagent solution includes an ATP-regenerating-enzyme-substrate, a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;
j. carrying out nucleic acid elongation synthesis such that one or a plurality of nucleotide analogs are added sequentially to the template strand if the capture/primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme yielding ATP, then c) binding the ATP to a luminescence-enzyme, wherein a luminescence-substrate is catalyzed by the luminescence-enzyme to produce luminescence while regenerating the respective leaving group; and
k. detecting light from the luminescence while nucleic acid synthesis is occurring, whereby detection of light indicates the presence of the particular target nucleic acid sequence. In a particular embodiment, the capture/primer-probe from the total-nucleic acid is washed away prior to providing an elongation reaction mixture of step (1).

Also provided herein, is an invention TEEM method for enriching or isolating a target-nucleic acid from a nucleic acid-containing sample, said method comprising:
a. receiving an electrolytic fluid solution including ions and a nucleic acid-containing sample in a fluid chamber having a first and second electrode, wherein at least one electrode has attached thereto a plurality of capture-probes complementary to the target-nucleic acid, wherein the capture probes are at the electrode-solution interface; and
b. modulating an electric field formed in proximity to the electrode-solution interface by alternating a annealing-voltage and an denaturing-voltage to generate a respective annealing-pH level and a denaturing-pH level of the electrolytic fluid in proximity to the electrode-solution interface, wherein the annealing-pH level causes annealing of any number of complementary base pairs; and the denaturing-pH level causes the denaturation of double-stranded nucleic acid having a number of complementary base pairs corresponding to a range selected from: 1 to x-5 complementary base pairs; 1 to x-10; 1 to x-15 complementary base pairs; 1 to x-20 complementary base pairs; 1 to x-25 complementary base pairs complementary base pairs, where x is the nucleotide length of the respective capture-probe, wherein after the final application of the annealing-pH level, the target-nucleic acid is enriched or isolated from the nucleic acid-containing sample by remaining bound to the primer-probe on the electrode.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figures 1A, 1B, 1C:
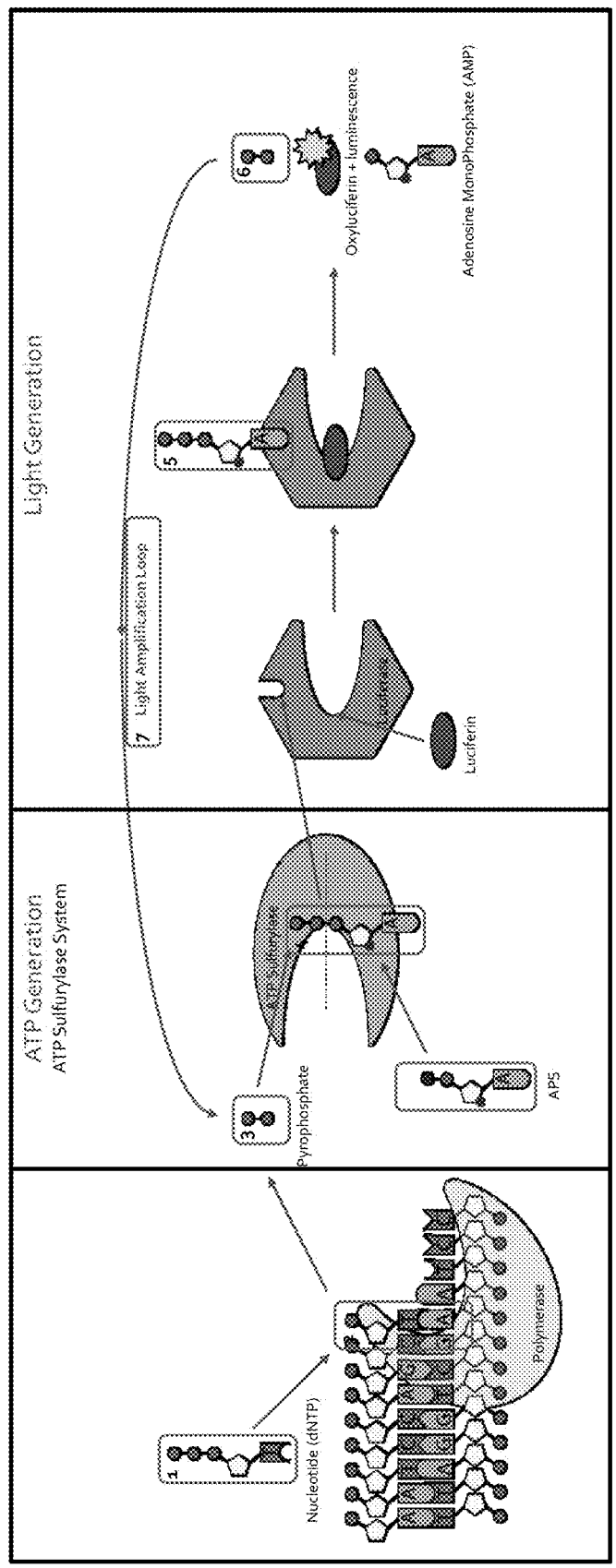
FIG. 1A shows a general illustration of one embodiment of the invention LACES target nucleic acid detection method: DNA Polymerase uses dNTPs or dNTP analogs as building blocks. Upon binding to polymerase, the pyrophosphate is cleaved off for later reactions.
FIG. 1B shows the cleaved pyrophosphate combining with APS by interaction with ATP sulfurylase enzyme, which binds the respective pyrophosphate to adenosine 5'-phosphosulfate (APS), resulting in the formation ATP (ATP).
FIG. 1C shows the reagents, ATP (ATP), luciferin, and firefly luciferase, for the luminescence reaction set forth herein; and the interaction of the reagents in the luminescence reaction, from which the detectable luminescence occurs.
Figure 2:
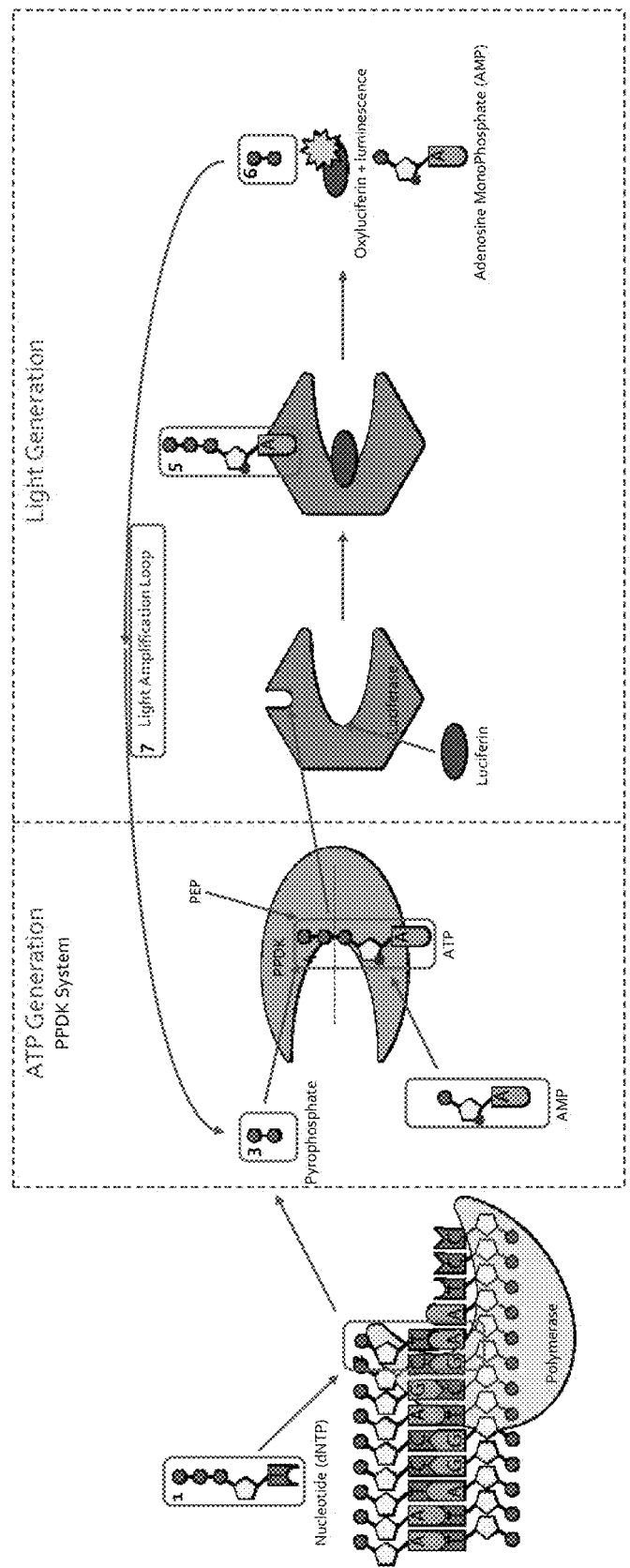
FIG. 2 shows a general illustration of another embodiment of the invention LACES target nucleic acid detection method employing AMP+PEP and the PPDK enzyme. The cleaved pyrophosphate is combined with AMP+PEP by interaction with PPDK enzyme, which binds the respective pyrophosphate to AMP, resulting in the formation ATP (ATP).
Figure 3:
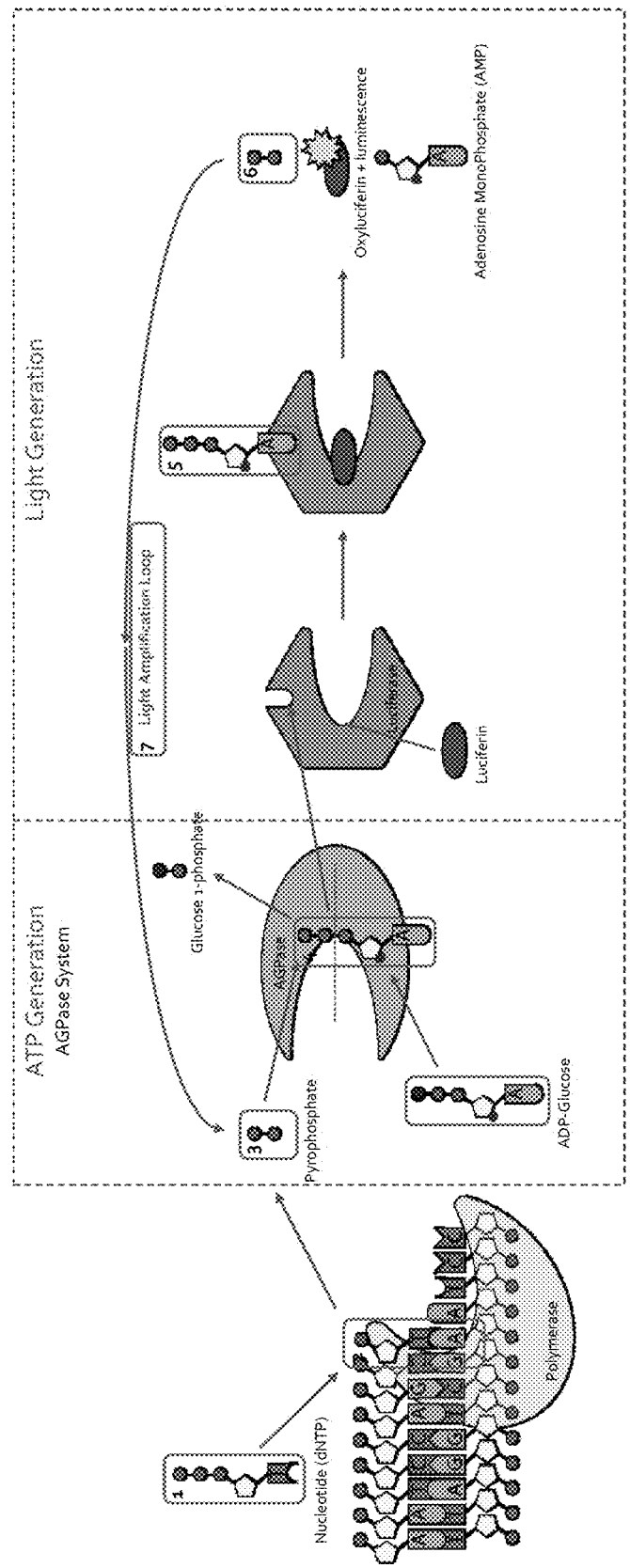
FIG. 3 shows a general illustration of another embodiment of the invention LACES target nucleic acid detection employing ADP-glucose and the AGPPase enzyme. The cleaved pyrophosphate is combined with ADP-glucose by interaction with AGPPase enzyme, which binds the respective pyrophosphate to ADP-glucose, resulting in the formation ATP (ATP).

Provided herein are methods for detecting the presence of a nucleic acid sequence in a sample comprising:
providing a nucleic acid chain elongation mixture comprising (i) a polymerase enzyme, (ii) an ATP regenerating enzyme, (iii) a luminescence enzyme (e.g., firefly luciferase), (iv) a template nucleic acid from the sample, (v) a primer-probe that hybridizes to (e.g., that is complementary to) a particular target nucleic acid sequence, and (vi) a polymerase-ATP regenerating enzyme-luminescence reagent solution having the components for carrying out template directed elongation synthesis of a growing nucleic acid strand, wherein said reagent solution includes an ATP-regenerating-enzyme-substrate (e.g., with APS by ATP Sulfurylase; with ADP-glucose by AGPPase; with AMP+PEP by PPDK, and the like), a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;
carrying out nucleic acid elongation synthesis such that one or a plurality of nucleotide analogs are added sequentially to the template if the primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme (e.g., with APS by ATP Sulfurylase; with ADP-glucose by AGPPase; with AMP+PEP by PPDK, and the like) yielding ATP, then c) binding the ATP to a luminescence-enzyme, wherein a luminescence-substrate is catalyzed by the luminescence-enzyme to produce luminescence, wherein the pyrophosphate leaving group is regenerated; and
detecting light from the luminescence while nucleic acid synthesis is occurring, whereby detection of light indicates the presence of the particular target nucleic acid sequence.

In particular embodiments of the invention methods said methods comprise:
providing a nucleic acid chain elongation mixture comprising (i) a polymerase enzyme, (ii) an ATP sulfurylase, (iii) a luminescence enzyme (e.g., firefly luciferase), (iv) a template nucleic acid from the sample, (v) a primer-probe that hybridizes to (e.g., that is complementary to) a particular target nucleic acid sequence, and (vi) a polymerase-ATP regenerating enzyme-luminescence reagent solution having the components for carrying out template directed synthesis of a growing nucleic acid strand, wherein said reagent solution includes APS, a luminescence-substrate (e.g., luciferin); and a plurality of types of nucleotide analogs; wherein each type of nucleotide analog has a pyrophosphatase leaving group that is cleavable by the polymerase, wherein the pyrophosphate leaving group is cleaved upon polymerase-dependent binding of a respective nucleotide analog to the template strand; or
providing a nucleic acid chain elongation mixture comprising (i) a polymerase enzyme, (ii) an ADPglc pyrophosphorylase (AGPPase), (iii) a luminescence enzyme (e.g., firefly luciferase), (iv) a template nucleic acid from the sample, (v) a primer-probe that hybridizes to (e.g., that is complementary to) a particular target nucleic acid sequence, and (vi) a polymerase-AGPPase-luminescence reagent solution having the components for carrying out template directed synthesis of a growing nucleic acid strand, wherein said reagent solution includes ADP-glucose, a luminescence-substrate (e.g., luciferin); and a plurality of types of nucleotide analogs; wherein each type of nucleotide analog has a pyrophosphatase leaving group that is cleavable by the polymerase, wherein the pyrophosphatase leaving group is cleaved upon polymerase-dependent binding of a respective nucleotide analog to the template strand; or
providing a nucleic acid chain elongation mixture comprising (i) a polymerase enzyme, (ii) a pyruvate orthophosphate dikinase (PPDK), (iii) a luminescence enzyme (e.g., firefly luciferase), (iv) a template nucleic acid from the sample, (v) a primer-probe that hybridizes to (e.g., that is complementary to) a particular target nucleic acid sequence, and (vi) a polymerase-PPDK-luminescence reagent solution having the components for carrying out template directed synthesis of a growing nucleic acid strand, wherein said reagent solution includes AMP and phosphoenalpyruvate (PEP), a luminescence-substrate (e.g., luciferin); and a plurality of types of nucleotide analogs; wherein each type of nucleotide analog has a pyrophosphatase leaving group that is cleavable by the polymerase, wherein the pyrophosphatase leaving group is cleaved upon polymerase-dependent binding of a respective nucleotide analog to the template strand; and
carrying out nucleic acid synthesis such that a plurality of nucleotide analogs are added sequentially to the template whereby: a) a nucleotide analog associates with the polymerase, b) the nucleotide analog is incorporated on the template strand by the polymerase when the pyrophosphatase leaving group on that nucleotide analog is cleaved by the polymerase, wherein the pyrophosphatase leaving group is combined with either: APS by ATP Sulfurylase, ADP-glucose by AGGPase; and/or AMP by PPDK, yielding ATP, then c) binding the ATP to a luminescence-enzyme (firefly luciferase), wherein a luminescence-substrate (luciferin) is catalyzed by the luminescence-enzyme (luciferase) to produce luminescence for a limited (transient/discreet) period of time and wherein the pyrophosphate leaving group is regenerated; and detecting light from the luminescence while nucleic acid synthesis is occurring, whereby detection of light indicates the presence of the particular target nucleic acid sequence.

As used herein, "polymerase-ATP regenerating enzyme-luciferase" or grammatical variations thereof, refers to any concatenated 3 Enzyme System known in the art that can be used in the invention methods to utilize the pyrophosphate leaving group generated by the polymerase chain elongation reaction, and convert the pyrophosphate leaving group (PPi; FIG. 1B) into ATP. For example, a concatenated 3 Enzyme polymerase-ATP regenerating enzyme-luciferase system can be selected from the group consisting of: a polymerase-ATP sulfurylase-luminescence enzyme system; a polymerase-AGPPase-luminescence (as disclosed in Lee et al., Analytical Biochemistry, 399 (2010) 168-173; incorporated herein by reference in its entirety for all purposes); a polymerase-PPDK-luminescence enzyme system (as disclosed in Zhou et al., Anal. Chem. 2006, 78, 4482-4489; incorporated herein by reference in its entirety for all purposes); and the like.

As used herein, the phrase "ATP-regenerating-enzyme-substrate" refers to the native substrate for a respective ATP-regenerating enzyme used herein. For example, the native substrate used herein for ATP sulfurylase is APS; for AGGPase is ADP-glucose; for PPDK is AMP+PEP, and the like.

As use herein, the term "ATP regenerating enzyme/Luciferase loop" or "ATP regenerating enzyme/Luciferase signal amplification loop" grammatical variations thereof (e.g., ATP Sulfurylase/Luciferase loop, AGPPase/Luciferase loop, PPDK/luciferase loop, and the like), refers generally to an enzymatic loop between the ATP regenerating enzyme and luciferase as set forth in Example 3 herein and in FIG. 1B-1G, whereby following the luminescent reaction catalyzed by luciferase a new pyrophosphate molecule is released (PPi) (FIG. 1F). This newly released PPi-FL can once again be a substrate for the ATP regenerating enzyme (e.g., ATP Sulfurylase, AGPPase, PPDK, and the like) thereby generating an enzymatic loop between ATP regenerating enzyme (e.g., ATP Sulfurylase, AGPPase, PPDK, and the like) and luciferase (FIG. 1G. Top). As shown in FIG. 1B-1G, within this loop PPi is recycled by ATP Sulfurylase and converted into ATP (ATP), which can then be catalyzed by luciferase releasing PPi. This will generate successive luminescence signals from the pyrophosphate leaving group, and thereby serve as an amplification mechanism for the detection signal for each respective nucleotide.

As used herein, the phrase "nucleic acid chain elongation mixture" or "chain elongation mixture," or grammatical variations thereof, refers to the components that are used to carry out the invention LACES nucleic acid chain elongation reactions. In one embodiment, the chain elongation mixture includes (i) a polymerase enzyme, (ii) an ATP regenerating enzyme (e.g., ATP Sulfurylase, AGPPase, PPDK, and the like), (iii) a luminescence enzyme (e.g., firefly luciferase), (iv) a template nucleic acid from the sample, (v) a primer-probe that hybridizes to (e.g., that is complementary to) a particular target nucleic acid sequence that is being interrogated, and (vi) a polymerase-ATP regenerating enzyme-luminescence reagent solution having the components for carrying out template directed synthesis of a growing nucleic acid strand, wherein said reagent solution includes either APS, ADP-glucose, AMP+PEP, or the like, a luminescence-substrate (e.g., luciferin); and a plurality of types of nucleotide analogs therein. In accordance with the present invention, the chain elongation mixture used provides the following advantages in the invention target nucleic acid detection methods over previous methods: the polymerase employed functions in its ideal state; there is no need to modify a polymerase enzyme; the use of high nucleotide (e.g., dNTP) concentrations results in optimum efficiency; does not require sophisticated optics or nano-structured chip design, which reduces cost; it provides high specificity; and provides long nucleic acid chain elongation lengths (e.g., about 50 Kb to 1 gene/cell, which rapidly and intensely amplifies the luminescence signal signifying the presence of the interrogated target nucleic acid.

As used herein, the phrase "template nucleic acid sample" or "target template nucleic acid sample," "target-nucleic acid" or grammatical variations thereof, refers to any suitable polynucleotide, including double-stranded DNA, single-stranded DNA, single-stranded DNA hairpins, DNA/RNA hybrids, single-stranded RNA, RNAs with a recognition site for binding of one or more of the primer-probe, capture-probe, capture/primer-probe, polymerizing agent, and/or RNA hairpins. Further, target polynucleotides suitable as template nucleic acids or target-nucleic acids for use in the invention nucleic acid target detection methods may be a specific portion of a genome from any cell, such as an intron, regulatory region, allele, variant or mutation; the whole genome; or any portion thereof. In other embodiments, the target polynucleotides may be mRNA, tRNA, rRNA, ribozymes, antisense RNA or RNAi. In other embodiments, the target polynucleotide sample may be of any length, such as between about 10 bases up to about 100,000 bases, between about 10,000 bases up to about 90,000 bases, between about 20,000 bases up to about 80,000 bases, between about 30,000 bases up to about 70,000 bases, between about 40,000 bases up to about 60,000 bases, or longer, with a typical range being between about 10,000-50,000 bases. Also contemplated herein, are target template nucleic acid lengths of between about 100 bases and 10,000 bases.

The template nucleic acid samples (also referred to herein as target-nucleic acids) suitable for use herein can be obtained from a variety of sources well known in the art. For example, nucleic acid samples from cellular DNA, viral DNA/RNA, circulating cell free DNA, circulating tumor DNA, DNA/RNA from saliva, DNA/RNA from blood, DNA/RNA from agricultural samples, animal biological fluids, environmental samples (fresh water sources, sea/ocean samples) and the like.

As used herein, the term "primer-probe" refers to a primer that can initiate chain elongation that also functions as a probe to identify a particular target nucleic acid sequence, preferably from among a sample of unknown nucleic acids being interrogated. Since there is no temperature cycling and denaturation, and hybridization cycles do not exist such as for PCR, there is a great deal of flexibility in the probe design in terms of length and sequence that can be used in the invention methods. With the invention methods provided herein, designing one oligonucleotide probe (e.g., a primer-probe) is sufficient, instead of 2 primers required for PCR. The length of the primer-probe can be any size, so long as it accurately binds to its respective target nucleic acid sequence from among the template nucleic acid sample. For example, a variety of ranges of primer-probe lengths suitable for use herein can be selected from the group consisting of: 20-100, 20-90, 20-80, 20-70, 20-60, 20-50, 20-40, 20-30, 5-100, 10-100, 30-100, 40-100, 50-100, 60-100, 70-100, 80-100, 90-100, 15-150, 10-200, 5-300, 20-200, 20-300, 20-400, 20-500, 20-600, 20-700, 20-800, 20-900, 20-1000, at least 5, at least 10, at least 15, at least 20, at least 30, at least 40, at least 50, at least 60, at least 70, at least 80, at least 90, at least 100, at least 150, at least 200, at least 300, at least 400, at least 500, at least 600, at least 700, at least 800, at least 900 at least 1000 nucleotide bases.

Other suitable ranges of primer-probe lengths suitable for use herein can be selected from the group consisting of: 5-1000 bases, 10-950, 15-900, 20-800, 25-700, 30-600, 35-500, 40-400, 50-300, 25-250, 25-200, 25-150, 25-100, 25-90, 25-80, 25-70, 25-60, 25-50 base in length. In other embodiments, the primer-probe is in the range of 20-100 bases. In other embodiments, those of skill in the art can select a longer nucleotide sequence for the primer-probe length can be selected from the group consisting of: 25, 30, 40, 45, 50, 55, 60, 65, 70, 80, 85, 90, 95, 100, 110, 120, 130, 140, 150, 160, 170, 180, 190, and 200 bases or more to increase specificity. In other embodiments, as with PCR, a probe length about 20 bases is contemplated is also contemplated for use herein.

As used herein, the phrase "polymerase-ATP regenerating enzyme-luminescence reagent solution," grammatical variations thereof using either of ATP Sulfurylase, AGPPase, PPDK, and the like as the ATP regenerating enzyme, or "reagent solution" refers to the mixture of components necessary for carrying out the template directed synthesis of a growing nucleic acid. In one embodiment using ATP sulfurylase, the polymerase reagent solution for use with a polymerase, e.g., DNA pol I, ATP sulfurylase, and the luminescence-enzyme (e.g., luciferase, and the like), includes a APS (adenosine 5' phosphosulfate), luciferin and suitable concentrations of dNTPs, e.g., the nucleotide analogs described herein. In another embodiment using AGPPase, the polymerase reagent solution for use with a polymerase, e.g., DNA pol I, AGPPase, and the luminescence-enzyme (e.g., luciferase, and the like), includes a ADP-glucose, luciferin and suitable concentrations of dNTPs, e.g., the nucleotide analogs described herein. In another embodiment using PPDK, the polymerase reagent solution for use with a polymerase, e.g., DNA pol I, PPDK, and the luminescence-enzyme (e.g., luciferase, and the like), includes a AMP+PEP, luciferin and suitable concentrations of dNTPs, e.g., the nucleotide analogs described herein. In a particular embodiment, the concentrations of dNTPs employed are much higher than has been heretofore possible because, in part, of the low fluorescent background resulting from the leaving groups (e.g., fluorescent pyrophosphate; PPi) advantageously employed in the invention methods. Because the ATP forming enzyme (e.g., ATP Sulfurylase, AGPPase, PPDK, and the like) and polymerase rates can vary significantly depending on the type and source of the enzymes, the rate of ATP formation achieved by the ATP regenerating enzyme (e.g., ATP Sulfurylase, AGPPase, PPDK, and the like) reaction employed herein can be adjusted separately by adjusting reaction conditions such as ATP regenerating enzyme concentration, and the like as described herein.

As used herein the phrase "ATP reaction" refers to any reaction that can combine a pyrophosphate (e.g., a leaving group; PPi) with an ATP regenerating substrate (e.g., either Adenosine 5' phosphosulfate (APS), ADP-glucose, AMP+PEP, or the like) to form ATP (ATP), as set forth in FIGS. 1B and 1C. In one embodiment for use herein, a pyrophosphate leaving group can be combined with APS using the ATP sulfurylase enzyme, or the like. In another embodiment for use herein, a pyrophosphate leaving group can be combined with ADP-glucose using the AGPPase enzyme, or the like. In another embodiment for use herein, a pyrophosphate leaving group can be combined with AMP+PEP using the PPDK enzyme, or the like.

As used herein the phrase "luminsescence reaction" refers to any reaction that can produce the emission of light that does not derive at all or solely derives energy from the temperature of the emitting body (i.e., emission of light other than incandescent light). "Luminescence" includes, but is not limited to, fluorescence, phosphorescence, thermoluminescence, chemiluminescence, electroluminescence and bioluminescence. "Luminescent" refers to an object that exhibits luminescence. In preferred embodiments, the light is in the visible spectrum. However, the present invention is not limited to visible light, but includes electromagnetic radiation of any frequency. In one embodiment, the luminescence reaction employed herein is caused by the luminescence enzyme, luciferase (e.g., firefly luciferase) catalyzing the luminescence-substrate, luciferin, using ATP (ATP) as a cofactor to produce luminescence, oxyluciferin, AMP and also to regenerate the pyrophosphate (PPi) for looping back to form another ATP (see FIGS. 1D-1F).

For example, in one embodiment, the iterative chain elongation cycle contemplated herein involves a first ATP reaction of PPi with APS, catalyzed by the ATP-sulfurylase enzyme, which results in the production of ATP and inorganic sulphate. In a second reaction, the luminescence reaction, luciferin and luciferase consume ATP as an energy source to generate light, AMP and oxyluciferin and to regenerate pyrophosphate (PPi) (FIG. 1C). Thus, after each respective dNTP analog is incorporated, a quantum of light is generated for each molecule of pyrophosphate (PPi) in solution via the second luminescence reaction. In the course of the reactions for one embodiment contemplated herein, APS and luciferin are consumed and AMP and oxyluciferin are generated, while ATP sulfurylase and luciferase remain constant. The invention is not limited as to the type of luciferase used. Although certain disclosed embodiments utilized firefly luciferase, any luciferase known in the art may be used in the disclosed methods.

In accordance with the present invention, it has been found that Coenzyme A stabilizes the luciferase/luciferin couple or complex by preventing the degradation/deactivation of luciferase, which has the effect of increasing the intensity of signal of an ATP regenerating enzyme/luciferase amplification loop in an invention nucleic acid target detection reaction. Accordingly, provided herein are methods of increasing the intensity of signal of an ATP regenerating enzyme/luciferase amplification loop in a chain elongation reaction, comprising conducting the invention LACES target nucleic acid detection methods set forth herein; and adding Coenzyme A to the chain elongation mixture, in a ratio of Coenzyme A to luciferase effective to increase the intensity of signal of an ATP regenerating enzyme/luciferase amplification loop Thus, in some embodiments, the amount of Coenzyme A used herein can be added to the invention chain elongation mixture and solutions as a ratio of Coenzyme A:Luciferase, effective to increase the intensity of signal of an ATP regenerating enzyme/luciferase amplification loop in a chain elongation reaction. In some embodiments, suitable Coenzyme A:Luciferase ratios contemplated for use herein can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 Coenzyme A:Luciferase, and the like. In other embodiments, suitable Luciferase:Coenzyme A ratios, effective to increase the intensity of signal of an ATP regenerating enzyme/luciferase amplification loop in a LACES chain elongation reaction, contemplated for use herein can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 Luciferase:Coenzyme A, and the like.

As used herein a "polymerase enzyme" refers to the well-known proteins responsible for carrying out nucleic acid synthesis. Exemplary polymerases suitable for use herein include DNA polymerases, RNA polymerases and reverse transcriptases. In a particular embodiment, a polymerase enzyme for use herein is a DNA polymerase. In natural polymerase mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation can be relatively complex. During the reaction process, the polymerase enzyme undergoes a series of conformational changes.

Suitable polymerase enzymes for use herein include DNA polymerases, which can be classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of nomenclature, see, e.g., Burgers et al. (2001) "Eukaryotic DNA polymerases: proposal for a revised nomenclature" J Biol Chem. 276(47):43487-90. For a review of polymerases, see, e.g., Hubscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274: 17395-17398; each of which are incorporated herein by reference in their entirety. The basic mechanisms of action for many polymerases have been determined. The sequences of literally hundreds of polymerases are publicly available, and the crystal structures for many of these have been determined, or can be inferred based upon similarity to solved crystal structures for homologous polymerases.

Many such polymerases suitable for nucleic acid chain elongation are readily available. For example, human DNA Polymerase Beta is available from R&D systems. Suitable DNA polymerase for use herein, include DNA polymerase I that is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. PHI.29 DNA polymerase is available from e.g., Epicentre. Poly A polymerase, reverse transcriptase (FIG. 15 $3^{rd}$ panel), Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Other commercial DNA polymerases include PhusionhM High-Fidelity DNA Polymerase, available from New England Biolabs; GoTaq® Flexi DNA Polymerase, available from Promega; RepliPHI™ .PHI.29 DNA Polymerase, available from Epicentre Biotechnologies; PfuUltra™ Hotstart DNA Polymerase, available from Stratagene; KOD HiFi DNA Polymerase, available from Novagen; and many others.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584, 481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases (FIG. 15 $3^{rd}$ panel), PHI-29 related polymerases including wild type PHI-29 polymerase and derivatives of such polymerases such as exonuclease deficient forms, T7 DNA polymerase, T5 DNA polymerase, an RB69 polymerase, etc.

In addition, the polymerases can be further modified for application-specific reasons, such as to increase photostability, e.g., as taught in U.S. patent application Ser. No. 12/384,110 filed Mar. 30, 2009, to improve activity of the enzyme when bound to a surface, as taught, e.g., in WO 2007/075987, and WO 2007/076057, or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

In another embodiment of the invention nucleic acid target sequence detection methods (set forth in FIG. 11), a fluorescent label is attached to the terminal phosphate of the dNTP or nucleotide analog (or to another region on the pyrophoshphate leaving group; PPi). The excitation spectrum of this fluorescent label matches at least partially the generated luminescence by oxidation of luciferin. This labelled nucleotide can also optionally include a quencher molecule, either removably or non-removably attached to either the base or sugar of the nucleotide, having an absorption spectrum that overlaps with the emission spectrum of fluorescent label (attached to the terminal phosphate of the nucleotide). The nucleotide that is modified with both the fluorescent label and quencher is referred to herein as a quenched nucleotide. Therefore, upon interaction of the nucleotide analog with the polymerase, polymerase releases pyrophosphate with attached fluorophore (labelled pyrophosphate), separating the fluorescent label from the quencher. When separated, quencher would not be able to absorb the emission of the fluorescent label. Labelled pyrophosphate then reacts with ATP generating enzyme and is converted into ATP now labelled by the same fluorescent label (labelled ATP). This labelled ATP will then interact with luciferase generating luminescence and releasing labelled pyrophosphate. Generated luminescence excites the fluorescent label on the labelled pyrophosphate and the excited fluorophore emits light in its specific emission range. The quenched nucleotide is produced to have improved specificity towards polymerase, so that the generated light produced in the range of emission spectra of fluorescent label increases the specificity of the generated signal; because the already incorporated nucleotides are distinguished from the remaining nucleotides in the background that have not reacted with polymerase. For this embodiment, each nucleotide can be labelled with the same label or different labels or only one, or only two, or only three nucleotides can be labelled with the same or different or any other combination of labels.

Figure 11:
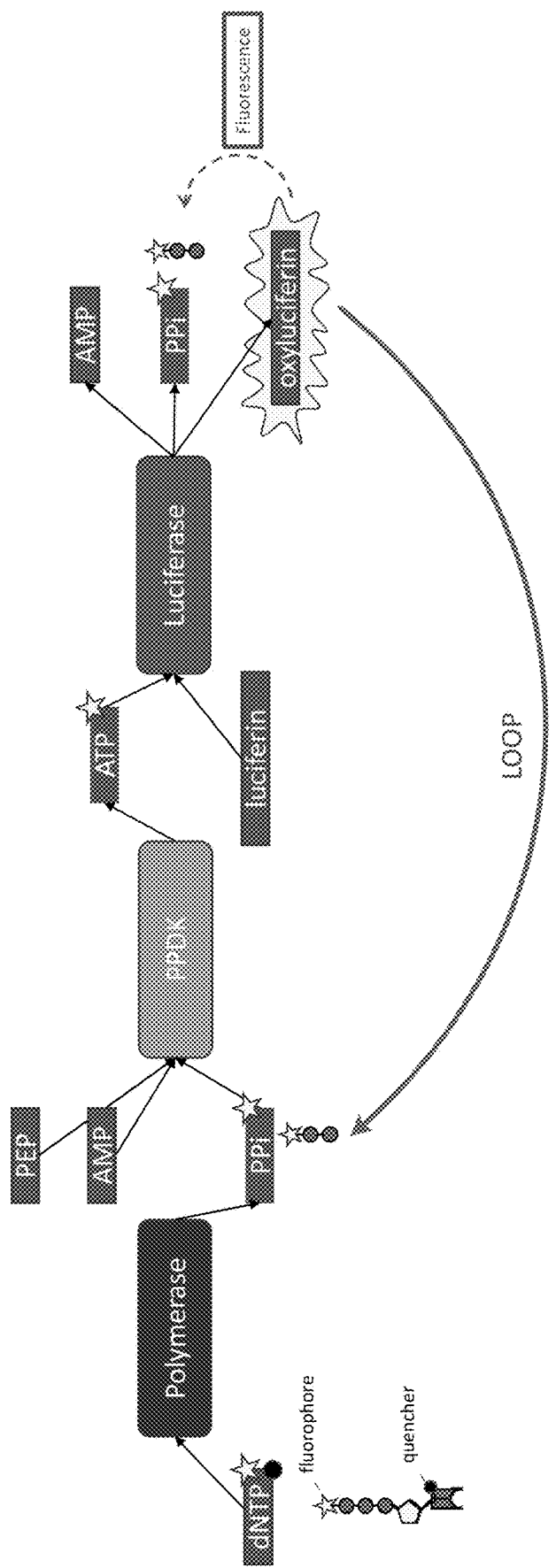
FIG. 11 shows a general illustration of another embodiment of the invention target nucleic acid detection method employing quenched nucleotides having a fluorescent label or otherwise detectable label thereon, and the AMP+PEP and the PPDK enzyme system. The cleaved labelled pyrophosphate (i.e., PPi+FL) is combined with AMP+PEP by interaction with PPDK enzyme, which binds the respective pyrophosphate to AMP, resulting in the formation ATP (ATP) for subsequent use in the luciferase reaction to generate detectable luminescence and/or fluorescent light, which is amplified by the enzymatic loop described herein.

In a preferred embodiment, the nucleotide analog is modified by adding a fluorophore to a terminal phosphate (see, e.g, Yarbrough et al., J. Biol. Chem., 254:12069-12073, 1979; incorporated herein by reference in its entirety for all purposes), such that when the PPi labeled leaving group (e.g., PPi+FL) is generated by the polymerase when the nucleotide analog is incorporated into the template strand, that labeled pyrophosphate is able to be combined with Adenosine 5' phosphosulfate by ATP Sulfurylase to form a labeled-ATP (ATP+FL) as shown in FIG. 11.

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361, which are incorporated by reference herein for all purposes). Such nanocrystal materials are generally commercially available from, e.g., Life Technologies, (Carlsbad Calif.). Again, such compounds may be present as individual labeling groups or as interactive groups or pairs, e.g., with other inorganic nanocrystals or organic fluorophores. In some cases fluorescent proteins can be used such as green fluorescent protein (GFP, EGFP), blue fluorescent protein (EBFP, EBFP2, Azurite, mKalama1) cyan fluorescent protein (ECFP, Cerulean, CyPet) and yellow fluorescent protein derivatives (YFP, Citrine, Venus, YPet). Also contemplated for use herein is fluorescent cell barcoding using multipole fluorescence dyes procuding multiple color coded signals for detection, such as described in Krutzek et al., Curr Protoc Cytom. 2011 January; CHAPTER: Unit-6.31. (doi:10.1002/0471142956.cy0631s55); which is incorporated herein by reference in its entirety for all purposes.

Fluorescence Activation by Continuous Elongation of Strands (FACES)

Figure 12:
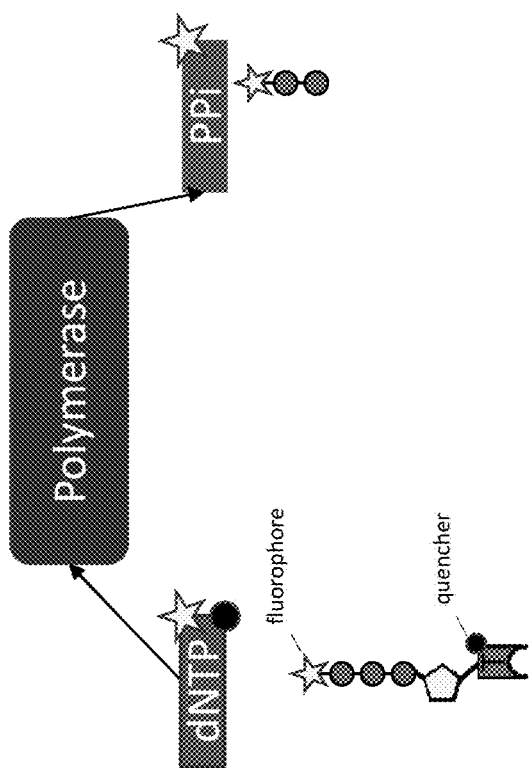
FIG. 12 shows a general illustration of an embodiment of the invention FACES target nucleic acid detection method employing quenched nucleotides having a fluorescent label or otherwise detectable label thereon, and the polymerase enzyme system. The cleaved labelled pyrophosphate (i.e., PPi+FL) is combined with AMP+PEP by interaction with PPDK enzyme, which binds the respective pyrophosphate to AMP, resulting in the formation ATP (ATP) for subsequent use in the luciferase reaction to generate detectable luminescence and/or fluorescent light.

In another embodiment, referred to herein as Fluorescence activation by continuous elongation of strands (FACES), "quenched nucleotides" having both a fluorophore and a quencher molecule attached therein are used in the invention methods and systems that includes only polymerase enzyme (see FIG. 12). In this method provided herein, an external light source is used to excite the fluorophore. When a quenched nucleotide reacts with polymerase and is incorporated into the elongating nucleic acid strand as a result of the primer-probe binding the target nucleic acid sequence with the unknown sample being interrogated, a labelled pyrophosphate is released generating a fluorescent signal that is proportional to the number of attached labelled nucleotide analogs to the template strand. In other words, the fluorescent signal is proportional to the chain elongation length. The quenched nucleotides that are not incorporated into the elongating strand do not show any fluorescent emission even under excitation due to the close proximity of fluorescent label with quencher molecule. Fluorescent emission for these non-incorporated dNTPs or nucleotide analogs will be quenched and not detected as background.

In other embodiments, the invention systems described herein that utilize fluorescent labels can also be utilized with external excitation. Fluorescent labels can be selected in a way that their excitation and emission wavelengths are far from the luminescence spectrum so that there is no coupling with the luciferase reaction. Luciferase reaction is only used to recycle labelled ATP and produce labelled pyrophosphate. In the end, again a loop is utilized, but, this time labelled pyrophosphates that are generated by polymerase are excited with an external light source.

Those of skill in the art can readily determine which instruments are suitable, whether the assays require multiplexing or high sample throughput, and which type of fluorescent label, either alone o in combination with a respective quencher (e.g., a non-removable quencher) provides the specificity and sensitivity required to meet the respective nucleic acid detection method applications. The fluorophores listed in Table 1 can be used with alternative fluorophores listed that exhibit similar Interactive Fluorophore and excitation and emission spectra and are available from different vendors; whereas, Table 2 provides a list of exemplary quencher moieties.

The following guidelines can be followed in choosing the appropriate fluorophore/quencher combinations for the different types of fluorophore labelled nucleotides and detection instruments:

Based on the spectrofluorometric instrument that is utilized, appropriate fluorophore labels selected that can be excited and detected by the optics of the instrument. Instruments equipped with an Argon blue-light laser are optimal for excitation of fluorophores with an excitation wavelength between 500 and 540 nm, however fluorophores with a longer excitation maximum are less well, or not at all, excited by this light source. Instruments with a white light source, such as a Tungsten-halogen lamp, use filters for excitation and emission, and are able to excite and detect fluorophores with an excitation and emission wavelength between 400 and 700 nm, with the same efficiency. This is also the case for instruments that use light emitting diodes as excitation source and emission filters for the detection of a wide range of fluorophores.

If the assay is designed to detect one target DNA sequence and only one fluorescent label will be used, then FAM, TET, or HEX (or one of their alternatives listed in Table 1) will be a good fluorophore to label the respective nucleotide. These fluorophores can be excited and detected on all available spectrofluorometric instruments. In addition, because of the availability of phosphoramidites derivatives of these fluorophores and the availability of quencher-linked control pore glass columns, fluorescent nucleotides with these labels can be entirely synthesized in an automated process, with the advantage of relatively less expensive and less labor intensive manufacture.

TABLE 1

Fluorophore labels for fluorescent hybridization probes

| Fluorophore | Alternative Fluorophore | Excitation (nm) | Emission (nm) |
|---|---|---|---|
| FAM | | 495 | 515 |
| TET | CAL Fluor Gold 540 [A] | 525 | 540 |
| HEX | JOE, VIC [B], CAL Fluor Orange 560 [A] | 535 | 555 |
| Cy3 [C] | NED [B], Quasar 570 [A], Oyster 556 [D] | 550 | 570 |
| TMR | CAL Fluor Red 590 [A] | 555 | 575 |
| ROX | LC red 610 [E], CAL Fluor Red 610 [A] | 575 | 605 |
| Texas red | LC red 610 [E], CAL Fluor Red 610 [A] | 585 | 605 |
| LC red 640 [E] | CAL Fluor Red 635 [A] | 625 | 640 |
| Cy5 [C] | LC red 670 [E], Quasar 670 [A], Oyster 645 [D] | 650 | 670 |
| LC red 705 [E] | Cy5.5 [C] | 680 | 710 |

[A] CAL and Quasar fluorophores are available from Biosearch Technologies;
[B] VIC and NED are available from Applied Biosystems;
[C] Cy dyes are available from Amersham Biosciences;
[D] Oyster fluorophores are available from Integrated DNA Technologies; and
[E] LC (Light Cycler) fluorophores are available from Roche Applied Science.

If the assay is designed for the detection of two or more target DNA sequences (multiplex nucleic acid target detection assays), and therefore two or more fluorescently labelled nucleotides will be used, choose fluorophores with absorption and emission wavelengths that are well separated from each other (minimal spectral overlap). Most instruments have a choice of excitation and emission filters that minimize the spectral overlap between fluorophores. To the extent that spectral overlap occurs, the instruments are supported by software programs with built-in algorithms to determine the emission contribution from each of the fluorophores present in the chain elongation reaction. In addition, most instruments have the option to manually calibrate the optics for the fluorophores utilized in the assay to further optimize the determination of emission contribution of each fluorophore.

For the design of fluorescent nucleotides that utilize fluorescence resonance energy transfer (FRET), fluorophore-quencher pairs that have sufficient spectral overlap should be chosen. Fluorophores with an emission maximum between 500 and 550 nm, such as FAM, TET and HEX, are best suitably quenched by quenchers with absorption maxima between 450 and 550 nm, such as dabcyl and BHQ-1 (see Table 2 for alternative quencher labels). Fluorophores with an emission maximum above 550 nm, such as rhodamines (including TMR, ROX and Texas red) and Cy dyes (including Cy3 and Cy5) are suitably quenched by quenchers with absorption maxima above 550 nm (including BHQ-2).

TABLE 2

Quencher labels for fluorescent hybridization probes

| Quencher | Absorption Maximum (nm) |
|---|---|
| DDQ-I [A] | 430 |
| Dabcyl | 475 |
| Eclipse [B] | 530 |
| Iowa Black FQ [C] | 532 |
| BHQ-1 [D] | 534 |
| QSY-7 [E] | 571 |
| BHQ-2 [D] | 580 |
| DDQ-II [A] | 630 |
| Iowa Black RQ [C] | 645 |
| QSY-21 [E] | 660 |
| BHQ-3 [D] | 670 |

[A] DDQ or Deep Dark Quenchers are available from Eurogentec;
[B] Eclipse quenchers are available from Epoch Biosciences;
[C] Iowa quenchers are available from Integrated DNA Technologies;
[D] BHQ or Black Hole quenchers are available from Biosearch Technologies; and
[E] QSY quenchers are available fom Molecular Probes.

For the design of fluorescent nucleotides that utilize contact quenching, any non-fluorescent quencher can serve as a good acceptor of energy from the fluorophore. For example, in particular embodiments, Cy3 and Cy5 are best quenched by the BHQ-1 and BHQ-2 quenchers.

Fluorophores exhibit specific quantum yields. Fluorescence quantum yield is a measure of the efficiency with which a fluorophore is able to convert absorbed light to emitted light. Higher quantum yields result in higher fluorescence intensities. Quantum yield is sensitive to changes in pH and temperature. Under most nucleic chain elongation reaction conditions, pH and temperature do not change much and therefore the quantum yield will not change significantly.

As set forth herein, nucleotides can quench the fluorescence of fluorophores, with guanosine being the most efficient quencher, followed by adenosine, cytidine and thymidine (see. e.g, Seidel, C. A. M., Schulz, A. and Sauer, M. M. H. (1996) Nucleobase-specific quenching of fluorescent dyes. 1. Nucleobase one-electron redox potentials and their correlation with static and dynamic quenching efficiencies. J. Phys. Chem. 100, 5541-5553; incorporated herein by reference in its entirety for all purposes). In general, luorophores with an excitation wavelength between 500 and 550 nm are quenched more efficiently by nucleotides than fluorophores with longer excitation wavelengths.

Method of Achieving Continuous Long Nucleic Acid Chain Elongation-Lengths

To increase the detectable light signal (e.g., luminescence and/or fluorescence) detected, the ability to achieve long nucleic acid chain elongation-lengths is desired so as to increase the intensity of the detectable light signal (e.g., luminescence and/or fluorescence) signal indicating the presence of the interrogated target nucleic acid. Current chain elongation approaches are limited in their ability to achieve long nucleic acid chain elongation-lengths. In particular, for each individual chain elongation event this limitation comes from the relative affinity of the polymerase to the template nucleic acid. During the chain elongation reaction, polymerase will eventually fall from the template nucleic acid (e.g., DNA or RNA, and the like) thereby terminating the dNTP chain elongation reaction at that respective nucleic acid chain elongation length.

In accordance with the present invention, polymerase enzymes can be added to the chain elongation reaction mixture in an amount corresponding to a plurality of polymerase enzymes for each primer-probe in the reaction mixture.

In particular embodiments of invention target nucleic detection continuous nucleic acid chain elongation methods (e.g. LACES and FACES), especially where a plurality of polymerase are used to elongate each respective target template nucleic acid in a nucleic acid sample, the overall nucleic acid chain elongation length is only limited by the length of target template nucleic acid that is provided to a particular reaction confinement area. For example, the overall nucleic acid chain elongation lengths contemplated herein that can be achieved by using one or a plurality of polymerases for each single target nucleic acid template within the sample, are up to the lengths of entire chromosomes, e.g., 50 million up to about 300 million base pairs (e.g, 300 Mbp), and the like. In other certain embodiments contemplated herein, nucleic acid chain elongation lengths achieved by the invention chain elongation nucleic acid detection methods can be selected from the group consisting of at least: 200 bp, 300 bp, 400 bp, 500 bp, 600 bp, 700 bp, 800, bp, 900 bp, 1000 bp (i.e., 1 kbp), 5 kbp 10 kbp, 20 kbp, 30 kbp, 40 kbp, 50 kbp, 100 kbp, 200 kbp, 300 kbp, 400 kbp, 500 kbp, 600 kbp, 700 kbp, 800 kbp, 900 kbp, 1000 kbp (1 Mbp), 5 Mbp, 10 Mbp, 20 Mbp, 50 Mbp, 75 Mbp, 100 Mbp, 200 Mbp, 300 Mbp, 400 Mbp, 500 Mbp, 600 Mbp, 700 Mbp, 800 Mbp, 900 Mpb, 1000 Mbp.

As used herein, the phrase "plurality of polymerase enzymes," "plurality of polymerases" or grammatical variations thereof, refers the number of polymerase enzymes used for each respecting primer-prober used in the invention nucleic acid chain elongation reaction mixture. The quantity of polymerases in the "plurality of polymerase enzymes" can be selected from the group consisting of at least: 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 20000, 30000, 40000, 50000, 60000, 70000, 80000, 90000, 100000, 200000, 300000, 400000, 500000, 600000, 700000, 800000, 900000, and at least 1000000 polymerase enzymes per primer-probe used in the chain elongation reaction mixture. In other embodiments of continuously elongating a target nucleic acid template, the ratio of polymerase to template is selected from the group consisting of at least 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1, 1000:1, 10000:1, 20000:1, 30000:1, 40000:1, 50000:1, 60000:1, 70000:1, 80000:1, 90000:1, 100000:1, 200000:1, 300000:1, 400000:1, 500000:1, 600000:1, 700000:1, 800000:1, 900000:1, and at least 1000000:1 polymerase enzymes per primer-probe used in the chain elongation reaction mixture. The polymerases in the plurality can be a homogeneous collection of the same type of polymerase, or can be a heterogeneous collection of 2 or more different types of polymerases, e.g. 3, 4, 5, 6, 7, 8, 9, 10, 20, 30, 40, 50 up to 100 or more different polymerases in the plurality.

In some embodiments, the invention chain elongation reaction mixture has a plurality of target nucleic acid templates within a larger sample of template nucleic acids to be elongated therein. In particular embodiments, in addition to the detecting the presence of the interrogated target nucleic acid, the copy number of the target can be determined using calibration methods well known in the art. For example, control standards can be run of a known sequence with known copy numbers. The results of the invention nucleic acid detection reactions (e.g., LACES and/or FACES) can be compared to the control standard to determine the copy number of the target nucleic in the test sample.

Figure 9:
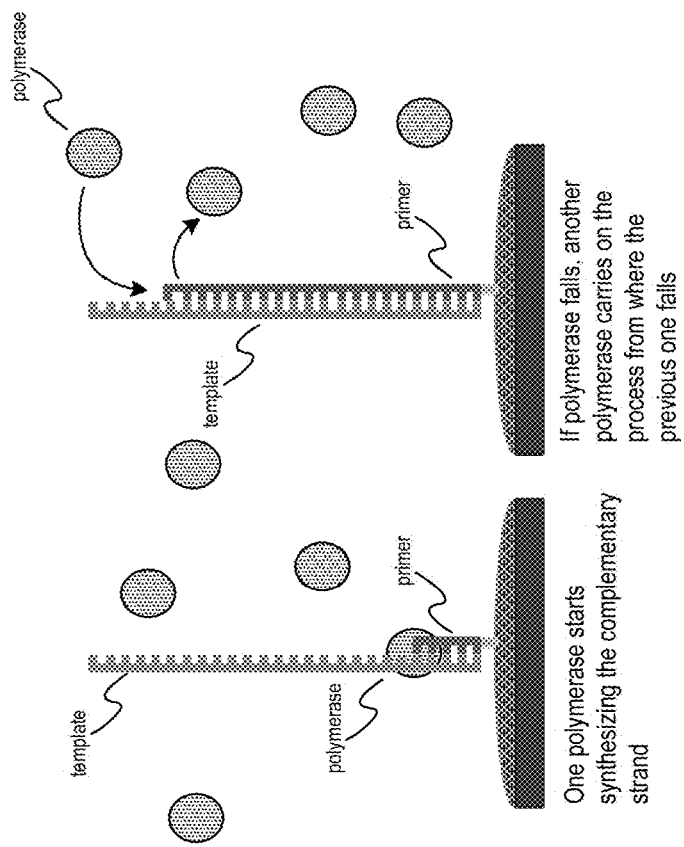
FIG. 9A shows an embodiment of conducting chain elongation in the invention LACES nucleic acid detection methods using a plurality of polymerases per single primer-probe on each respective target nucleic acid template.
FIG. 9B shows an embodiment where the chain elongation of the target nucleic acid template is substantially continuous because as the polymerase that starts synthesizing the complementary strand traverses its typical nucleic acid chain elongation length, then falls off or dissociates from template, another of the many other polymerases in the reaction mixture immediately binds to the template and continues the complementary strand chain elongation synthesis.
Figure 10:
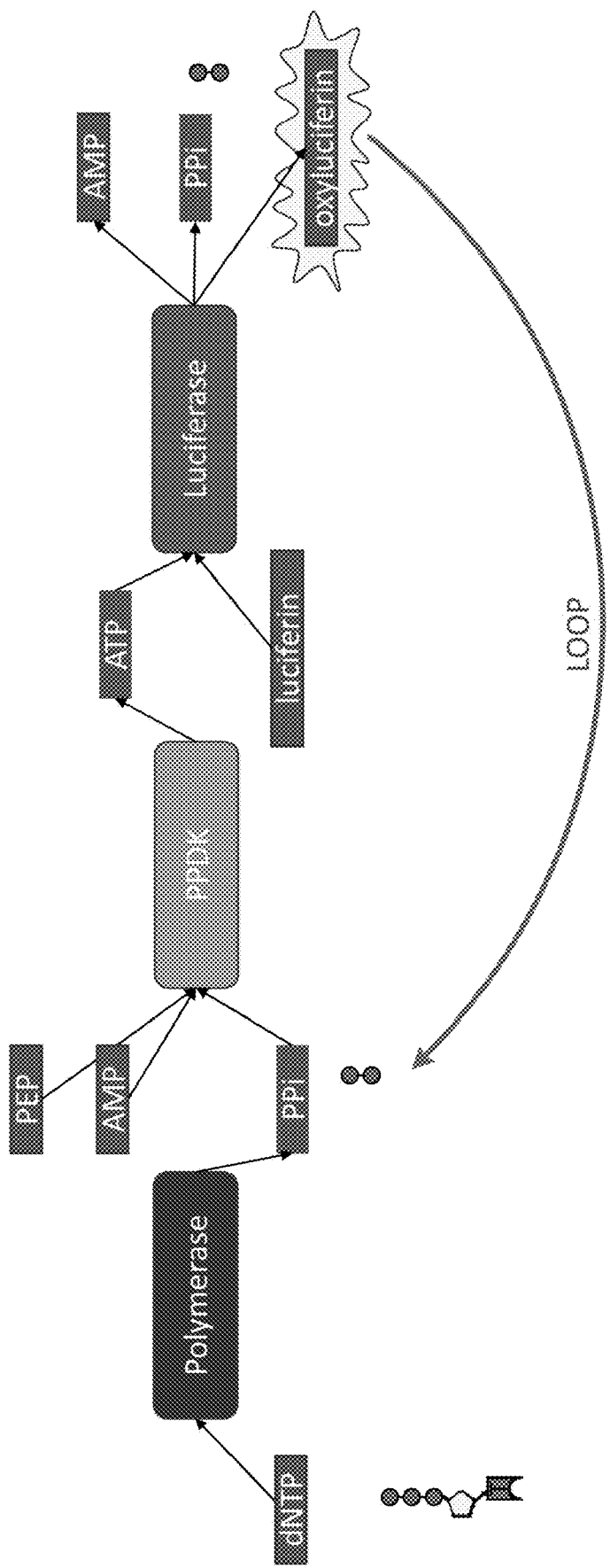
FIG. 10 shows another general illustration of an embodiment of the invention LACES target nucleic acid detection method employing AMP+PEP and the PPDK enzyme. The cleaved pyrophosphate is combined with AMP+PEP by interaction with PPDK enzyme, which binds the respective pyrophosphate to AMP, resulting in the formation ATP (ATP) for subsequent use in the luciferase reaction to generate detectable luminescence light, which is amplified by the enzymatic loop described herein.

In some embodiments of the invention nucleic acid target detection methods, the enzyme concatenate is provided in a particular individual confinement (e.g., a droplet, or the like), such that there can be as few as one up to a plurality of primer-probes in the confinement area, along with the test sample nucleic acid templates being interrogated; while there is a plurality (e.g., many) of polymerase enzymes and a corresponding plurality of the other enzymes forming the concatenate (FIG. 9A). In this embodiment, when a polymerase enzyme drops off (dissociates) from the target template nucleic acid (FIG. 9B), one of the many plurality of the other polymerases confined to the particular target nucleic acid template area, advantageously and relatively immediately commences its chain elongation at the location on the template where the previous polymerase left off or dissociated (FIG. 9B). In other words, the chain elongation occurs with a first polymerase enzyme until it gives way and dissociates from the template nucleic acid, then the chain elongation reaction continues with a second polymerase (different from the first) until it gives way and dissociates from the template nucleic acid, then the chain elongation reaction continues with a third polymerase (different from the second pol; which could be the first pol or another of the plurality of pols in the particular chain elongation reaction) until it gives way and dissociates from the template nucleic acid, and so on. Those of skill in the art will readily understand that using this approach, the target nucleic acid template is continuously being elongated, so long as the nucleic acid target detection reaction is being run. Those of skill in the art will also readily understand that when using the substantially continuous method of elongation disclosed herein, the nucleic acid chain elongation length is only limited by the length of the target nucleic and/or the physical size of the reaction confinement area used for the respective chain elongation reaction.

Accordingly, particular embodiments of the invention methods provided herein utilize a method of continuously chain elongating a target nucleic acid template. In this embodiment, as used herein "continuity," "continuously elongating a target nucleic acid template," or "substantially continuously elongating a target nucleic acid template," does not mean that a single polymerase is able to continuously elongate a particular target nucleic acids for the entire long nucleic acid chain elongation lengths, but rather means that the plurality of polymerase enzymes in the reaction area of the target nucleic acid template, taken together between them, are able to continuously elongate a particular target, by virtue of that plurality of polymerase enzymes continuously having numerous polymerases available to take over dNTP chain elongation at the next nucleotide from where the previous polymerase dissociated from the particular target nucleic acid template.

In particular embodiments of invention continuous nucleic acid chain elongation methods of detecting target nucleic acid sequences, especially where a plurality of polymerase are used to elongate each respective target template nucleic acid in a nucleic acid sample, the overall nucleic acid chain elongation length is only limited by the length of target template nucleic acid that is provided to a particular reaction confinement area. For example, the overall nucleic acid chain elongation lengths contemplated herein that can be achieved by using one or a plurality of polymerases for each single target nucleic acid template within the sample, are up to the lengths of entire chromosomes, e.g., 50 million up to about 300 million base pairs (e.g, 300 Mbp), and the like. In other certain embodiments contemplated herein, nucleic acid chain elongation lengths achieved by the invention chain elongation nucleic acid detection methods can be selected from the group consisting of at least: 200 bp, 300 bp, 400 bp, 500 bp, 600 bp, 700 bp, 800, bp, 900 bp, 1000 bp (i.e., 1 kbp), 5 kbp 10 kbp, 20 kbp, 30 kbp, 40 kbp, 50 kbp, 100 kbp, 200 kbp, 300 kbp, 400 kbp, 500 kbp, 600 kbp, 700 kbp, 800 kbp, 900 kbp, 1000 kbp (1 Mbp), 5 Mbp, 10 Mbp, 20 Mbp, 50 Mbp, 75 Mbp, 100 Mbp, 200 Mbp, 300 Mbp, 400 Mbp, 500 Mbp, 600 Mbp, 700 Mbp, 800 Mbp, 900 Mpb, 1000 Mbp.

Because of the substantially continuous elongation of the target template nucleic acid by plurality of polymerases, the reaction is not limited by a single enzyme's ability to achieve a particular nucleic acid chain elongation length. This permits the use of enzymes with higher specificity and low error rates in the invention methods. In accordance with particular embodiments of the invention methods of detecting target nucleic acids, it is contemplated herein that using more than one polymerase (i.e., a plurality) per primer-probe in the reaction mixture can achieve infinitely long nucleic acid chain elongation-lengths. As set forth herein, as one polymerase falls off the target template nucleic acid, another polymerase will continue from where the previous polymerase left off, which advantageously alters the way the polymerase can be selected or optimized to perform in the invention methods. For this reason, one of skill in the art can select a polymerase with a very low error rate, even though that polymerase may also have a relatively short nucleic acid chain elongation length. This provides an advantage for this particular embodiment, in that the polymerase selected for use in the invention methods does not require both long nucleic acid chain elongation length and specificity.

The template nucleic acids of the invention can also include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

As used herein, the phrase "nucleotide analog" refers to modified nucleotides that can be used in DNA synthesis (e.g., modified dNTPs such dATP, dTTP, dGTP, dCTP and dUTP). The nucleotide analogs for use in the invention can be any suitable nucleotide analog that is capable of being a substrate for the polymerase and for the selective cleaving activity. It has been shown that nucleotides can be modified and still used as substrates for polymerases and other enzymes. Where a variant of a nucleotide analog is contemplated, the compatibility of the nucleotide analog with the polymerase or with another enzyme activity such as exonuclease activity can be determined by activity assays. The carrying out of activity assays is straightforward and well known in the art.

The nucleotide analog can be, for example, a nucleoside polyphosphate having three or more phosphates in its polyphosphate chain with a label on the portion of the polyphosphate chain that is cleaved upon incorporation into the growing strand. The polyphosphate can be a pure polyphosphate, e.g. —O—PO3- or a pyrophosphate (e.g., PPi), or the polyphosphate can include substitutions. Additional details regarding analogs and methods of making such analogs can be found in U.S. Pat. Nos. 7,405,281; 9,464,107, and the like; incorporated herein by reference in its entirety for all purposes.

There are five types of dNTPs, namely deoxyadenosine triphosphate (dATP), deoxyguanosine triphosphate (dGTP), deoxycytidine triphosphate (dCTP), deoxythymidine triphosphate (dTTP), and deoxyuracil triphosphate (dUTP). Instead of dATP, dATPαS might be used as a substitute for the dATP as it acts as a substrate for DNA polymerase but not for luciferase. Other modified nucleotides contemplated for use herein are well-known in the art such as those described in Jordheim et al., Advances in the development of nucleoside and nucleotide analogues for cancer and viral diseases, Nat. Rev. Drug Discov. (2013) 12: 447-464; and Guo et al. Four-color DNA sequencing with 3'-O-modified nucleotide reversible terminators and chemically cleavable fluorescent dideoxynucleotides, Proc. Natl. Acad. Sci. U.S.A. (2008) 105:9145-9150, and the like (each of which are incorporated by reference herein in their entirety).

Other embodiments of the invention methods provided herein implement nucleotide analogs that are modified to improve the specificity to polymerase and reduce the affinity to the luciferase. An advantage of this embodiment results from avoiding a nonspecific interaction of nucleotides directly with luciferase, which can cause background luminescence production. For example, it is possible that deoxy adenosine triphosphate (dATP) or dGTP could be utilized by luciferase instead of ATP. Those of skill in the art can readily select a nucleotide analog including a modification to the nucleotide that reduces its affinity to luciferase while improving its specificity towards polymerase.

In yet other embodiments, dATPαS, dGTPαS, dCTPαS, dTTPαS are used in place of dATP, dGTP, dCTP and dTTP, which is contemplated herein to reduce the non-specific interaction of nucleotides with enzymes other than polymerase (e.g., luciferase).

Using the invention concatenated 3-Enzyme system and methods of Polymerase-ATP Sulfurylase-Luciferase provided herein, a luminescence signal indicating the presence of a particular interrogated target nucleic acid sequence will be generated only if the specific interrogating primer-probe binds its target sequence and initiates chain elongation, which will generate multiple pyrophosphate (PPi) leaving groups for use in the ATP-regenerating-enzymye/Luciferase Amplification loop.

As used herein, the phrase "leaving group" refers to the polyphosphate chain that is released from a respective dNTP when and/or upon cleavage by the invention 3 enzyme polymerase-ATP Sulfurylase-luciferase reaction during the incorporation of the respective dNTP into the template nucleic acid strand. In a particular embodiment herein, the polyphosphate is a pyrophosphate (PPi) that is cleaved from dNTP (FIGS. 1A and 1B), converted to ATP (ATP; FIGS. 1B and 1C) and then subsequently released into the reaction mixture via the luciferase reaction (FIG. 1C) for subsequent conversion back to the ATP via the reaction loop (see FIG. 1B, FIG. 1C, FIG. 2, FIG. 3 and FIG. 10). In other embodiments of the invention target nucleic acid sequence detection methods, the leaving group is a pyrophosphate with a fluorescent label attached (PPi+FL); see, e.g. FIGS. 11 and 12.

As set forth herein, this pyrophosphate (PPi) from FIG. 1C (or PPi+FL from FIGS. 11 and 12) can loop numerous times back to FIG. 1B in the ATP Sulfurylase/Luciferase Amplification Loop. The number of times pyrophosphate (PPi) can be looped back to amplify the respective luminescence signal for each dNTP incorporation event into the elongating sequence can be selected from the group consisting of at least: 5, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 20000, 30000, 40000, 50000, 60000, 70000, 80000, 90000, 100000, 200000, 300000, 400000, 500000, 600000, 700000, 800000, 900000, and at least 1000000 times.

The reaction conditions used can also influence the relative rates of the various reactions. Thus, controlling the reaction conditions can be useful in ensuring that the nucleic acid chain elongation reaction is successful at generating detectable light signal (e.g., luminescence and/or fluorescence) signal from the template at a high rate. The reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance the two slow-step behavior of polymerases is described in detail in U.S. Pat. No. 8,133,672, incorporated herein by reference.

Enzymatic reactions are often run in the presence of a buffer, which is used, in part, to control the pH of the reaction mixture. The type of buffer can in some cases influence the kinetics of the polymerase reaction in a way that can lead to two slow-step kinetics, when such kinetics are desired. For example, in some cases, use of IRIS as buffer is useful for obtaining a two slow-step reaction. Suitable buffers include, for example, TAPS (3-{[tris(hydroxymethyl)methyl]amino}propanesulfonic acid), Bicine (N,N-bis(2-hydroxyethyl)glycine), IRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some embodiments, the pH is between about 6.5 and about 8.0. In other embodiments, the pH is between about 6.5 and 7.5. In particular embodiments, the pH is selected from about 6.5, 6.6, 6.7, 6.8, 6.9, 7.0, 7.1, 7.2, 7.3, 7.4, or 7.5.

The temperature of the reaction can be adjusted to ensure that the relative rates of the reactions are occurring in the appropriate range. The reaction temperature may depend upon the type of polymerase or selective cleaving activity employed. The temperatures used herein are also contemplated to manipulate and control the hydrogen bonding between two bases as well as the bases' interaction with the water in the reaction mixture, thereby controlling the solubility of the reaction components.

In some embodiments, additives, such as magnesium, Coenzyme A, and the like, can be added to the reaction mixture that will influence the kinetics of the reaction. In some cases, the additives can interact with the active site of the enzyme, acting for example as competitive inhibitors. In some cases, additives can interact with portions of the enzyme away from the active site in a manner that will influence the kinetics of the reaction. Additives that can influence the kinetics include, for example, competitive but otherwise unreactive substrates or inhibitors in analytical reactions to modulate the rate of reaction as described in U.S. Pat. No. 8,252,911, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps. Added solvents can also affect, and in some cases slow, the translocation step. In some cases, the solvents act by influencing hydrogen bonding interactions.

The water miscible organic solvents that can be used to control the rates of one or more steps of the polymerase reaction in nucleotide chain elongation include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

Another aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interactions in polymerase reactions, see, for example, Arndt, et al., Biochemistry (2001) 40:5368-5375. Suitable conditions include those described in U.S. Pat. No. 8,257,954, incorporated herein by reference in its entirety for all purposes.

In a particular embodiment of the invention methods, the rate and fidelity of the polymerase reaction is controlled by adjusting the concentrations of the dNTP nucleotide analogs such that the polymerase operates in near ideal conditions in terms of parameters such as substrate concentration, amount of optical excitation, level of chemical modification. Therefore, the polymerase enzyme is contemplated herein to reach its maximum nucleic acid chain elongation-lengths, e.g., approximately in the tens of thousands of base pairs, similar to the DNA synthesis lengths achieved in natural settings.

In another embodiment, as set forth above, because the ATP enzyme (e.g., ATP sulfurylase) and polymerase rates can vary significantly depending on the type and source of the enzymes, the rate of ATP production by the ATP sulfurylase reaction employed herein can be adjusted separately by adjusting reaction conditions such as ATP sulfurylase concentration.

The invention includes systems for detecting and/or quantifying target nucleic acid sequences from a sample of nucleic acids. The systems provide for concurrently detecting and/or quantifying one or a plurality of target sequences from a plurality of nucleic acid templates within a nucleic acid sample being interrogated (e.g. cellular DNA, circulating DNA, and the like). The system can incorporate all of the reagents and methods described herein, and provides the instrumentation required for containing the sample, illuminating the sample with excitation light from the luminescence reactions, detecting light emitted from the sample during chain elongation to produce intensity versus time data from the luminescence detected by virtue of the pyrophosphate leaving groups (e.g, PPi) cleaved from the dNTP or dNTP analogs as the respective dNTPs are incorporated by the polymerase onto its cognate template nucleic acid; and thereby detecting and/or quantifying the presence of the target nucleic acid sequence.

As used herein, the phrase "detecting light" refers to well-known methods for detecting, for example, luminescence emitted from a luciferase reaction, fluorescence emitted from a fluorophore, and the like.

As use herein, the term "ATP regenerating enzyme/ Luciferase loop" or grammatical variations thereof (e.g., ATP Sulfurylase/Luciferase loop, AGPPase/Luciferase loop, PPDK/luciferase loop, and the like), refers to generally as an enzymatic loop between the ATP regenerating enzyme and luciferase (FIGS. 1A-1C and FIGS. 2 and 3), whereby following the luminescent reaction catalyzed by luciferase a new pyrophosphate molecule is released (PPi) (FIG. 1.C). This newly released PPi can once again be a substrate for the ATP regenerating enzyme (e.g., ATP Sulfurylase, AGPPase, PPDK, and the like) thereby generating an enzymatic loop between ATP regenerating enzyme (e.g., ATP Sulfurylase, AGPPase, PPDK, and the like) and luciferase (FIGS. 1B and 1C). As shown in FIG. 1B-1C, within this loop PPi is recycled by ATP Sulfurylase and converted into ATP (ATP), which can then be catalyzed by luciferase to generate a detectable luminescence signal, while releasing PPi again. This will generate successive signals from the pyrophosphate leaving group, and thereby serve as an amplification mechanism for the luciferase signal produced from the enzymatic incorporation of the most recent nucleotide.

In one embodiment, the system for detecting target nucleic acid sequences provided herein generally comprises a substrate having one or a plurality of single polymerase enzymes, a plurality of sample nucleic acid templates, and/or one or a plurality of primers (e.g., primer-probes) within, for example, a unique droplet, or the like. In particular embodiments, these reactions are uniquely confined such that their luminescence signals can be assigned to the respective nucleic acid target sequences as gene synthesis occurs. In other embodiments provided herein a plurality of polymerase enzymes are used with a single primer on the sample nucleic acid templates being interrogated, within, for example, a unique confinement, droplet, or the like. The chain elongation reagents generally include two or more types of nucleotide analogs, preferably four dNTPs or nucleotide analogs corresponding dATP, dTTP, dAGP and dCTP. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

The system comprises luminescence reagents (e.g., firefly luciferase and luciferin) for providing an illumination signal from the respective dNTPs as they are incorporated into the template strand and further undergo the ATP reaction (via ATP-sulfurylase) and luminescence reaction (e.g., firefly luciferase+luciferin) as set forth in FIGS. 1B-1C. The luminescence reaction provides a detectable illumination signal.

The system further comprises detection optics for observing signals from the detectable light signal (e.g., luminescence and/or fluorescence) corresponding to a respective dNTP incorporation event during the polymerase enzyme mediated addition to the template strand. In one embodiment, the detection optics observe a plurality of single molecule polymerase nucleic acid synthesis reactions concurrently, observing the luminescence signal of each nucleotide or nucleotide analog additions via the leaving group (e.g., pyrophosphate; PPi) that is used to form ATP in the invention concatenated 3 enzyme (Polymerase-ATP Sulfurylase-Luciferase) system. For each of the observed nucleic acid chain elongation reactions, the detection optics concurrently observe the signals from each of the PPi leaving groups that produce the respective luminescence reaction corresponding to a respective dNTP.

The system also comprises a computer configured to detect and/or quantify the observed signal from the luminescence reaction produced by the respective leaving group; whereby observed signals are used to detect and/or quantify the presence of the particular nucleic acid sequence being interrogated. The computer generally receives information regarding the observed signals from the detection optics in the form of signal data. The computer stores, processes, and interprets the signal data, using the signal data in order to detect and/or quantify the presence of the target nucleic acid sequence.

Optical detections systems which can be used with the present invention are described, for example in U.S. Pat. Nos. 8,802,424; 7,714,303; and 7,820,983, each of which are incorporated herein by reference in their entirety for all purposes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems, Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other nucleic acid detection specific formats; while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some embodiments of the methods and systems of the invention, optical confinements are used to enhance the ability to concurrently observe multiple target template polymerase chain elongation reactions simultaneously. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide detection or derive emitted radiation (e.g., luminescence, and the like) from only very small volumes. Examples of such optical confinements include systems that utilize, e.g., total internal reflection (TIR) based optical systems whereby light is directed through a transparent portion of the substrate at an angle that yields total internal reflection within the substrate.

In a particular embodiment, a preferred optical confinement is a micro-droplet (e.g., water-in-oil emulsion, and the like) which can contain an individual invention nucleic acid chain elongation reaction mixture for detecting target nucleic acid sequences, as set forth herein. For example, the nucleic acid chain elongation mixture reaction ingredients can be split in a way that each micro-droplet contains one polymerase-ATP Sulfurylase-luciferase set of enzymes and related reagents and one sample of template nucleic acids to be interrogated, whereby each signal detection unit is focused on a single micro-droplet. It is contemplated herein that each micro-droplet is a single nucleic acid target detection reaction cell containing individual polymerase-ATP Sulfurylase-luciferase 3 enzyme-system reactions. The micro-droplet reaction cell is also advantageously useful in the invention nucleic acid target sequence detection methods to act as micro-lenses to focus light on the respective signal detection unit.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or reaction components, for optical measurements.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements (e.g., reaction cells, micro-droplets, and the like) are provided in arrays of more than 100, more than 1000, more than 10,000, more than 100,000, or more than 1,000,000 separate reaction cells (such as a micro-droplet or the like) on a single substrate. In addition, the reaction cell arrays are typically comprised in a relatively high density on the surface of the substrate. Such high density typically includes reaction cells present at a density of greater than 10 reaction cells per $mm^2$, preferably, greater than 100 reaction cells per $mm^2$ of substrate surface area, and more preferably, greater than 500 or even 1000 reaction cells per $mm^2$ and in many cases up to or greater than 100,000 reaction cells per mm $mm^2$. Although in many cases, the reaction cells in the array are spaced in a regular pattern, e.g., in 2, 5, 10, 25, 50 or 100 or more rows and/or columns of regularly spaced reaction cells in a given array, in certain preferred cases, there are advantages to providing the organization of reaction cells in an array deviating from a standard row and/or column format. In preferred aspects, the substrates include as the particular reaction cell micro-droplets as the optical confinements to define the discrete chain elongation reaction regions on the substrate.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micromolar to millimolar because most of the enzymes have their Michaelis constants in these ranges. Accordingly, preferred array of optical confinements has an effective observation volume for detecting individual molecules present at a concentration higher than about 1 micromolar (uM), or more preferably higher than 50 uM, or even higher than 100 uM. In particular embodiments, typical microdroplet sizes range from 10 micrometers to 200 micrometers, and thus typical microdroplet volumes are around 5 picoliters to 20 nanoliters.

In the context of chemical or biochemical analyses within optical confinements, it is generally desirable to ensure that the reactions of interest are taking place within the optically interrogated portions of the confinement, at a minimum, and preferably such that only the reactions of a chain elongation reaction is occurring within an interrogated portion of an individual confinement (e.g., within a micro-droplet, or the like). A number of methods well-known in the art may generally be used to provide individual molecules within the observation volume. A variety of these are described in U.S. Pat. No. 7,763,423, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these. Also contemplated herein is the use of these dilution techniques for providing one, two, three or some other select number of LACES chain elongation reactions to fall within a given observation volume without being immobilized to a surface, such as would occur in the micro-droplet reaction cell contemplated herein for optical confinement. In a particular embodiment, the dilution techniques are utilized to provide a single invention method chain elongation reaction in a micro-droplet for use in the invention LACES chain elongation method.

The systems and methods of the inventions can result in improved target nucleic acid sequence determination by monitoring the signal from the PPi leaving groups of the nucleotide analogs after undergoing the 3 enzyme pol-ATP sulfurylase-luciferase set forth herein (e.g., a polyphosphate; PPi) using systems well-known in the art. In general, signal data is received by the processor. The information received by the processor can come directly from the detection optics, or the signal from the detection optics can be treated by other processors before being received by the processor. A number of initial calibration operations may be applied. Some of these initial calibration steps may be performed just once at the beginning of a run or on a more continuous basis during the run. These initial calibration steps can include such things as centroid determination, alignment, gridding, drift correction, initial background subtraction, noise parameter adjustment, frame-rate adjustment, etc. Some of these initial calibration steps, such as binning, may involve communication from the processor back to the detector/camera, as discussed further below.

Generally, some type of spectral trace determination, spectral trace extraction, or spectral filters are applied to the initial signal data. Some or all of these filtration steps may optionally be carried out at a later point in the process, e.g., after the pulse identification step. The spectral trace extraction/spectral filters may include a number of noise reduction and other filters as is well-known in the art. Spectral trace determination is performed at this stage for many of the example systems discussed herein because the initial signal data received are the light levels, or photon counts, captured by a series of adjacent pixel detectors. For example, in one example system, pixels (or intensity levels) from positions are captured for an individual wave-guide at each frame. Light of different frequencies or spectrum will fall on more than one of the positions and there is generally some overlap and possibly substantial overlap. According to specific embodiments of the invention, spectral trace extraction may be performed using various type of analyses, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR (signal to noise ratio) and therefore pulse detection when extracted spectral traces are analyzed for pulses somewhat separately. In further embodiments, a method according to the invention may analyze the multiple captured pixel data using a statistical model such as a Hidden Markov Model.

Whether the luminescence signal from the leaving groups (e.g., pyrophosphates; PPi) entering the ATP-regenerating-enzyme/Luciferase Amplification Loop reaction can be categorized as a significant signal pulse or event is determined. In some example systems, because of the small number of photons available for detection and because of the speed of detection, various statistical analysis techniques may be performed in determining whether a significant pulse has been detected.

If the signal is identified as a significant pulse or signal event, a further optional spectral profile comparison may be performed to verify the spectral assignment. This spectral profile comparison is optional in embodiments where spectral traces are determined prior to or during pulse identification. In order to make this determination, the signals coming from the channel corresponding to the leaving group (e.g., pyrophosphates; PPi) are used to assess whether a pulse from a luminescence signal corresponds to an incorporation event.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In particular embodiments, for detecting low numbers of photons from single molecules, the use of a photomultiplier tube (PMT) and/or a photon counter unit is contemplated for use in the invention methods. In either event, signal data used according to specific embodiments of the invention generally include both intensity level information and spectral information. In the context of separate detector elements, such spectral information will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals. The spectral data may be obtained from the image data that is extracted from the detector, or alternatively, the derivation of spectral data may occur on the detector such that spectral data will be extracted from the detector.

For the target nucleic acid sequence detection methods described above, there may be a certain amount of optical signal that is detected by the detection system that is not the result of a signal from an incorporation event. Such signal will represent "noise" in the system, and may derive from a number of sources that may be internal to the monitored reaction, internal to the detection system and/or external to all of the above. The practice of the present invention advantageously reduces these overall sources of noise typically present in prior art methods.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods well-known in the art, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse-based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event. As will be appreciated, the basis for calling a particular signal event as a significant pulse, and ultimately as an incorporation event, will be subject to a certain amount of error, based upon a variety of parameters as generally set forth herein. One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data.

Target Enrichment by Electrical Modulation (TEEM)

Figure 19:
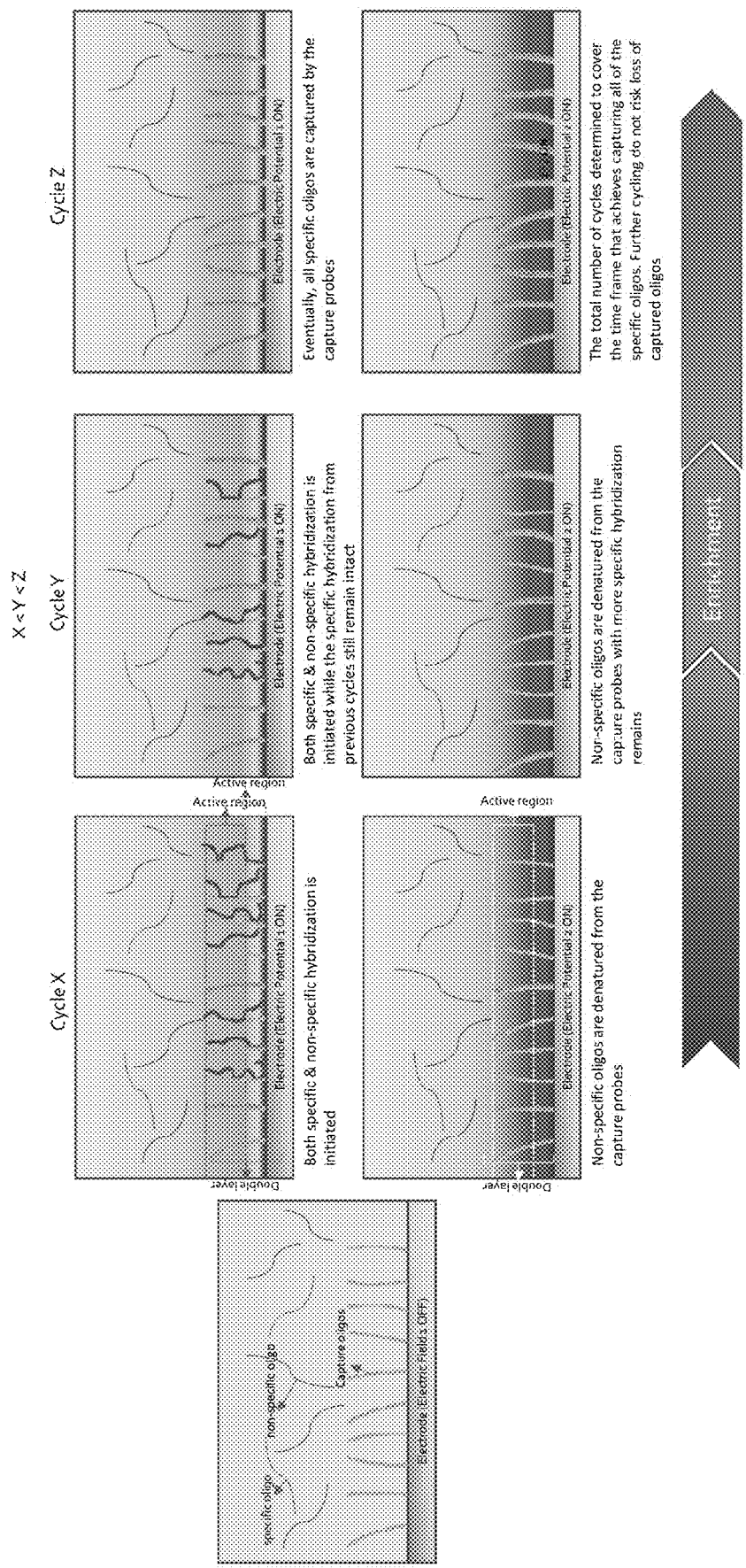
FIG. 19 shows an overall depiction of the invention Target Enrichment By Electrical Modulation (TEEM) method that utilizes surface attached capture-probes that lay in the interface at the active region, where pH distribution is manipulated by voltage- and electric field-modulation.

Also provided herein are methods for enriching or isolating a target-nucleic acid from a nucleic acid-containing sample, said method comprising:

a. receiving an electrolytic fluid solution including ions and a nucleic acid-containing sample in a fluid chamber having a first and second electrode, wherein at least one electrode has attached thereto a plurality of capture-probes complementary to the target-nucleic acid (depicted in FIGS. 13-19), wherein the capture-probes are at the electrode-solution interface;

b. applying an annealing-voltage to the electrolytic fluid in proximity to the electrode-solution interface to generate an annealing-pH level by the electrode-solution interface (Cycle X, Y and Z, top panels of FIG. 19), wherein the annealing-pH level causes annealing of any number of complementary base pairs between nucleic acid within the nucleic acid-containing sample and the capture-probes;

c. applying a denaturing-voltage to the electrolytic fluid in proximity to the electrode-solution interface to generate a denaturing-pH level by the electrode-surface interface (Cycle X, Y and Z, bottom panels of FIG. 19), wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and d. modulating voltages between the annealing-voltage and denaturing-voltage, wherein after the final application of the corresponding pH level (e.g., annealing or denaturing), the target-nucleic acid is enriched or isolated from the nucleic acid-containing sample by remaining bound to the capture-probe on the electrode (Cycle Z, bottom panel of FIG. 19).

There are two main factors that directly affect the binding kinetics of nucleic acids (RNA and DNA) in solution: Temperature and pH. Thus far in the prior art, temperature has been the only factor utilized in genomics. In accordance with the present invention, the invention TEEM method replaces the conventional prior art temperature-based approach with electric fields and movement of ions in solutions. This advantageously provides a quantum leap in reducing the time frame of nucleic acid handling in genomics assays by several orders of magnitude.

As used herein, the phrase "enriched or isolated from the nucleic acid-containing sample" refers to the physical separation of the desired target-nucleic acid from the other nucleic acids in the nucleic acid-containing sample (see, e.g., Cycle Z, bottom panel of FIG. 19, and the like). For the first time, electrical manipulation of DNA hybridization and denaturation is utilized to enrich, isolate and/or separate a target-nucleic acid from other nucleic acid in a nucleic acid-containing sample. In accordance with the present invention, the modulation of voltages, electric fields and corresponding pH levels permits the precise capture of the desired target-nucleic, while permitting the non-target nucleic acid within the sample to be washed away prior to any detection analysis is conducted.

The invention TEEM method utilizes the unique manipulation of Electric Double Layer to generate precise pH levels at precise points in the solution. For example, when an electrode is brought in contact with a solid or liquid ionic conductor (electrolyte) and an electric potential is applied to the electrode, counterions move towards the electrode while co-ions are repelled from the surface (see FIG. 18). This generates an ion distribution, and thus a pH distribution or gradient, (see the boxed green shaded region labeled pH Gradient in FIG. 18; and the boxed shaded regions in the Cycle X panels of FIG. 19) at the electrode-solution interface. This permits the generation of precise pH levels at precise points in the solution, thus causing either hybridization (i.e., annealing; and the green shaded boxed region of the Cycle X top panel of FIG. 19) or denaturation the blue shaded boxed region of the Cycle X bottom panel of FIG. 19) of a very specific number of nucleic acid base pairs. Such precise control is not possible with temperature.

As set forth herein, a positive charge distribution (of positive ions of the electrolytic fluid) is at a maximum at the electrode that is negatively charged, which positive charge decreases with increased distance away on the spatial dimension from the applied negative charge at the electrode. Also for example, the positive charge distribution can be formed by an accumulation of hydronium ($H_3O+$) ions, and in some examples magnesium ($Mg^{2+}$) ions, that forms an electrical double layer at the negatively charged electrode, thereby creating an acidic pH environment in the regions of the double layer proximate the negatively charged electrode. Likewise, the negative charge distribution can be formed by an accumulation of hydroxyl ($OH-$) ions that forms an electrical double layer at a positively charged electrode, thereby creating a basic pH environment in the regions of the double layer proximate the positively charged electrode.

The invention TEEM nucleic acid enrichment methods provided herein include modulating ion distributions in solutions through modulating the electric fields, where the time to complete a cycle can be on the order of microseconds to other sub-second durations, e.g., depending on the conductivity, ion diffusion rates, charge of ions and voltage applied. In accordance with the present invention, the applied net charges are modulate or alternated (e.g., modulating both a net negative charge and a net positive applied on the electrode), so that the ionic charge distribution (i.e., pH level) is likewise modulated or alternated.

The invention TEEM method utilizes surface attached capture-probes (FIGS. 13-16) that lay in the interface at the active "double layer" region, where pH distribution is manipulated by modulating the applied voltage/electric field. All nucleic acids within the sample periodically enter the double-layer region of the fluid chamber via Brownian motion. There are at least two pH distributions generated in active double layer region; an annealing-pH level (Cycle X, Y and Z, top panels of FIG. 19) and a denaturing-pH level (Cycle X, Y and Z, bottom panels of FIG. 19). In a particular embodiment, the annealing-pH level enables hybridization of any number of complementary base pairs. Whereas the denaturing-pH level, enables only a number (or a range) of base pairs over a particular threshold number (or range) to hybridize or remain hybridized, while denaturing a number of complementary base pairs lower than the threshold. By modulating the electric field applied in at particular frequencies, and therefor modulating the pH levels between denaturing-pH levels and annealing-pH levels, the target-nucleic acids that have entered the double-layer region having precisely controlled respective pH-levels (either an annealing-pH level or denaturing-pH level), bind and remain bound to the capture-probe while undesired nucleic acids (e.g., non-target nucleic acids) do not bind to, or are denatured from the capture-probes. In one embodiment, each cycle takes about a second (e.g., 1 kH) and the total enrichment, isolation and/or separation process is completed in about 50 cycles.

An advantage of the invention TEEM methods is that it renders non-specific primer binding to the target-nucleic acid nonexistent, null or negligible. This in turn advantageously results very little to no background noise in the invention target-nucleic acid detection methods, in particular when used in combination with the invention LACES methods for detecting target-nucleic acids provided herein. Another advantage provided by the invention TEEM method is that there is no requirement for an independent signal that perfect target-nucleic acid (e.g., SARS-COV2, and the like) hybridization has been achieved. Once the target-nucleic acid enriched or isolated it can be detected by any means known in the art; or by the invention LACES method provided herein. In particular embodiments, after the target nucleic acid is enriched and/or isolated from the material not bound to the capture-probe (also referred to herein as a capture-primer probe), the nucleic acid-containing sample is washed away prior to detection.

As used herein, in the context of the enriching or isolating the target-nucleic using the invention TEEM method, the phrase "target-nucleic acid is detected" refers to employing any of the well-known techniques for detecting the presence of a particular nucleic acid. Following the capture of the target-nucleotide, exemplary methods for detecting the presence of the target-nucleic acid include a method selected from the group consisting of: LACES, direct detection, PCR (including, but not limited to, 5'-nuclease real-time PCR), rolling circle amplification, combinations of ligation and PCR, and amplification followed by a detection step, labelled probes, intercalating fluorescent dye, and the like.

Other suitable detection systems for detecting target-nucleic acid, include, but are not limited to, scanning electron microscopy, near field scanning optical microscopy (NSOM), total internal reflection fluorescence microscopy (TIRFM), and the like. For example, guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, 2nd Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; and Drmanac, International patent publication WO 2004/076683.

Figure 20:
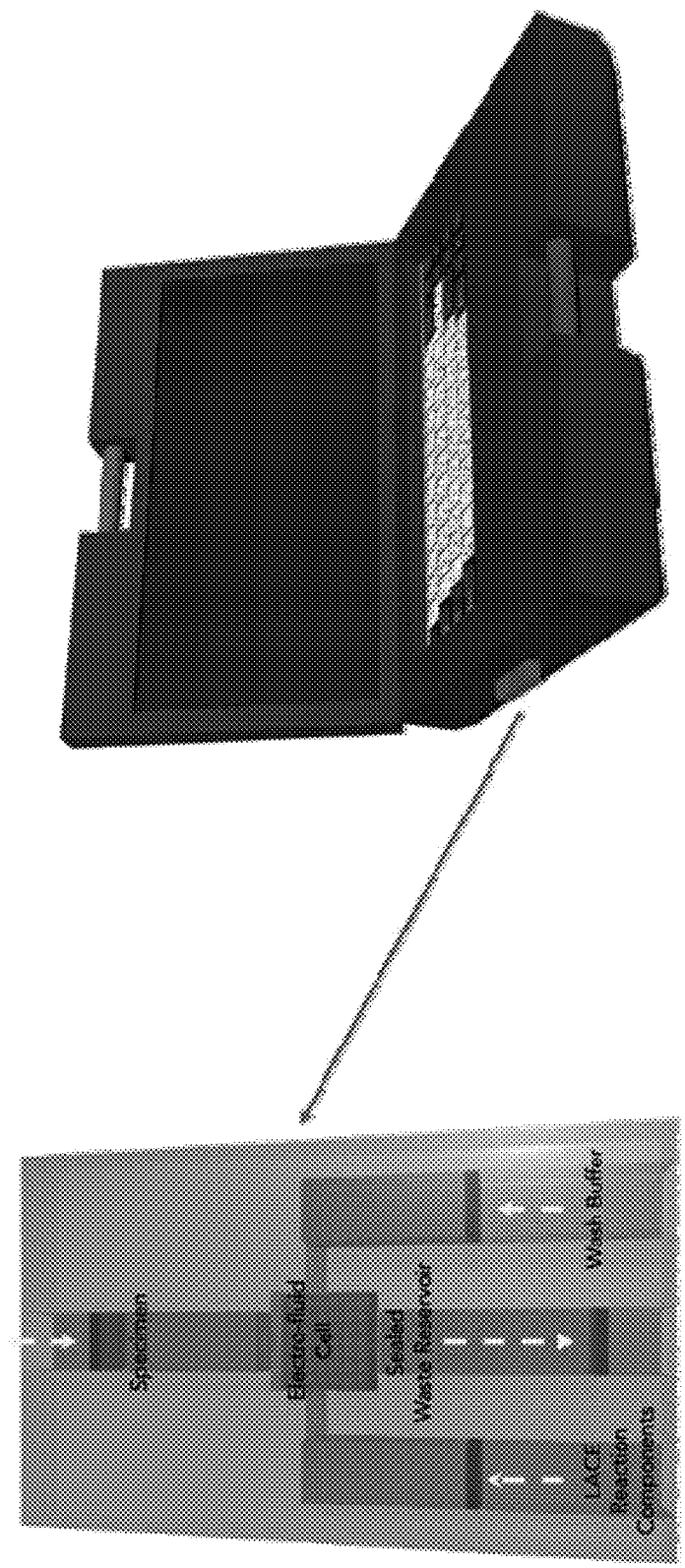
FIG. 20 shows an invention portable instrument-based diagnostic system for detection of pathogens having an exemplary single-use-cartridge including all reagents and components necessary for carrying out the invention TEEM and LACES methods to detect the presence or absence of a target-nucleic acid.

In particular embodiments, the invention device instruments (e.g., a single-use-cartridge shown in FIG. 20) for use employing the invention methods to detect target-nucleic acid, comprise three basic components: (i) a fluidics system for storing and transferring sample, detection and processing reagents, e.g. probes, wash solutions, and the like, to an array; (ii) a reaction fluid chamber, or flow cell, holding or comprising an array and having flow-through and electric potential (voltage) control capability; and (iii) an illumination and detection system (e.g., a single-use-cartridge in combination with portable device shown in FIG. 20). In one embodiment, a fluid chamber or flow cell has a voltage control subsystem with ability to modulate voltage.

As use herein, the phrase "nucleic acid-containing sample" can be any physical material that contains nucleic acid therein. Exemplary "nucleic acid-containing samples include: cells, saliva, urine, blood, hair, semen, saliva, bone, tissue teeth, cell-lysates, viruses, cellular-DNA, genomic DNA, and the like. In particular embodiments, the nucleic acid-containing sample can be isolated or obtained by dielectrophoresis. For example, cellular DNA, genomic DNA, viral nucleic acid or total-nucleic acid can be isolated or obtained by dielectrophoresis of a cell-lysate.

The invention method includes a step to receive an electrolytic fluid in a fluid chamber. As used herein, the phrase "fluid chamber" refers to an enclosed structure that can house any of the solution mixture described herein, e.g., the electrolytic fluid, elongation mixture, and the like. In particular embodiments, the fluid chamber can include an interior surface formed of an electrically insulative material and having one or more electrodes. As used herein, the phrase "electrolytic fluid" refers to an ionic solution that can include one or more of the following: ions, e.g., including H+, OH— and Mg2+ among others, and template nucleic acid chain-elongation reagents, e.g., including primer-probes, polymerase enzymes, nucleotides, and one or more double-stranded nucleic acid molecules. The invention TEEM method includes a step of applying or modulating an electric field (via applied voltage) across the electrodes of the fluid chamber containing the electrolytic fluid to generate modulated pH levels (e.g., denaturing-pH levels and annealing-pH levels) of the electrolytic fluid that both denatures double-stranded nucleic acids and anneals single-stranded nucleic acids.

As used herein, the term "electrode" refers to the well-known conductor through which electricity enters or leaves an object, substance, or region. An electrode is generally used to make contact with a nonmetallic part of a circuit. As is well-known in the art, for an electronic macro-scale circuit there needs to be two polarities, thus two electrodes. In particular embodiments of the invention methods and chips/oligonucleotide arrays provided herein, the second electrode can be ground. In other embodiments, at least one electrode (e.g., the first electrode) or both electrodes can have the capture probes and/or primers attached thereto. For example, in one embodiment, a positive electrode might generate a low pH at the active region and at the negative electrode that might correspond to a high pH at the active "double-layer" region. It has been found that the denaturing and hybridization based on pH levels work substantially symmetrically; namely, to achieve denaturation of double-stranded nucleic acids, you can apply both lower pH levels and higher pH levels.

As used herein, the phrase "electrode-solution interface" refers to the location where the solution (e.g., electrolytic fluid) comes in contact one or more of the electrodes within the fluid chamber.

Figure 18:
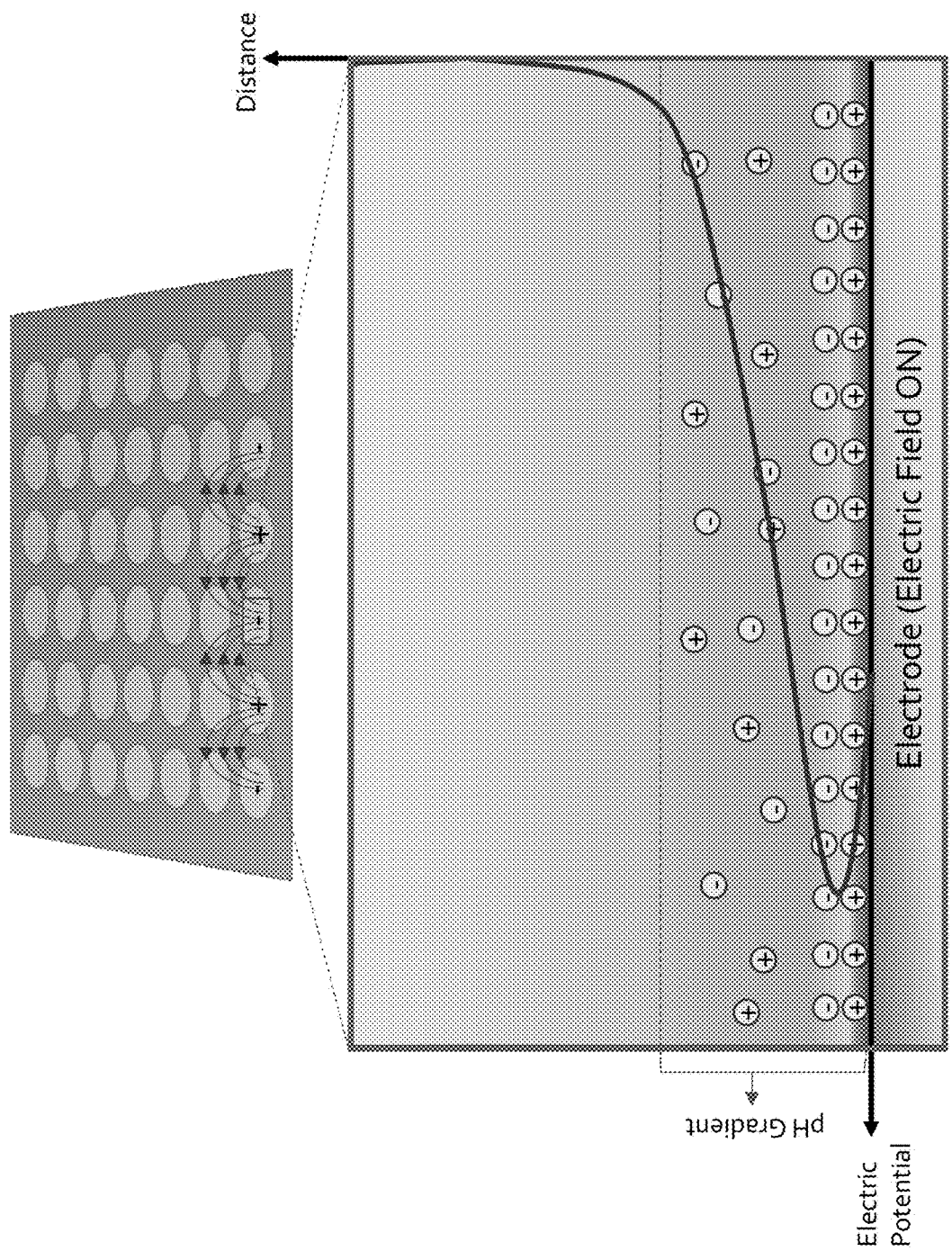
FIG. 18 shows the Manipulation of the Electric Double Layer. When an electrode is brought in contact with a solid or liquid ionic conductor (electrolyte) and an electric potential is applied to the electrode, counter-ions move towards the electrode while co-ions are repelled from the surface, which generates an ion, thus pH, distribution at the electrode-solution interface.

As used herein, the phrase "in proximity to the electrode-solution interface" refers to the region of the electrolytic fluid that is relatively near the electrode-solution interface (see the boxed darker shaded region labeled pH Gradient in FIG. 18). The applied electric fields create a "double-layer" spatial ion distribution in the electrolytic fluid including a first layer of first ions electrically attracted to an oppositely-charged electrode and a second layer of second ions electrically attracted to the first layer. The ion distribution depends on the dimensions and geometry of the electrodes, and applied voltage on the electrodes (e.g., magnitude of the electric field), and ion concentrations in the electrolytic fluid. In some embodiments, for example, the invention method can include a process to select and/or adjust the magnitude and duration of the applied denaturing and annealing electric field. In some embodiments, a DC electric field can be generated by applying a DC voltage across the electrodes. In other embodiments, an AC electric field may be applied, e.g., which can also include a DC bias. For example, the spatial distribution of charge can be produced and controlled by manipulating the "double layer" in the electrolytic solution (e.g., electrolytic fluid solution) using the applied external denaturing and annealing electric fields, providing the respective field-controlled annealing-pH level and denaturing-pH level. In other embodiments, a variety of electric field patterns (DC or AC, based on different waveforms, frequencies, amplitudes) and sequences can be generated to affect the binding kinetics of two or more strands.

The "double layer" refers to two parallel layers, e.g., the first and second layers, surrounding the surface of an object when it is placed into a liquid (depicted as a row of negative ions layered on top of positive ions in FIG. 18). The first layer (Stem layer) includes a surface charge that is either positive or negative and is formed by ions adsorbed directly onto the object, e.g., either a positive or negative electrode in the invention TEEM methods. The second layer (diffuse layer) is composed of ions attracted to the surface in order to electrically screen the first layer. The diffuse layer is made up of free ions loosely associated with the object (e.g., electrodes). The double layer can extend up to micrometers depending on the ion concentration of the solution and the charge (or voltage applied) on the surface. It is the region within the electrolytic fluid solution where the denaturing-pH levels and annealing-pH levels are created by respective denaturing and annealing voltages and electric fields (see the boxed darker shaded region labeled pH Gradient in FIG. 18).

In particular embodiments the capture-probes (or capture/primer-probes) are positioned at the electrode-solution interface. As use herein, the phrase "capture-probe" refers to a single-stranded or partially single-stranded nucleotide that can bind the respective target-nucleic acid of interest (depicted as red and green regions in FIGS. 13-16). The capture-probe lengths can be 5-500 or more nucleotides in length; or in other embodiments can be 5-400, 5-300, 5-200, 5-150, 5-100, 5-90, 5-80, 5-70, 5-60, 5-50, 5-40, 5-30, 5-25, 5-20, 5-15, 10-500, 10-400, 10-300, 10-200, 10-150, 10-100, 10-90, 10-80, 10-70, 10-60, 10-50, 10-40, 10-30, 10-25, 10-20, 10-15, 15-500, 15-400, 15-300, 15-200, 15-150, 15-100, 15-90, 15-80, 15-70, 15-60, 15-50, 15-40, 15-30, 15-25, 15-20, 20-500, 20-400, 20-300, 20-200, 20-150, 20-100, 20-90, 20-80, 20-70, 20-60, 20-50, 20-40, 20-30, 20-25, 25-500, 25-400, 25-300, 25-200, 25-150, 25-100, 25-90, 25-80, 25-70, 25-60, 25-50, 25-40, or 25-30 nucleotides in length. In particular embodiments, the capture probe also functions as a primer, referred to herein as a "capture/primer probe," in nucleic acid chain elongation reactions, such as those carried out in the invention LACES methods provided herein.

Figure 13:
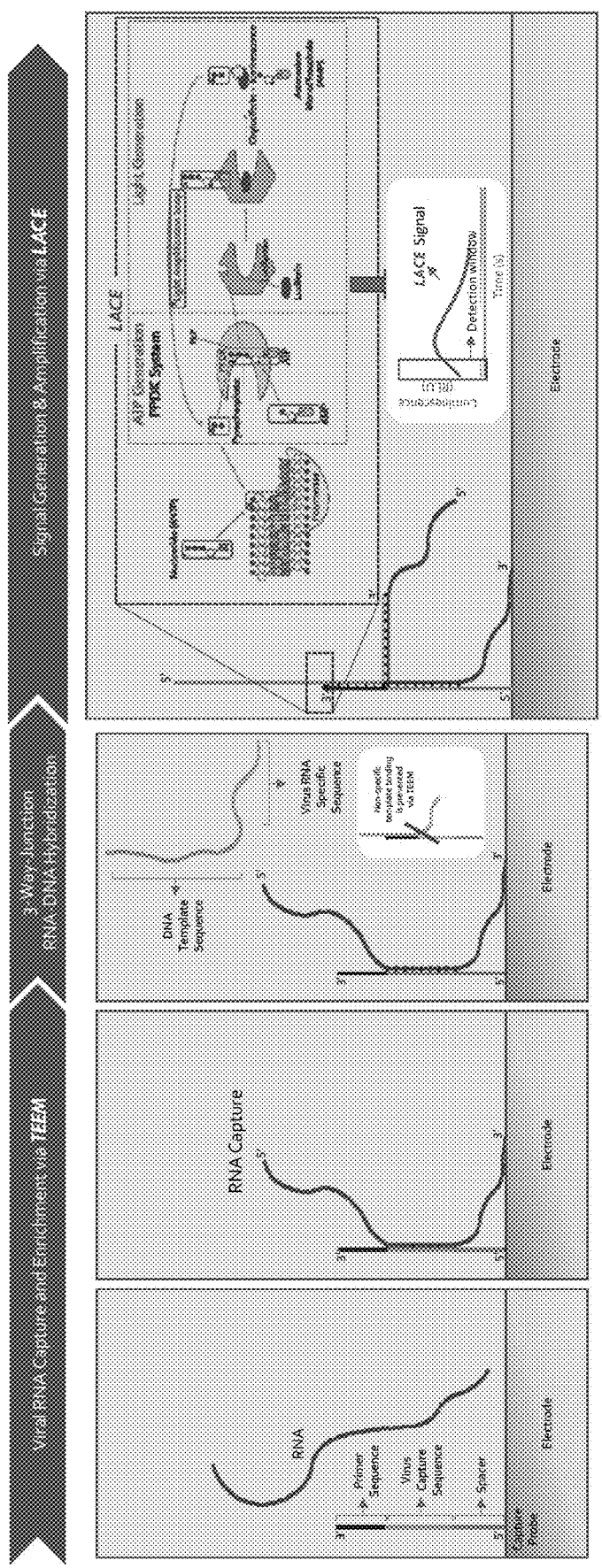
FIG. 13 shows a general illustration of an embodiment of the invention using a bi-functional capture/primer probe to capture an RNA target-nucleic acid; and a 3-way-junction DNA intermediate nucleic acid in an invention LACES chain elongation reaction using Polymerase to elongate from the intermediate DNA template-strand that is bound to both the RNA-target-nucleic acid and the primer region of the bi-functional capture/primer-probe, to detect the RNA target-nucleic acid (e.g., SARS-COV2). The LACE reaction, depicted in the last panel, generates a signal that peaks within a few minutes and decays slowly. The detection occurs within the first minute during the rapid rise in signal.
Figure 14:
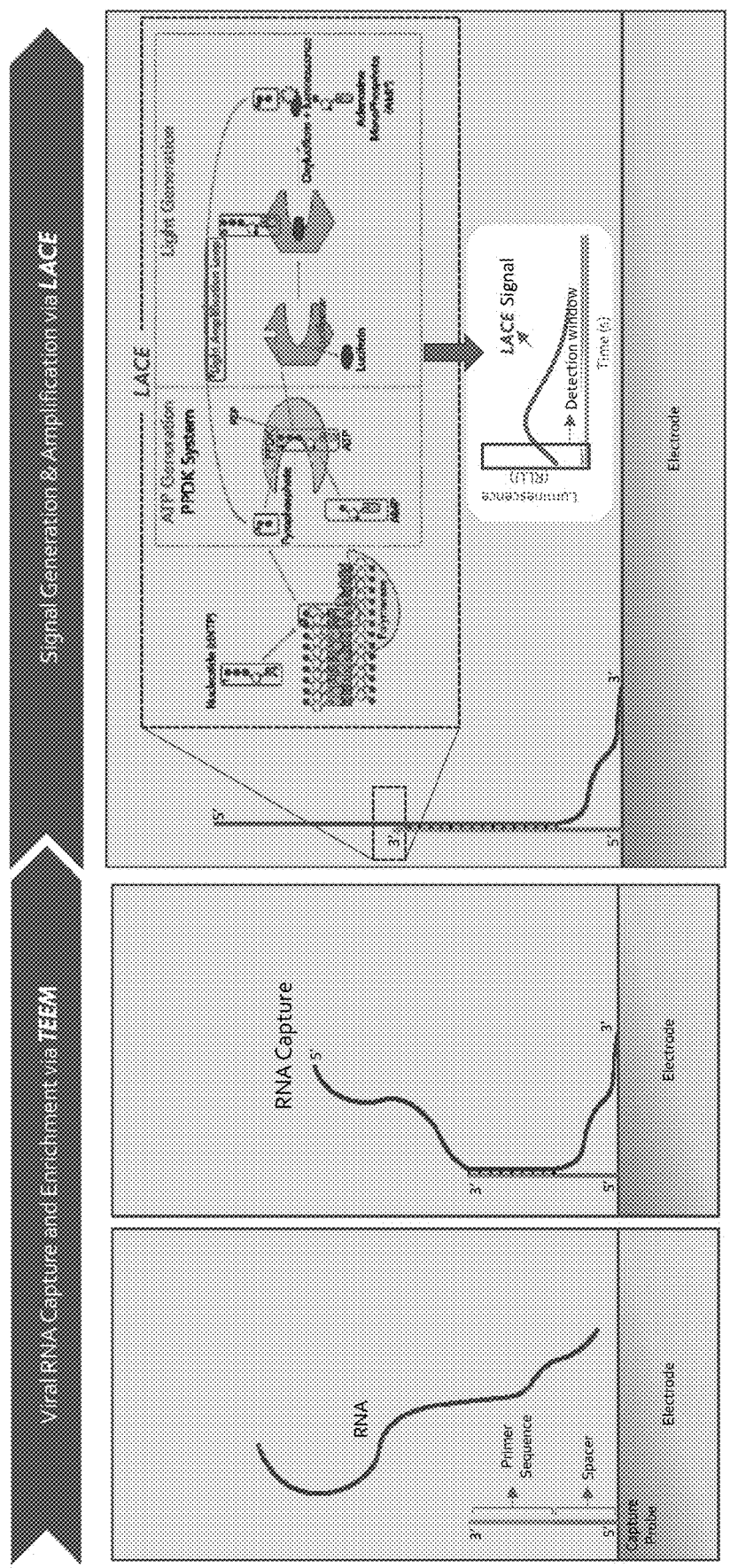
FIG. 14 shows a general illustration of an embodiment of the invention using a capture/primer probe to capture an RNA target-nucleic acid using the invention TEEM methods provided herein; and using the DNA capture/primer-probe as the primer (DNA/RNA) in an invention LACES chain elongation reaction using Polymerase(s) to elongate from the template-target-RNA strand(s) to detect the RNA target-nucleic acid (e.g., SARS-COV2). The LACES reaction, depicted in the last panel, generates a signal that peaks within a few minutes and decays slowly. The detection occurs within the first minute during the rapid rise in signal.
Figure 15:
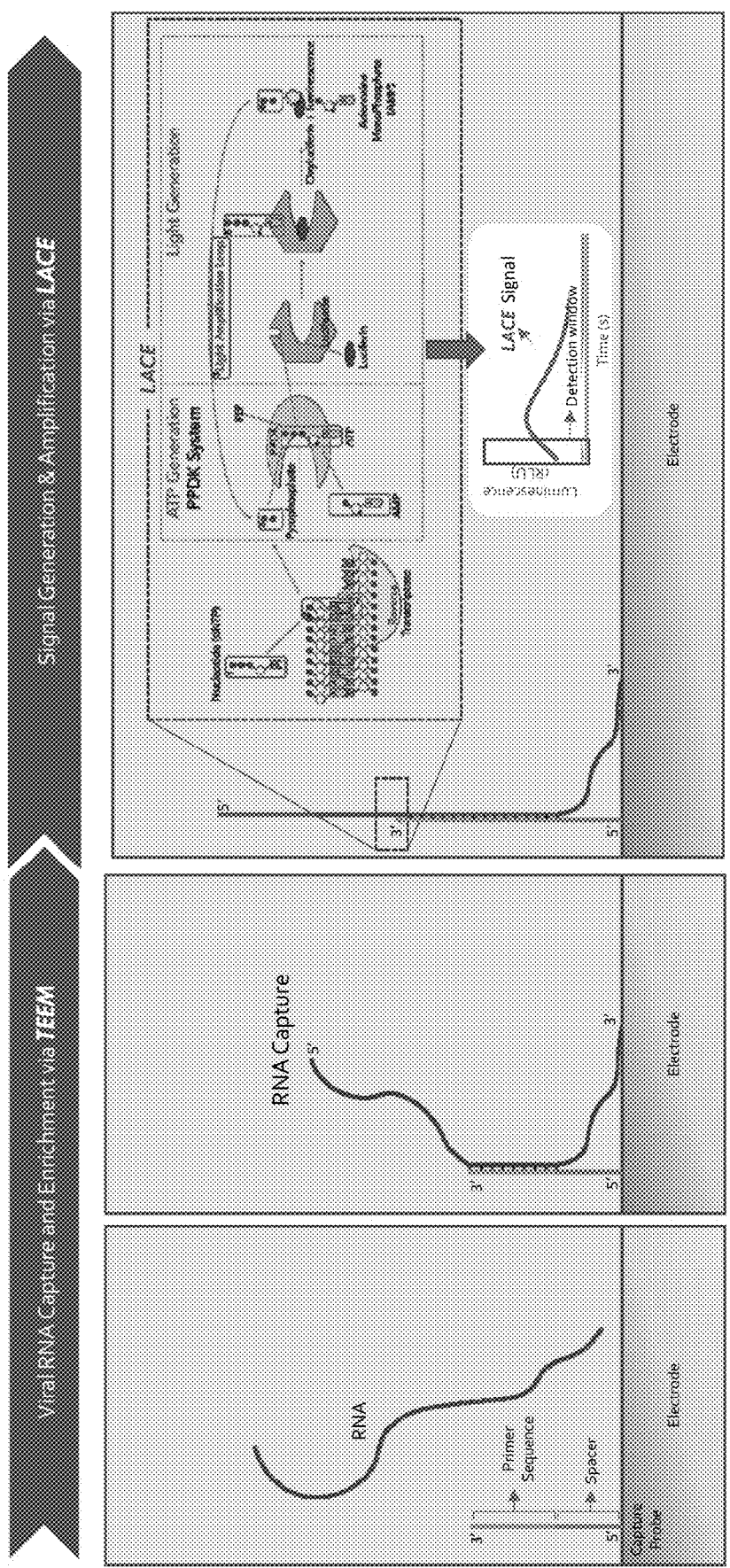
FIG. 15 shows a general illustration of an embodiment of the invention using a capture/primer probe to capture an RNA target-nucleic acid; and using the DNA capture/primer-probe as the primer (DNA/RNA) in an invention LACES chain elongation reaction using Reverse Transcriptase to elongate from the template-target-RNA strand to detect the RNA target-nucleic acid (e.g., SARS-COV2). The LACE reaction, depicted in the last panel, generates a signal that peaks within a few minutes and decays slowly. The detection occurs within the first minute during the rapid rise in signal.
Figure 16:
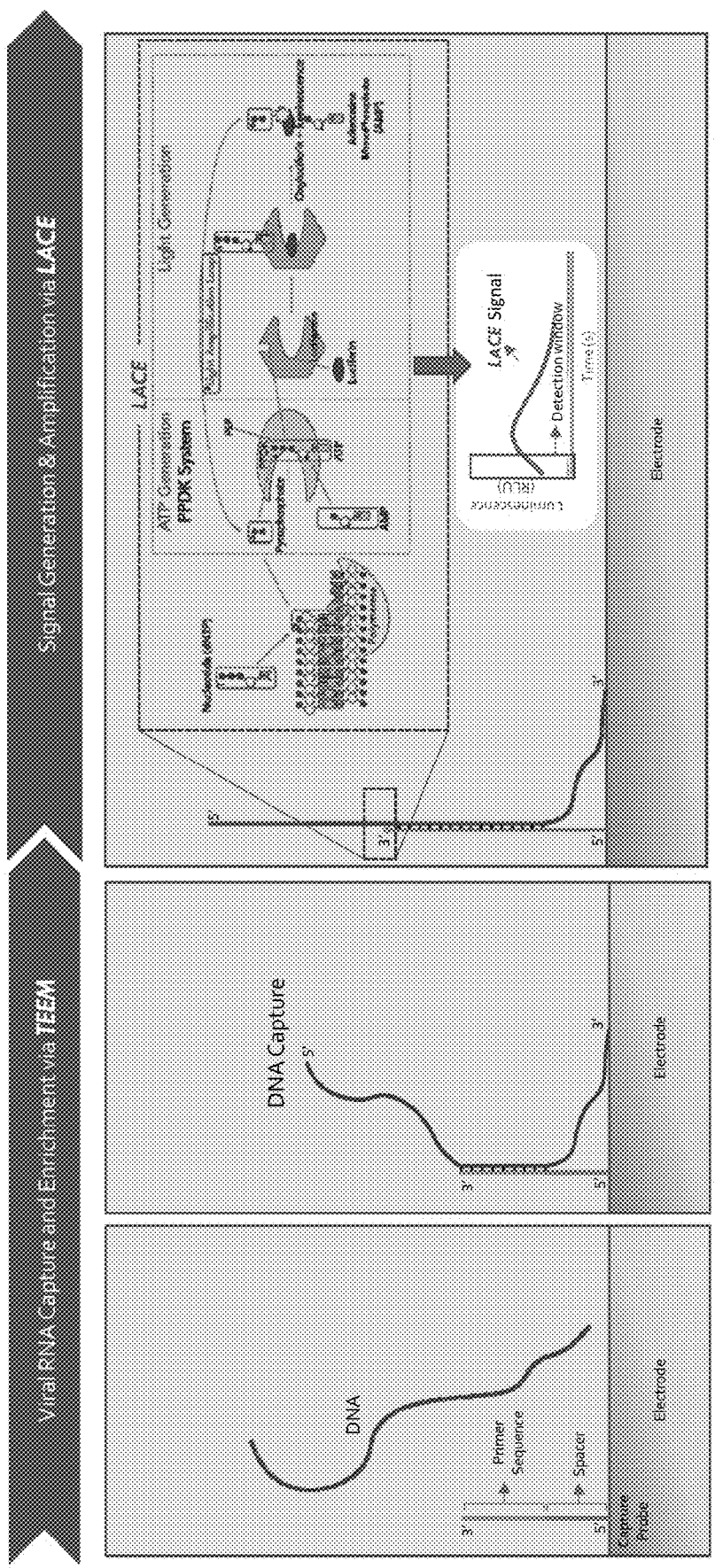
FIG. 16 shows a general illustration of an embodiment of the invention using a capture/primer probe to capture a DNA target-nucleic acid; and using the DNA capture/primer-probe as the primer (DNA/DNA) in an invention LACES chain elongation reaction using Polymerase to elongate from the template-target-DNA strand to detect the DNA target-nucleic acid. The LACE reaction, depicted in the last panel, generates a signal that peaks within a few minutes and decays slowly. The detection occurs within the first minute during the rapid rise in signal.

As used herein, the phrase "capture/primer-probe" refers to a single-stranded or partially single-stranded nucleotide that has a region that can bind the respective target-nucleic acid of interest; and also serve as a primer to initiate a nucleic acid chain elongation reaction on the respective target-nucleic acid template (depicted as the green region of the capture-probe in each of FIGS. 14-16). In other embodiments, the capture/primer probe can have a region that can bind the respective target-nucleic acid of interest (green region of capture/primer-probe of FIG. 13); and also contain a region that serves as a primer to initiate a nucleic acid chain elongation reaction on the respective target-nucleic acid template (depicted as dark blue region of capture/primer-probe of FIG. 13). The capture/primer-probe lengths can be 5-500 or more nucleotides in length; or in other embodiments can be 5-400, 5-300, 5-200, 5-150, 5-100, 5-90, 5-80, 5-70, 5-60, 5-50, 5-40, 5-30, 5-25, 5-20, 5-15, 10-500, 10-400, 10-300, 10-200, 10-150, 10-100, 10-90, 10-80, 10-70, 10-60, 10-50, 10-40, 10-30, 10-25, 10-20, 10-15, 15-500, 15-400, 15-300, 15-200, 15-150, 15-100, 15-90, 15-80, 15-70, 15-60, 15-50, 15-40, 15-30, 15-25, 15-20, 20-500, 20-400, 20-300, 20-200, 20-150, 20-100, 20-90, 20-80, 20-70, 20-60, 20-50, 20-40, 20-30, 20-25, 25-500, 25-400, 25-300, 25-200, 25-150, 25-100, 25-90, 25-80, 25-70, 25-60, 25-50, 25-40, or 25-30 nucleotides in length.

As used herein, the phrase "a plurality of capture-probes" or "plurality of capture/primer-probes" refers to more than one probe. The plurality of probes can be in the form of an oligonucleotide array on any substrate, such as an electrode, chip surface, or the like. Although a planar array surface is utilized in a particular embodiment, the capture-probe oligonucleotide array may be fabricated on a surface of virtually any shape or on a multiplicity of surfaces, including electrodes. The capture and capture/primer probes are designed and constructed to be complementary to the particular target-nucleic acid being interrogated. In particular embodiments where the capture probes are on a surface (e.g., an electrode, and the like), the density of capture-probes or capture-primer probes on the surface (e.g., electrode) is in the range of about 100 to about 1,000,000 oligonucleotide probes per $cm^2$.

Those of skill in the art will recognize that a single oligonucleotide probe can function as a primer-probe, capture-probe and/or a capture/primer-probe depending on for which invention method it is being used.

As used herein, the phrase "density of capture-probes" or "density of capture/primer-probes" refers to the number of probes on the respective electrode surface. In some embodiments, the density of probes is quantified by the number of oligonucleotide per $cm^2$. In a particular embodiments, the array of oligonucleotide capture-probes or capture/primer probes on the respective electrode is a high density array comprising density selected from greater than about 100, 1,000, 2,000, 3,000, 4,000, 5,000, 6,000, 7,000, 8,000, 9,000, 10,000, 15,000, 20,000, 30,000, 40,000, 50,000, 60,000, 70,000, 80,000, 90,000, 100,000, 150,000, 200,000, 250,000, 300,000, 400,000, 500,000, 600,000, 700,000, 800, 000, 900,000 or 1,000,000 oligonucleotide probes per $cm^2$.

In other embodiments, the density is selected such that the capture of the target-nucleic acids is completed within a certain upper limit of time, such as with 180 s, 160 s, 140 s, 120 s, 110 s, 100 s, 90 s, 80 s, 70 s, 60 s, 50 s, 40 s, 30 s, 25 s, 20 s, 15 s, 14 s, 13 s, 12 s, 11 s, 10 s, 9 s, 8 s, 7 s, 6 s, 5 s, 5 s, 3 s, 2 s, and 1 s.

For example, depending on the respective physical size of the fluid chamber and/or the electrode surface, the density of probes can be such that the expected target-nucleic acids are captured in less than 500 seconds, 400 seconds, 300 seconds, 200 seconds, 180 seconds, 120 seconds, 100 seconds, 90 seconds, 80 seconds, 70 seconds, 60 seconds, 50 seconds, 40 seconds, 30 seconds, 25, seconds, 20 seconds, 15 seconds, 10 seconds, 9 seconds, 8 seconds, 7 second, 6 seconds, 5 seconds, 4 seconds, 3 seconds, 2 seconds and 1 second.

As used herein, the phrases "modulating," "modulating voltages," "modulating electric current" or grammatical variations thereof, when used in the context of the voltage (electric current) applied in the invention methods, refers to alternating between at least 2 different voltages in the invention methods provided herein (e.g., between the annealing-voltage and denaturing-voltage), to permit both the denaturation and annealing of double-stranded base pairs. The voltages applied generate an electric field close to (or in proximity to) the electrode and electrolytic fluid solution interface, referred to herein as the "electrode-solution interface." The particular electric fields generated cause migration of ions in solution, which in turn results in a respective pH level in proximity to the electrode-solution interface that favors or causes the nucleic acid to either anneal or denature, depending on the particular voltage applied.

Thus, for each denaturing-voltage, there is a corresponding respective denaturing-electric field and a corresponding denaturing-pH level. Likewise, for each annealing-voltage, there is a corresponding respective annealing-electric field and a corresponding annealing-pH level. In particular embodiments, the annealing-voltages applied generate an annealing-electric field and an annealing-pH level, which in turn promotes annealing of complementary nucleic acids into double-strands. The denaturing-voltage applied generates a denaturing-electric field and denaturing-pH level that promotes denaturing of complementary nucleic acids into single-strands. Accordingly, the alternating voltages applied and the corresponding modulated electric fields generated, create at least 2 different pH levels in the invention methods provided herein (e.g., an annealing-pH level and denaturing-pH level).

As used herein, the phrase "annealing-voltage," refers to the voltage that promotes or causes annealing of complementary single-stranded nucleic acids into double-strands in the particular electrolytic fluid solution. The annealing-voltages applied generate a corresponding annealing-electric field and an annealing-pH level, which in turn promotes or causes annealing of complementary single-stranded nucleic acids into double-strands.

As used herein, the phrase "annealing-pH level" refers to the pH level that promotes or causes annealing of complementary nucleic acids into double-strands in the particular electrolytic fluid solution. In particular embodiments, the respective annealing-pH levels are generated via migration of ions in solution in response to the particular annealing-electric-field applied to the electrolytic fluid solution.

As used herein, the phrase "annealing of any number of complementary base pairs between nucleic acid within the nucleic acid-containing sample and the capture-probes" refers to a range of pH level conditions that promote or cause the annealing of single-stranded nucleic acids of particular lengths, or permit double-strand nucleic acids to remain double-stranded.

As used herein, the phrase "denaturing-voltage" refers to the voltage that promotes or causes denaturation of complementary double-stranded nucleic acids into single-strands in the particular electrolytic fluid solution. The denaturing-voltages applied generate a corresponding denaturing-electric field and a denaturing-pH level, which in turn promotes or causes denaturation (or separation) of complementary double-stranded nucleic acids into single-strands.

As used herein, the phrase "denaturing-pH level" refers to the pH level that promotes or causes denaturation of complementary double-stranded nucleic acids into single-strands in the particular electrolytic fluid solution. In particular embodiments, the respective denaturing-pH levels are generated via migration of ions in solution in response to the particular denaturing-electric-field applied to the electrolytic fluid solution.

As used herein, the phrases "denaturation of double-stranded nucleic acids that are shorter than a double-stranded capture-probe" or "denaturation of double-stranded nucleic acids, including hybridized pairs of capture probes and target-nucleic acids, that are either a particular number of base pairs shorter or a particular range of base pairs shorter than the full-length of a double-stranded capture-probe" refers to a range of pH level conditions that promote or cause the denaturation of double-stranded nucleic acid of particular lengths, so long as the length of the double-strand denatured is shorter than a full-length double-stranded capture-probe or capture/primer-probe. In one embodiment, the lengths of double-stranded nucleic acids that are denatured are 1-100 base pairs shorter than a double-stranded capture-probe, which corresponds to "a particular range of base pairs shorter" than the full-length of a double-stranded capture probe. In certain embodiments, the particular denaturing-voltage, denaturing-electric field and denaturing-pH level applied does not need to denature an exact number of base pair lengths fewer than the primer-probe. In these embodiments, it can be a range of base pair lengths denatured that is fewer than the full-length double-stranded primer-probe referred to herein as "a particular range of base pairs shorter than the full-length of a double-stranded capture-probe." The reason for this is that for longer primer-probe lengths, e.g. 15, 20, 25, 30, 40, 50 nucleotide or higher in length, that are specifically complementary to the respective target sequence being assayed, the statistical probability that other non-target sequences will have even 5, 10, 15, 20 or higher, nucleotides in common with the primer-probe is extremely low, such that the denaturing-voltage in the probe-target enrichment modulation step can be the voltage amount that dentures (via the corresponding pH level) a double-stranded nucleic acid that is at least 5, 10, 15, 20, 25, 30, 25, 40, 45, 50 base pairs or more, shorter than a fully hybridized primer-probe, depending on the length of the respective capture/primer-probe selected. In other words, the statistical probability that a non-target-nucleic acid would have 11 or more complementary base pair matches with the capture-probe or capture/primer-probe is so small that it is negligible. Accordingly, in particular embodiments, the upper threshold of denaturing-voltages contemplated for use herein can be a voltage that denatures in the range of 1-5, 1-10, 1-15 base pairs, for capture-probes or capture/primer probes that are about 20 oligonucleotides or longer. In this embodiment, for capture-probes or capture/primer-probes that are about 25 oligonucleotides or longer, a voltage that denatures in the range of 1-20 base pairs can be used.

In other embodiments for example, if the capture/primer-probe length is 20 nucleotides, the electric field/voltage threshold can be set at a level that denatures any double-stranded nucleic acid that is less than about 10-15 base pairs in length, such that the specificity of target-nucleic acid capture is substantially higher than if there were no modulation of the denaturing-voltage (e.g., second pH level) and the annealing-voltage (e.g., first pH level). In this embodiment, the full-length of a double-stranded capture-probe, primer probe, or capture/primer-probe is 20 base pairs.

In other embodiments of the invention TEEM nucleic acid enrichment or isolation methods, the denaturing-pH level causes the denaturation of double-stranded nucleic acid having a number of complementary base pairs corresponding to a range selected from: 1 to x-5 complementary base pairs; 1 to x-10; 1 to x-15 complementary base pairs; 1 to x-20 complementary base pairs; 1 to x-25 complementary base pairs; 1 to x-30 complementary base pairs; 1 to x-35 complementary base pairs; 1 to x-40 complementary base pairs; 1 to x-245 complementary base pairs; 1 to x-50 complementary base pairs, where x is the nucleotide length of the respective capture-probe In other exemplary embodiments where a 25 nucleotide primer-probe is used, the voltage/electric field applied can be selected, for example, to denature a 1-20, 1-15, 1-10, or 1-5 range of base pair double-strands, while permitting the 25 base pair full-length double-stranded primer-probe to remain hybridized. In this embodiment, the full-length of a double-stranded capture-probe, primer probe, or capture/primer-probe is 25 base pairs. As another example, in an embodiment where a 20 nucleotide primer-probe is used, the energy/voltage applied can be selected, e.g., for example to denature a 1-15, 1-10, or 1-5 range of base pair double-strands, while permitting the 20 base pair double-stranded primer-probe to remain hybridized. In an embodiment where a 50 nucleotide primer-probe is used, the energy/voltage applied can be selected, e.g., for example to denature a 1-40, 1-30, 1-20, or 1-10 range of base pair double-strands, while permitting 50 base pair double-strands to remain hybridized.

Accordingly, in other embodiments, the denaturing-voltage selected can be an amount that denatures double-stranded nucleic acid (via the pH level generated) in the range of nucleotides less than the length of the capture-probe or primer-probes, selected from: 5-100, 5-90, 5-80, 5-70, 5-60, 5-50, 5-40, 5-30, 5-20, 5-15, 5-10, 10-100, 10-90, 10-80, 10-70, 10-60, 10-50, 10-40, 10-30, 10-20, 10-15, 2-50, 2-40, 2-30, 2-20, 2-15, 2-10, 2-5, 3-50, 3-40, 3-30, 3-20, 3-15, 3-10, 3-5, 4-50, 4-40, 4-30, 4-20, 4-15, and 4-10 nucleotides less.

In other particular embodiments, especially where the capture primer-probe lengths are at or above about 20 nucleotides the energy/voltage/electric field applied during the primer-probe enrichment step, can be selected such that any double-stranded base pairing that is in the range of 5 bp-10 bp, 10 bp-15 bp, 15 bp-20 bp, 20 bp-25 bp, or the like, less than the respective capture primer-probe length will be denatured.

In other embodiments, the energy/voltage/electric field applied during the primer-probe modulated denaturing step can be selected such that any range of double-stranded base pairing starting from as low as 1 bp less than the respective capture primer-probe length will be denatured. For example, in an embodiment where a 25 nucleotide primer-probe is used, the energy/voltage applied will denature 24 base pair double-strands, while permitting 25 base pair double-strands to remain hybridized. As another example, in an embodiment where a 20 nucleotide primer-probe is used, the energy/voltage applied will denature 19 and less base pair double-strands, while permitting 20 base pair double-strands to remain hybridized. In an embodiment where a 50 nucleotide primer-probe is used, the energy/voltage applied will denature 49 and less base pair double-strands, while permitting 50 base pair double-strands to remain hybridized. In an embodiment where a 40 nucleotide primer-probe is used, the energy/voltage applied will denature any base pair double-strands less than the range from 20-30 base pair double-strands.

In embodiments where longer primer-probes are utilized (e.g., 20 nucleotides or higher), the denaturing-voltage selected can be an amount that denatures double-stranded nucleic acid more than 1 bp less than the respective capture primer-probe length. For example, the denaturing-voltages used to melt/denature hybridized double-stranded nucleic acid can be voltage amounts that denture double-strands that are 2, 3, 4, 5, 6, 7, 8, 9, 10, 11, 12, 13, 14, 15, 16, 17, 18, 19, 20, 25, 30, 35, 40, 45, 50, or more bp less than the respective capture primer-probe length.

In particular embodiments, the total number of cycles of modulated electric field during the enrichment or isolation is in the range of $1\times10^2$-$1\times10^{12}$ total cycles; $1\times10^3$-$1\times10^9$ total cycles; $1\times10^3$-$1\times10^8$ total cycles; $1\times10^3$-$1\times10^7$ total cycles; $1\times10^3$-$1\times10^6$ total cycles, and the like. To correlate the times and frequencies utilized in invention TEEM methods, 1,000 total cycles corresponds to a modulated electric field frequency of 0.2 kHz for 5 seconds; 0.1 kHz for 10 seconds; 0.0666 kHz for 15 seconds; or 0.05 kHz for 20 seconds; whereas 1 billion total cycles corresponds to 200 MHz for 5 seconds; 100 MHz for 10 seconds; 66.6 MHz for 15 seconds; or 50 MHz for 20 seconds.

Accordingly, the frequencies contemplated herein for modulating the electric fields are in the range of 0.1 kHz to 200 GHz. In other embodiments, frequency ranges contemplated for use herein include 0.1 kHz to 200 GHz; 0.1 kHz to 100 GHz; 0.1 kHz to 1 GHz; 0.1 kHz to 100 MHz; 0.1 kHz to 10 MHz; 0.1 kHz to 1 MHz; 0.1 kHz to 900 kHz; 0.1 kHz to 800 kHz; 0.1 kHz to 700 kHz; 0.1 kHz to 600 kHz; 0.1 kHz to 500 kHz; 0.1 kHz to 400 kHz; 0.1 kHz to 300 kHz; 0.1 kHz to 200 kHz; 0.1 kHz to 100 kHz; and the like. In yet another embodiment, the modulating voltages between the annealing-voltage and denaturing-voltage is at a modulation frequency in the range of 0.1-1000 Khz (e.g., 100-1,000,000 cycles per second).

The total time in seconds for the step of modulating the electric field (and thus modulating the solution ph levels near the electrode) is in the range of 1 to 500 sec; 1 to 400 sec; 1 to 300 sec; 1 to 200 sec; 1 to 100 sec; 1 to 90 sec; 1 to 80 sec; 1 to 70 sec; 1 to 60 sec; 1 to 50 sec; 1 to 40 sec; 1 to 30 sec; 1 to 25 sec; 1 to 20 sec; 1 to 15 sec; and 1 to 10 sec. Other ranges of time contemplated herein for modulating the electric field are 5 to 500 sec; 5 to 400 sec; 5 to 300 sec; 5 to 200 sec; 5 to 100 sec; 5 to 90 sec; 5 to 80 sec; 5 to 70 sec; 5 to 60 sec; 5 to 50 sec; 5 to 40 sec; 5 to 30 sec; 5 to 25 sec; 5 to 20 sec; and 5 to 15 sec. Accordingly, those of skill in the art will understand that the modulation frequency of the electric field can be varied depending on the total number of cycles desired within a particular time for the respective embodiment.

As used herein, the phrase "final application of the corresponding pH level" (e.g., annealing- or denaturing-pH level), refers to the final cycle of the modulation of the electric field; and thus the final cycle of the annealing and denaturing of the nucleic acids onto or from, respectively, the capture-probe. Once the modulation of the electric field and respective pH levels has ceased, only the target-nucleic acid will remain bound to the capture-probe or capture/primer-probe.

As used herein, the phrase "remaining bound to the capture-probe" refers to the target-nucleic acid maintaining its hybridized state to the capture-probe sequence while the denaturing-voltages, -electric fields, and -pH levels are applied to the reaction mixture to denature and remove non-target nucleic acid from the capture-probes.

TEEM+LACES

In a particular embodiment of the invention TEEM methods, the invention methods of enriching or isolating target-nucleic acids are used in combination with the invention LACES methods for detecting the presence of target-nucleic acids. Accordingly, also provided herein are methods for detecting the presence of a target-nucleic acid sequence in a nucleic acid-containing sample comprising:

a. receiving an electrolytic fluid solution including ions and a nucleic acid-containing sample in a fluid chamber having a first and second electrode, wherein at least one electrode has attached thereto a plurality of capture/ primer-probes complementary to the target-nucleic acid, wherein the capture/primer-probes are at the electrode-solution interface;

b. applying an annealing-voltage to the electrolytic fluid in proximity to the electrode-solution interface to generate an annealing-pH level by the interface, wherein the annealing-pH level causes annealing of any number of complementary base pairs between nucleic acid within the nucleic acid-containing sample and the capture/primer-probes;

c. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and d. modulating the annealing-voltage and denaturing-voltage, wherein after the final application of the corresponding pH level (e.g., annealing or denaturing), the target-nucleic acid is enriched or isolated from the nucleic acid-containing sample by remaining bound to the capture/primer-probe on the electrode (e.g., the first electrode), wherein the bound target-nucleic acid is a template strand for template directed elongation synthesis;

e. providing an elongation mixture comprising (i) a polymerase enzyme, (ii) an ATP regenerating enzyme, (iii) a luminescence enzyme (e.g., firefly luciferase), and (iv) a polymerase-ATP regenerating enzyme-luminescence reagent solution having the components for carrying out template directed elongation synthesis of a growing nucleic acid strand, wherein said reagent solution includes an ATP-regenerating-enzyme-substrate, a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;

f. carrying out nucleic acid elongation synthesis such that one or a plurality of nucleotide analogs are added sequentially to the template strand if the capture/primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme yielding ATP, then c) binding the ATP to a luminescence-enzyme, wherein a luminescence-substrate is catalyzed by the luminescence-enzyme to produce luminescence while regenerating the respective leaving group; and g. detecting light from the luminescence while nucleic acid synthesis is occurring, whereby detection of light indicates the presence of the particular target nucleic acid sequence. In a particular embodiment, material not bound to the capture/primer-probe from the nucleic acid-containing sample is washed away prior to providing an elongation reaction mixture of step (e).

In a particular embodiment (as set forth in FIG. 13), the capture/primer-probe (depicted in red, green and blue in all panels of FIG. 13), which is attached to the electrode via a spacer sequence (red portion of capture probe), comprises an RNA-capture-probe virus capture sequence (green region) capable of binding an RNA-target-nucleic acid sequence. In this embodiment, the capture/primer-probe further comprises, 3' to the RNA-capture probe region, a primer-sequence (dark blue region) capable of initiating a nucleic acid-chain elongation reaction from a nucleic acid template strand (e.g., a DNA template strand). In this embodiment, the primer-sequence (dark blue region) of the capture-primer probe is complementary to an artificial junction-DNA Template Strand set forth in the $3^{rd}$ panel. More particularly, the primer-sequence of the capture-primer probe is complementary to an artificial DNA sequence region (light blue region of DNA Template Sequence in the $3^{rd}$ panel of FIG. 13) that is 5' to an artificial DNA sequence region (green region of DNA Template Sequence in the $3^{rd}$ panel of FIG. 13) that is complementary to the portion/region of the RNA-target-nucleic acid sequence that is adjacent (either upstream or downstream and/or immediately adjacent in some embodiments) to the region of the RNA-target-nucleic acid sequence that binds the capture-probe sequence.

In this embodiment, to initiate the LACES chain-elongation reaction, the RNA-target nucleic acid is captured from the sample by the capture-probe region (green region) of the capture/primer-probe; the adjacent region of the captured RNA-target nucleic acid in turn binds/captures the artificial junction-DNA template strand (at the green region of the DNA Template Strand in the $3^{rd}$ panel of FIG. 13), which in turn further binds the primer-sequence of the capture/primer-probe (blue region of capture/primer-probe of FIG. 13) to initiate LACES chain elongation in the presence of the polymerase within the nucleic acid-chain elongation mixture.

In certain embodiments of the invention methods, the capture-probes, capture/primer probes or primer-probes used herein can include a spacer sequence in the probe before the beginning of the portion of the probe that functions to capture the respective target-nucleic acid (shown as red region of capture-probes in FIGS. 13-16). In particular embodiments, the spacer sequence is bound directly to the electrode and provides oligonucleotide spacing between the electrode and the beginning of the capture sequence (shown as red region of capture-probes in FIGS. 13-16). As used herein, the phrase "spacer sequence" refers to an oligonucleotide sequence of any length within any probe described herein. In particular embodiments, the spacer sequence of the probes is bound to the electrodes.

DIAL+TEEM

In particular embodiments, the invention methods can be integrated with dielectrophoresis technologies without additional fabrication processes, e.g., thus allowing low cost integrated solutions including sample handling, purification and preparation steps. For example, the applied electric fields can initially be used to isolate and concentrate total nucleic acids by dielectrophoretic techniques; after which the invention TEEM methods are employed to enrich or isolate the desired target-nucleic acid.

Accordingly, also provided herein are methods for enriching or isolating a target-nucleic acid from a mammalian-cell sample, said method comprising:

a. receiving an electrolytic fluid including ions and a mammalian-cell sample in a fluid chamber having a first and second electrode;

b. lysing the cells to form a cell-lysate;

c. applying an asymmetric di-electric field to the solution containing the cell-lysate, wherein total-nucleic acid from the cell-lysate sample is captured by at least one electrode (e.g., the first electrode);
d. washing the uncaptured cell-lysate from the fluid chamber;
e. resuspending the total-nucleic acid into the electrolytic fluid solution including ions in the fluid chamber, wherein at least one electrode has attached thereto a plurality of capture-probes complementary to the target-nucleic acid, wherein the capture probes are at the electrode-solution interface;
f. applying an annealing-voltage to the electrolytic fluid in proximity to the electrode-solution interface to generate an annealing-pH level by the electrode-solution interface, wherein the annealing-pH level causes annealing of any number of complementary base pairs between the total-nucleic acid and the capture-probes;
g. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and
h. modulating the annealing-voltage and denaturing-voltage, wherein after the final application of the corresponding pH level (e.g., annealing or denaturing), the target-nucleic acid is enriched or isolated from the total-nucleic acid by remaining bound to the capture/primer-probe on the electrode.

DIAL+TEEM

Also provided herein are methods for enriching or isolating a target-nucleic acid from a cell-lysate sample, said method comprising:
a. receiving an electrolytic fluid solution including ions and a cell-lysate sample in a fluid chamber having a first and second electrode;
b. applying an asymmetric di-electric field to the solution containing the cell lysate sample, wherein total-nucleic acid from the cell-lysate sample is captured by at least one electrode (e.g., the first electrode);
c. washing the uncaptured cell-lysate from the fluid chamber;
d. resuspending the total-nucleic acid into the electrolytic fluid solution including ions in the fluid chamber, wherein at least one electrode has attached thereto a plurality of capture-probes complementary to the target-nucleic acid, wherein the capture probes are at the electrode-solution interface;
e. applying an annealing-voltage to the electrolytic fluid in proximity to the electrode-solution interface to generate an annealing-pH level by the electrode-solution interface, wherein the annealing-pH level causes annealing of any number of complementary base pairs between the total-nucleic acid and the capture-probes;
f. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and
g. modulating the annealing-voltage and denaturing-voltage, wherein after the final application of the corresponding pH level (e.g., annealing or denaturing), the target-nucleic acid is enriched or isolated by remaining bound to the capture/primer-probe on the electrode.

In particular embodiments, the total-nucleic acid is resuspended into the fluid chamber by terminating the asymmetric di-electric field. In certain embodiments, the cell-lysate is obtained by lysing a mammalian cell-sample within the fluid chamber. In particular embodiments, the target-nucleic acid is detected by a method selected from the group consisting of LACES, direct detection, PCR, rolling circle amplification, combinations of ligation and PCR, and amplification followed by a detection step, labelled probes, intercalating fluorescent dye, and the like as further set forth herein. In particular embodiments, the material not bound to the capture/primer-probe from the nucleic acid-containing sample is washed away prior to detection. In a particular embodiment, the target-nucleic acid is detected by the LACES method. The mammalian cell-sample is obtained from cells, saliva, urine, blood, hair, semen, saliva, bone, tissue, teeth, cell-lysates, viruses, cellular nucleic acid or genomic nucleic acid.

As used herein, the phrase "mammalian-cell sample" refers to cells contained in, or obtained from, any source in any form. For example, cells can be within tissue, saliva, urine, blood, hair, semen, saliva, bone, teeth, and the like.

As used herein, the phrase "lysing the cells to form a cell-lysate" refers to the well-known process of breaking down of the cell by, for example, detergent, viral, enzymatic, or osmotic mechanisms, and the like, that compromise its integrity. A fluid containing the contents of lysed cells is referred to as a "cell-lysate" and is understood do also contain the nucleic acid contents from any viruses that have been degraded. Cell lysis is used herein to break open cells to avoid shear forces that could otherwise denature DNA.

As used herein, the phrase "total-nucleic acid from the cell-lysate sample" refers to substantially all of the nucleic acid within the particular sample being collected or analyzed from whatever source within the sample, including cells (e.g., cellular DNA), viral particles (e.g., viral nucleic acid) and/or bodily fluids (e.g., blood, serum, urine and the like).

As used herein, the phrase "washing the uncaptured cell-lysate from the fluid chamber" refers to washing the non-nucleic acid portion of the cell-lysate, which is not bound or captured by the electrode, from the fluid chamber.

As used herein, the phrase "resuspending the total-nucleic acid" refers to the well-known process of permitting captured molecules, in this case nucleic acids within the sample, to reenter the solution by discontinuing the conditions that caused their capture.

Figure 17:
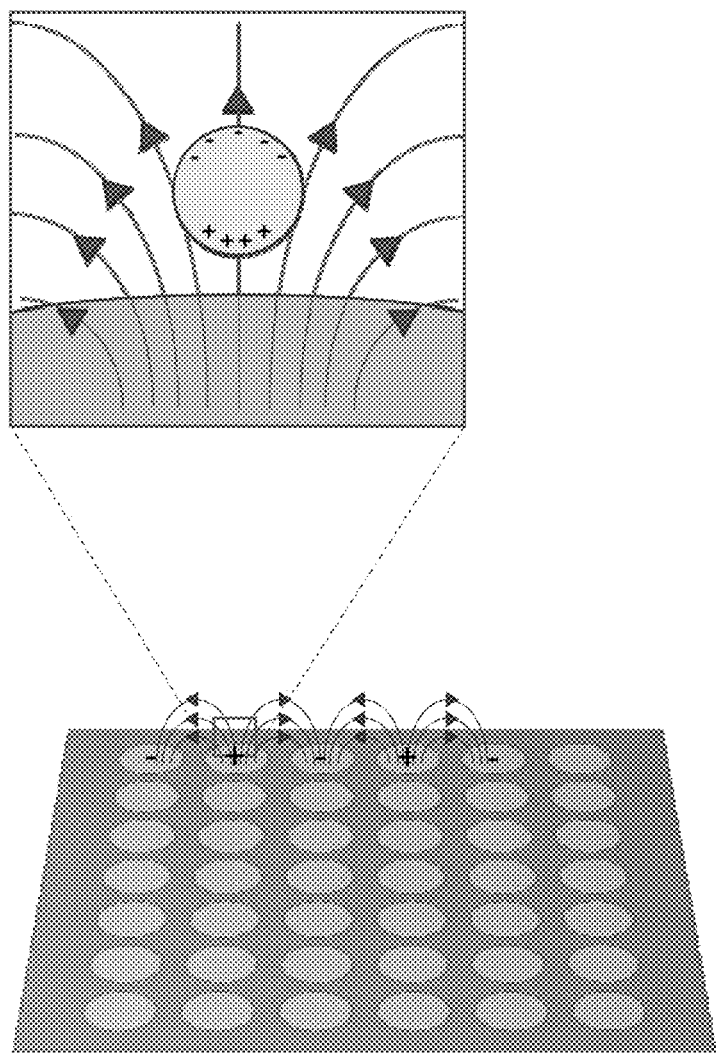
FIG. 17 shows the Dielectric forces that occur at respective locations on an exemplary microfluidic chip for the Dielectric Isolation of Nucleic Acids from Lysate (referred to herein as DIAL the process).

As used herein, the phrase "asymmetric dielectric field" or "dielectrophoretic force," or grammatical variations thereof, is the force that acts on a polarizable particle in a nonuniform AC electrical field (FIG. 17). As used herein "dielectrophoresis" is the movement of moieties in response to dielectric forces. Dielectrophoresis (DEP) is a contact-free manipulation technique applicable to biological macromolecules and microscale nanoparticles based on the induced motion of polar or polarizable particles in a nonuniform electric field. DEP generates a force on macromolecules, which depends on the frequency of the applied field and on the difference between the polarization properties of the particle and the surrounding medium (FIG. 17).

In accordance with the present invention, Dielectric Insolation of Nucleic Acids from Lysate (referred to herein as DIAL) is used to isolate nucleic acids that contain viral RNA as well as DNA from other cells in the sample from all the other components of the sample. In the DIAL process used herein, the collected sample from subjects are mixed with a chemical lysis buffer. After the initial chemical lysis process, the solution contains cell lysates and other blood components (lipids, proteins, small molecules etc.) together with viral RNA and other nucleic acids (DNA, RNA) released into the solution from cells. DIAL is used to isolate all nucleic acids (RNA and DNA) depending on distinct physical properties of nucleic acids from all the other components in the sample.

In accordance with the invention methods, the DIAL process utilizes the exact same chip design that is used for the entire DeTaiL process, including the invention TEEM and LACES methods. Thus, an advantage of the invention methods and devices (e.g., oligonucleotide chips and/or arrays) is that all 3 processes can be conducted in the same microfluidic device and/or fluid chamber, which permits rapid point of care analysis once the sample is obtained and/or entered into the device.

There are generally two types of dielectrophoresis, positive dielectorphoresis and negative dielectrophoresis. In positive dielectrophoresis, particles are moved by dielectrophoresis toward the strong field regions. In negative dielectrophoresis, particles are moved by dielectrophoresis toward weak field regions. Whether moieties exhibit positive or negative dielectrophoresis depends on whether particles are more or less polarizable than the surrounding medium.

"Dielectric properties" of a moiety are properties that determine, at least in part, the response of a moiety to a dielectric field. The dielectric properties of a moiety include the effective electric conductivity of a moiety and the effective electric permittivity of a moiety. For a particle of homogeneous composition, for example, a polystyrene bead, the effective conductivity and effective permittivity are independent of the frequency of the electric field. For moieties of nonhomogeneous composition, for a example, a cell or cell-lysate, the effective conductivity and effective permittivity are values that take into account the effective conductivities and effective permittivities of both the surface (membrane) and internal portion of the cell including its cellular-nucleic acid, and can vary with the frequency of the electric field. In addition, the dielectric force experience by a moiety in an electric field is dependent on its size; therefore, the overall size of moiety is herein considered to be a dielectric property of a moiety. Properties of a moiety that contribute to its dielectric properties include the net charge on a moiety; the composition of a moiety (including the distribution of chemical groups or moieties on, within, or throughout a moiety); size of a moiety; surface configuration of a moiety; surface charge of a moiety; and the conformation of a moiety.

As used herein, "traveling wave dielectrophoresis" is the movement of moieties in response to a traveling wave electric field. The phrase "traveling-wave dielectrophoretic (DEP) force" refers to the force that is generated on particles or molecules due to a traveling-wave electric field. An ideal traveling-wave field is characterized by the distribution of the phase values of AC electric field components, being a linear function of the position of the particle. A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quadrature signals (0, 90, 180 and 270 degrees) to energize four linear, parallel electrodes patterned on the chip surfaces. Such four electrodes may be used to form a basic, repeating unit. Depending on the applications, there may be more than two such units that are located next to each other. This will produce a traveling electric field in the spaces above or near the electrodes. As long as electrode elements are arranged following certain spatially sequential orders well-known in the art, applying phase-sequenced signals will result in establishing traveling electrical fields in the region close to the electrodes.

DIAL+TEEM+LACES

Also provided herein, is a comprehensive "DeTaiL" method of utilizing DIAL along with invention TEEM and LACES methods starting from a mammalian-cell sample. For example, provided herein are methods for enriching or isolating a target-nucleic acid from a mammalian-cell sample, said method comprising:
  a. receiving an electrolytic fluid including ions and a mammalian-cell sample in a fluid chamber having a first and second electrode;
  b. lysing the cells to form a cell-lysate;
  c. applying an asymmetric di-electric field to the solution containing the cell-lysate, wherein total-nucleic acid from the cell-lysate sample is captured by at least one electrode (e.g., the first electrode);
  d. washing the uncaptured cell-lysate from the fluid chamber;
  e. resuspending the total-nucleic acid into the electrolytic fluid solution including ions in the fluid chamber, wherein at least one electrode has attached thereto a plurality of capture-probes complementary to the target-nucleic acid, wherein the capture probes are at the electrode-solution interface;
  f. applying an annealing-voltage to the electrolytic fluid in proximity to the electrode-solution interface to generate an annealing-pH level by the electrode-solution interface, wherein the annealing-pH level causes annealing of any number of complementary base pairs between the total-nucleic acid and the capture-probes;
  g. applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes and target-nucleic acids, that are either a particular number of base pairs shorter or a particular range of base pairs shorter than the full-length of a double-stranded capture-probe; and
  h. modulating the annealing-voltage and denaturing-voltage, wherein after the final application of the corresponding pH level (e.g., annealing or denaturing), the target-nucleic acid is enriched or isolated from the total-nucleic acid by remaining bound to the capture/primer-probe on the electrode (e.g., the first electrode), wherein the bound target-nucleic acid is a template strand for template directed elongation synthesis;
  i. providing an elongation mixture comprising (i) a polymerase enzyme, (ii) an ATP regenerating enzyme, (iii) a luminescence enzyme (e.g., firefly luciferase), and (iv) a polymerase-ATP regenerating enzyme-luminescence reagent solution having the components for carrying out template directed elongation synthesis of a growing nucleic acid strand, wherein said reagent solution includes an ATP-regenerating-enzyme-substrate, a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;

j. carrying out nucleic acid elongation synthesis such that one or a plurality of nucleotide analogs are added sequentially to the template strand if the capture/primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme yielding ATP, then c) binding the ATP to a luminescence-enzyme, wherein a luminescence-substrate is catalyzed by the luminescence-enzyme to produce luminescence while regenerating the respective leaving group; and k. detecting light from the luminescence while nucleic acid synthesis is occurring, whereby detection of light indicates the presence of the particular target nucleic acid sequence.

In a particular embodiment, material not bound to the capture/primer-probe from the total-nucleic acid is washed away prior to providing an elongation reaction mixture of step (1).

Microfluidic Chips & Devices

Also provided herein is a portable instrument-based diagnostic system for detection of pathogens (e., SARS-CoV-2 virus, and the like) that integrates each of the invention DeTaiL processes provided herein within the device (e.g., DIAL, TEEM and LACES) and produces rapid Point of Care results from the time of sample collection. In particular embodiments, the rapid Point of Care results occur in less than a time selected from 30, 25, 20, 25, 20, 15, 10, 5 mins. In a particular embodiment, the rapid results occur in less than 5 minutes. The invention platform incorporates the invention LACE and TEEM methods provide herein with currently available components to produce a robust and elegant combination of sample preparation, enrichment, a robust breakthrough signal amplification assay; along with a user-friendly portable device with low system complexity that achieves comparable results with gold standard clinical and central laboratory findings.

Using the invention electronic modulation (TEEM) and signal amplification based luminescence detection technology (LACE) provided herein, the invention device and/or system is capable of detecting nucleic acid, such as for example viral RNA, to produce gold standard specificity and sensitivity performance. The invention device utilizes single-use cartridges (see FIG. 20) that includes all the needed reagents within and, importantly, has a sealed reservoir for waste that prevents cross contamination and directly processes human nucleic acid-containing samples, such as current standard nasopharyngeal swabs as well as oropharyngeal and nasal swabs, and the like, without any further operator involvement once the consumable single-use cartridge is inserted into the system.

The invention system and device platform offers the following advantages over current mainstream methods:

Integrated, single-chamber cascade sample purification, target enrichment, signal amplification-based luminescence detection reaction, Rapid sample preparation and enrichment by electronic modulation and signal amplification based luminescence detection, and All in an enclosed system that requires minimal need for contamination control.

Accordingly, in particular embodiments, provided herein are invention single-use-cartridge device instruments (e.g., a single-use-cartridge shown in FIG. 20) for use employing the invention methods to detect target-nucleic acid, comprising: (i) a fluidics system for storing and transferring sample, detection and processing reagents, e.g. probes, wash solutions, and the like, to an array; (ii) a reaction fluid chamber, or flow cell, holding or comprising an array and having flow-through and electric potential (voltage) control capability; and (iii) an illumination and detection system (e.g., a single-use-cartridge in combination with portable device shown in FIG. 20). In one embodiment, a fluid chamber or flow cell has a voltage control subsystem with ability to modulate voltage.

As used herein, a "single-use cartridge" is a microfluidic structure that contains the components and reagents to carry out the invention TEEM and LACES methods therein; and thus permit the presence or absence of the target-nucleic acid being interrogated. The single-use cartridge can be any chip, dfluidic chip, chip device, substrate, or array described herein, and the like.

Also provided herein are fluidic chip devices for carrying out the invention methods that can be compatible with standard sample preparation and detection platforms for nucleic acid chain elongation. In one embodiment, the fluidic chip device can contain a reservoir or fluid chamber having at least a first metal electrode thereon. Different heights (e.g., distance between the electrodes) and geometries of the electrodes can be used for maximum efficiency and engineering of the diffuse layer and electric double layer. The fluidic chip device can be electrically interfaced with an electrical signal source (e.g., function generator), which can be included in such standard platforms, to provide the applied voltage at the electrodes.

The chip device can be operated to implement the modulation of charge for the invention TEEM methods. For example, for denaturation, low pH and/or high pH can be generated, e.g., based on the electrode configurations and/or applied electrical signal on the electrodes. For example, for annealing and denaturation, different pH levels can be generated. Different chamber heights can be configured in the fluid chamber to affect the rate at which the target-nucleic acids can be enriched or isolated from the sample. The device can include an inlet and outlet port or region. Capture-probes and Capture/Primer-probe oligonucleotides can be attached to an electrode surface while the reaction solution can be kept stationary while the applied voltages to the electrodes are modulated.

In another embodiment, a fluidic chip device for carrying out the invention chain elongation detection methods includes a substrate that is electrically insulating having a channel, or a plurality of channels, structured to carry the electrolytic fluid, e.g., including continuous or intermittent flow rates.

In other embodiments, suitable chips in a system of the present invention include active chips. More particularly, at least one chip in an integrated biochip system of the present invention is an active chip. Active chips are chips that comprise micro-scale structures that can generate a physical force when energy is supplied to them from, for example, from a power supply. Thus, the applied physical forces used in the methods of the present invention require an energy source (sometimes called a "signal source"), e.g., a voltage or the like, and a structure capable of converting the energy to a type of force useful in the present invention. Active chips are therefore described as chips that supply at least in part, a source of a physical force used in the methods of the present invention. Micro-scale structures that can convert the applied energy to a type of force useful in the present invention can be, as nonlimiting examples, electrodes for generating electrophoretic and dielectrophoretic forces, electromagnetic units for generating electromagnetic or magnetophoretic or magnetic forces, and piezoelectric transducers for generating acoustic forces. Depending on the type of microscale structure they comprise, they can be referred to as, for example, electrophoresis or dielectrophoresis chips (comprising electrodes), electromagnetic chips (comprising electromagnetic units) or acoustic chips (comprising piezoelectric transducers). Chips can also comprise optical elements, micro-capillaries or tips, heating elements (e.g., metal wires), Peltier elements, micro-valves, or micro-pumps.

An active chip can be constructed by building physical force elements (e.g., electromagnetic units, piezoelectric transducers, or electrodes) onto or into the chip surface, or by applying functional layers such as, for example, oligonucleotide arrays or protein arrays onto the surface of the chip to make, for example, a passive chip; or combination of both. Other materials that can be provided on passive or active chips of the present invention include specific binding members, including, but not limited to nucleic acid molecules; enzymes, catalysts, or substrates (including, but not limited to enzymes, catalysts, and substrates used for detection); reagents, including insulating layers, or coatings or layers of substances provided to prevent nonspecific binding or interaction of one or more sample components to a chip surface; complexes; and even viruses and cells. These materials can optionally be provided in wells or channels of a chip of a system of the present invention. Materials that can be used as coatings or layers to prevent nonspecific or undesirable interactions of one or more sample components with a chip surface (including micro-scale structures on the chip) can form a "top layer" of the chip, and can be thin (less than 100 Angstrom) layers of polymers, compounds such as silicon dioxide, surfactants, or biomolecules, such as BSA.

Examples of active chips include, but are not limited to, the dielectrophoresis electrode array on a glass substrate (e.g., Dielectrophoretic Manipulation of Particles by Wang et al., in IEEE Transaction on Industry Applications, Vol. 33, No. 3, May/June, 1997, pages 660-669"), the individually addressable electrode array on a microfabricated bioelectronic chip (e.g., Preparation and Hybridization Analysis of DNA/RNA from *E. coli* on Microfabricated Bioelectronic Chips by Cheng et al., Nature Biotechnology, Vol. 16, 1998, pages 541-546), the capillary electrophoresis chip (e.g., Combination of Sample-Preconcentration and Capillary Electrophoresis On-Chip by Lichtenberg, et al., in Micro Total Analysis Systems 2000 edited by A. van den Berg et al., pages 307-310), the acoustic force chips disclosed in U.S. Pat. No. 6,029,518; each of which are incorporated herein by reference in their entirety for all purposes.

For dielectrophoresis chips, including chips that are used for conventional and traveling wave dielectrophoresis, electrodes on a chip can be of any shape, such as rectangular, castellated, triangular, circular, and the like. Electrodes can be arranged in various patterns, for example, spiral, parallel, interdigitated, polynomial, etc. Electrode arrays can be fabricated on a chip by methods known in the art, for example, electroplating, sputtering, photolithography or etching. Examples of a chip comprising electrodes include, but are not limited to, the dielectrophoresis electrode array on a glass substrate (e.g., Dielectrophoretic Manipulation of Particles by Wang et al., in IEEE Transaction on Industry Applications, Vol. 33, No. 3, May/June, 1997, pages 660-669), individually addressable electrode array on a microfabricated bioelectronic chip (e.g., Preparation and Hybridization Analysis of DNA/RNA from *E. coli* on Microfabricated Bioelectronic Chips by Cheng et al., Nature Biotechnology, Vol. 16, 1998, pages 541-546), and the capillary electrophoresis chip (e.g., Combination of Sample-Preconcentration and Capillary Electrophoresis On-Chip by Lichtenberg, et al, in Micro Total Analysis Systems 2000 edited by A. van den Berg et al., pages 307-310).

In one embodiment of the present invention, an integrated biochip system comprises a single chip. In this aspect, a single-chip integrated biochip system comprises an active chip that can perform at least two sequential tasks (e.g., at least TEEM and LACES or at least DIAL and TEEM; or DIAL, TEEM and LACES). Preferably, an active chip of a single-chip system comprises different functional elements to perform at least two sequential tasks, e.g., di-electrophoresis and modulating electric fields, and the like. A chip that performs more than one function can have combinations of one or more different functional elements such as, for example, specific binding members, substrates, reagents, or different types of micro-scale structures, including micro-scale structures that provide, at least in part, one or more sources of physical forces used in processes or tasks carried out on the chip. In embodiments where a system of the present invention comprises a chip that has different functional elements, the regions of the chip having different functional elements can be in close proximity, such that sample components are freely and readily diffusible among the different functional elements. In other embodiments, the different functional elements are at least partially interspersed with one another. Alternatively, in a multiple force chip, different functional elements, in particular different physical force-generating elements, can be provided in different structurally linked substrates that are vertically oriented with respect to one another.

Kits of the Invention

In the commercialization of the methods described herein, certain kits for construction of capture-probe and/or capture/primer-prober arrays of the invention and for using the same for various applications are particularly useful. In general, kits of the invention can include any oligonucleotide/probe arrays as described herein and/or the reagents and molecules for creating and/or using such capture-probe-arrays or chips to carry out the invention methods provided herein.

In one embodiment, kits for constructing capture-probe arrays of the invention include, but are not limited to, a support having a surface with capture-probe oligonucleotides attached, the capture-probes having a recognition sequence for a particular target-nucleic acid being interrogated (e.g., a SARS-COV2 sequence). Such kits may further include reagents for conducting a chain elongation reaction with such target-nucleic acids. Such reagents include polymerases, reverse transcriptases (FIG. 15, $3^{rd}$ panel), dNTPs, primers, buffers, and the like.

Kits for applications of target-nucleic-acid-detection-arrays of the invention include, but are not limited to, kits for determining the presence of the target-nucleotide sequence, and the like. A kit typically comprises at least one support having a surface and one or more reagents necessary or useful for constructing a capture-probe array of the invention or for carrying out an the invention LACES or TEEM methods therewith. Such reagents include, without limitation, nucleic acid primers, probes, adaptors, enzymes (e.g., polymerases), and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In particular embodiments of such kits, the surface may be a planar surface having an array of discrete regions. The discrete regions may have capture probes attached and the adaptors may each have a region complementary to the capture oligonucleotides such that the concatemers are capable of being attached to the discrete regions by formation of complexes between the capture oligonucleotides and the complementary regions of the adaptor oligonucleotides.

EXAMPLES

Example 1—Luminescence-Based Target Nucleic Acid Detection

Once released from an incorporated dNTP, the pyrophosphate (PPi) interacts with ATP sulfurylase, which binds the pyrophosphate to adenosine 5'-phosphosulfate (APS) yielding ATP (FIGS. 1B and 1C).

The ATP (ATP) produced above is used to bind to Firefly luciferase that uses luciferin as a substrate (FIG. 1C). With the ATP (ATP) acting as a cofactor, Firefly luciferase catalyzes luciferin (FIG. 1C; and FIG. 2, FIG. 3 and FIG. 10). As a result of the enzymatic catalysis, luciferin is converted into oxyluciferin and luminescence is also produced (FIG. 1C). As side products of the reaction, adenosine monophosphate and PPi are generated. This results in a detectable luminescence emission during the discreet and limited period of the luminescence (FIG. 1C). Accordingly, as a result of dNTP interacting with the DNA polymerase, luminescent light is generated upon luminescence produced by the luminescence reaction produced by the luminescence-enzyme and luminescence-substrate. The respective luminescent light is the detected prior to the light vanishing.

This dNTP incorporation process is repeated until the target nucleic acid sequence is detected and/or the desired nucleic acid nucleic acid chain elongation-length has been achieved.

Example 2—Parameters Affecting Luminescence Generation

Figure 4:
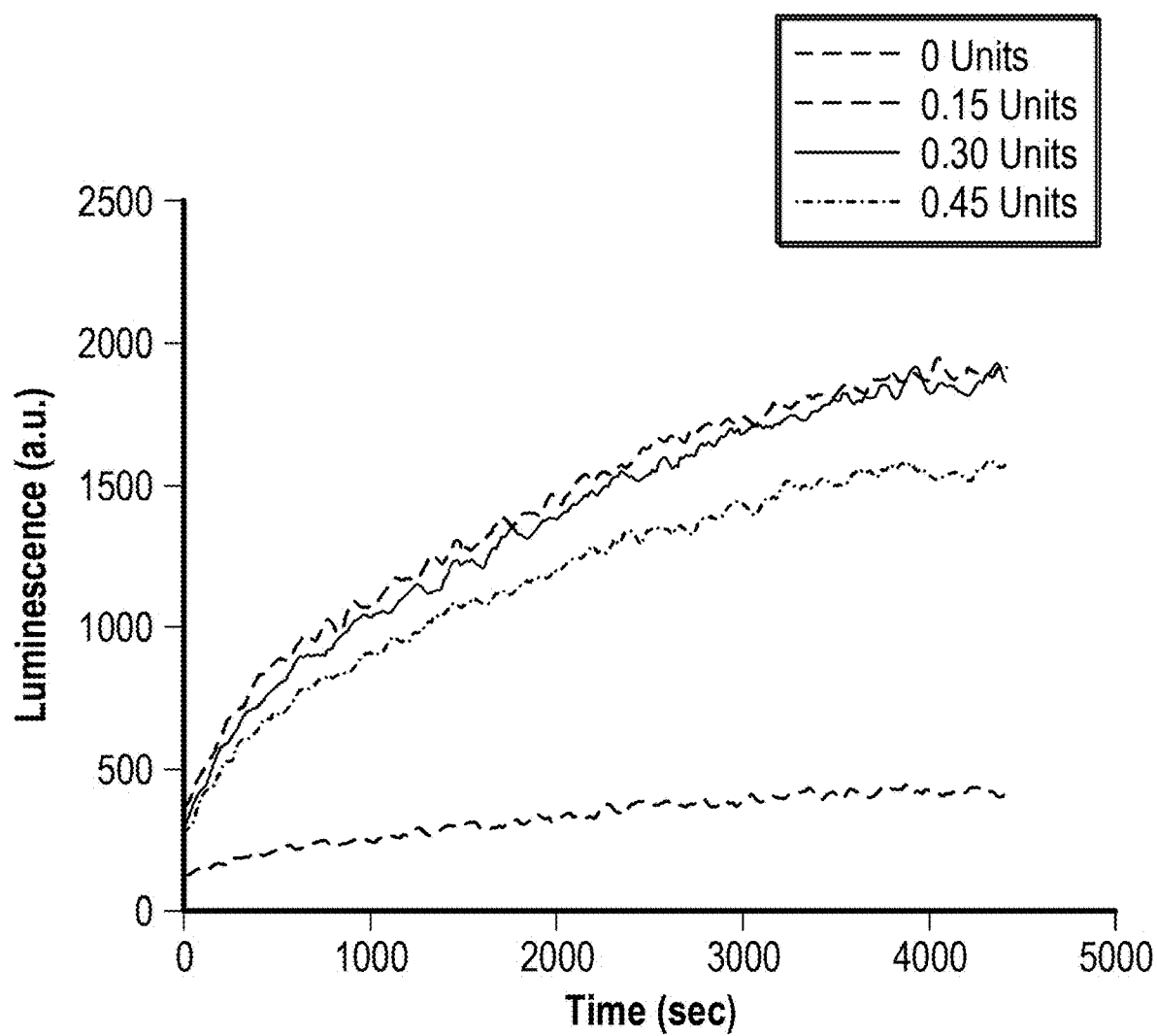
FIG. 4 shows Luminescence Generation as a Result of the invention LACES Reaction with Varying ATP Sulfurylase.
Figure 5:
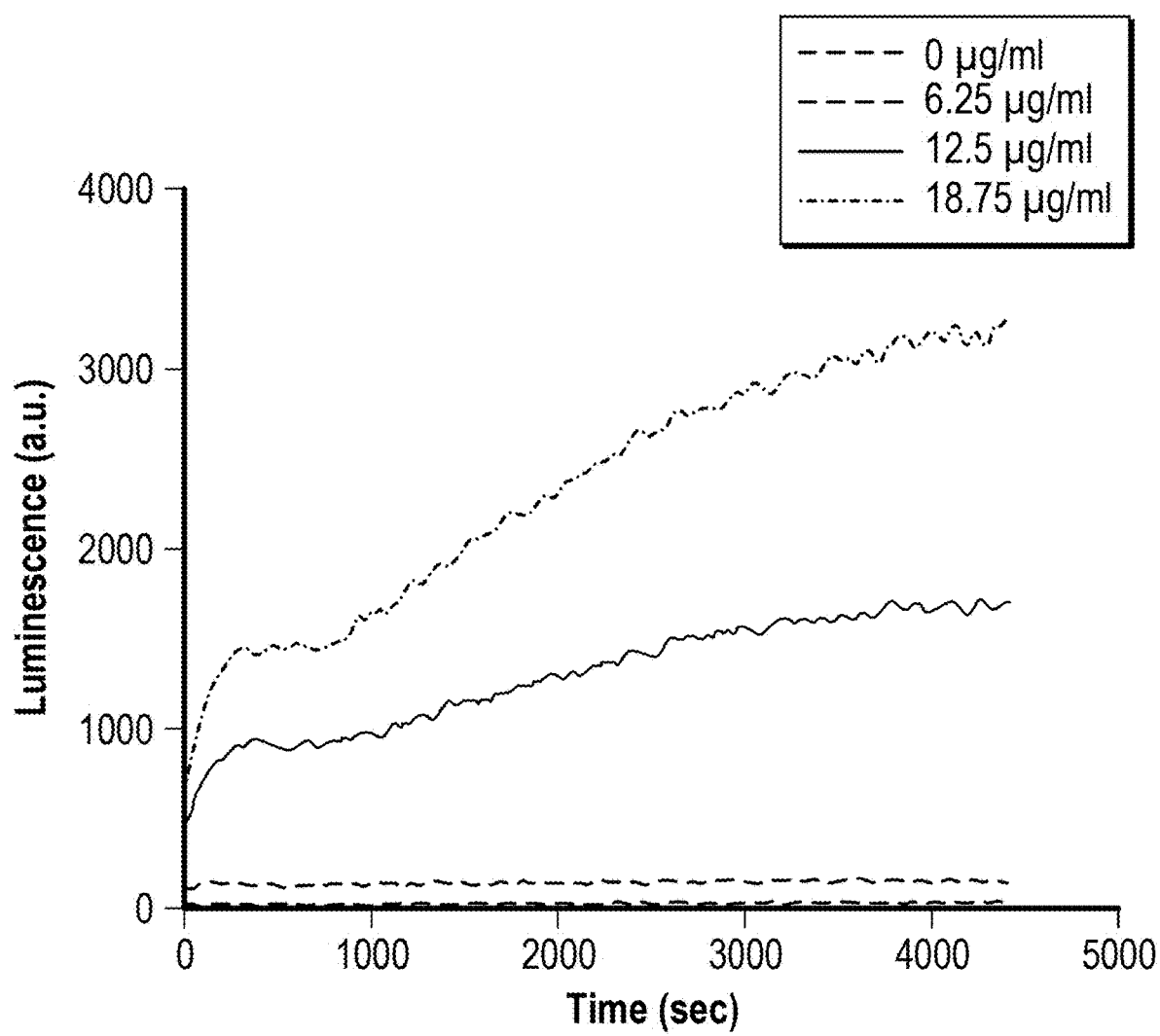
FIG. 5 shows Luminescence Generation as a Result of the invention LACES Reaction with Varying Firefly Luciferase.
Figure 6:
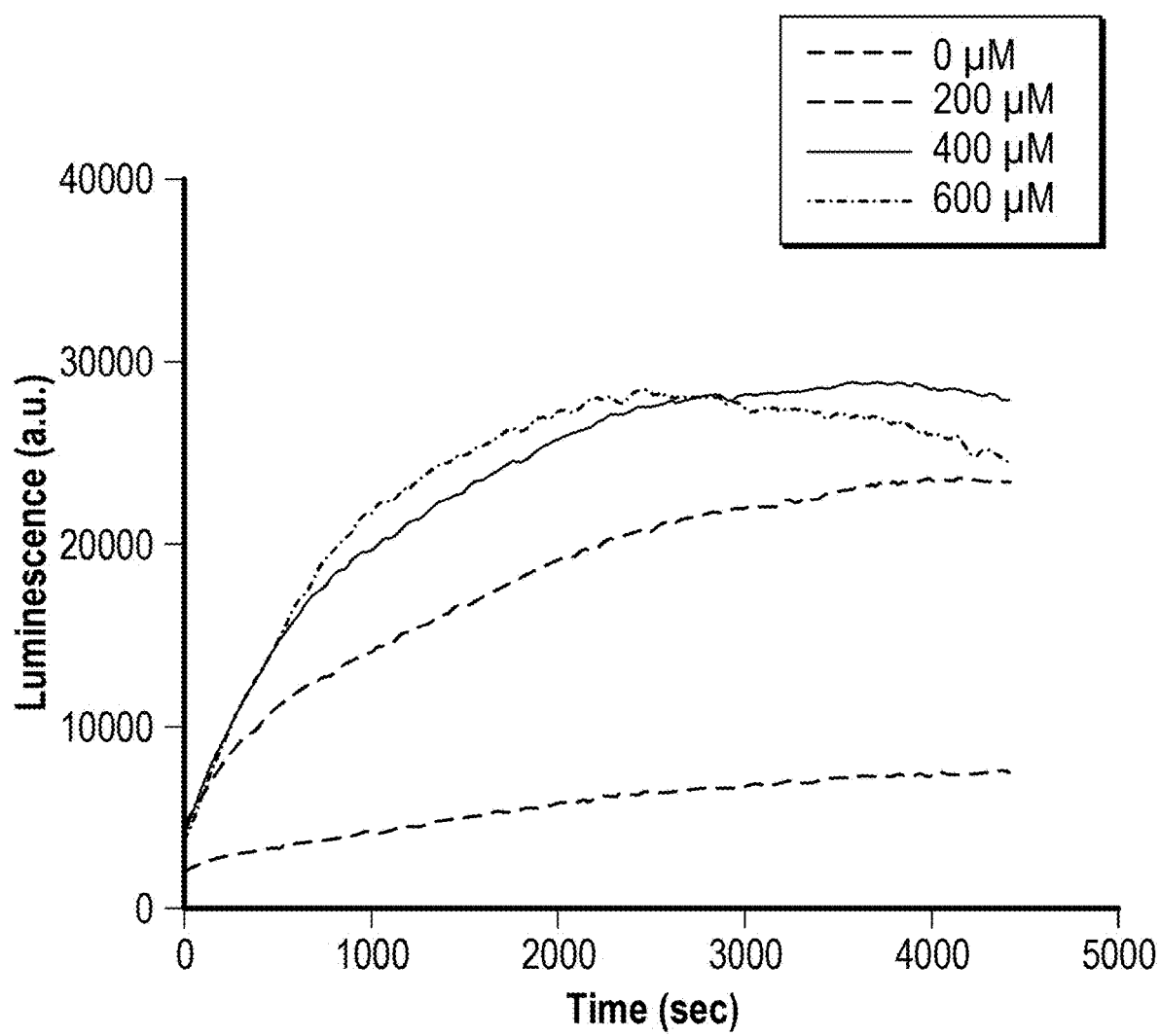
FIG. 6 shows Luminescence Generation as a Result of the invention LACES Reaction with Varying dGTP-Coumarin.

Example 2A—Effects of Varying the Respective Concentrations of ATP Sulfurylase, Firefly Luciferase, and the Luminescence-Substrate—dGTP-Coumarin In this reaction, a 300 bp single-stranded DNA template was produced made up of all cytosine bases except for the start sequence of a 20 bp region formed by a mixture of 4 bases (dATP, dGTP, dTTP, dCTP). In addition to the template DNA, the reaction contained primer oligonucleotides complementary to the start sequence, dGTP-Coumarin, ATP Sulfurylase, Adenosine 5'-phosphosulfate, Firefly luciferase (as the luminescence-enzyme), and luciferin (as the luminescence-substrate). The effects of varying the respective concentrations of ATP Sulfurylase, Firefly luciferase, and the luminescence-substrate, dGTP-Coumarin are shown in FIGS. 4-6, respectively. As can be seen in FIGS. 4-6, starting with dGTP-Coumarin (which is a dGTP labeled by Coumarin at the terminal phosphate), this concatenated three-enzyme system of Polymerase-ATP Sulfurylase-Firefly luciferase utilized herein was found to generate luminescence in a final step.

Example 2B—Effects of Adding ATP Sulfurylase and APS to a Luciferase Reaction The following reagents of the sequence mixture were used in this experiment:

| 10x TAE Buffer 17.5 uL | | |
|---|---|---|
| Luciferase (5 mg/ml in 1M Tris) (1:50) 17.5 uL | 250 ng | Sigma |
| Cyc-Luc(10 mg/mL) (1:10 in 1xTAE) 35 uL | 5 ug | EMD Millipore |
| ATP (100 mM) (1:5k) 35 uL | 1.2 uM | Sigma |
| CoA (10 mM) (1:20) 35 uL | 2 mM | Sigma |
| MgCl2 (10 mM) = (2.5 uL per rxn) | 1 mM | NEB |
| PPase 1x(=no dil) (200 U/mL) = 0.5 uL | 0.1 U | Sigma |
| ASulf (300 U/mL) = 0.5 uL | 0.15 U | NEB |
| APS (10 mM) = 1 uL | 377 uM | Sigma |

In order to study the effect of the ATP sulfurylase/luciferase signal amplification loop on the fluorescent signal level, one can observe the ATPSulfurylase-Luciferase couple alone. The reactions were performed in 1×TAE Buffer with 750 ng of Luciferase, 5 µg of Cyc-Luc luciferin, 1.2 µM of ATP, 2 mM of Coenzyme A, 1 mM MgCl2 0.15 units of ATP Sulfurylase, 377 µM of APS. The variation of pyrophosphatase corresponds to 0.1, 0.005 and 0.002 unit amounts. The Luciferase, ATP, Coenzyme A, Pyrophosphatase and APS were obtained from Sigma. The ATP Sulfurylase and MgCl2 were obtained from NEB.

Initially Pyrophosphatase and MgCl2 were dispensed into the relevant wells in a 384-well microplate. Then a mastermix of buffer, Luciferase and Coenzyme A was prepared, mixed and dispensed into the relevant wells in equal amounts. Then Cyc-Luc luciferin was added to each well and finally ATP was added to each well. The plate was then shaken for 15 seconds before measurements were taken from a FLUOstar Optima plate reader.

Figure 7:
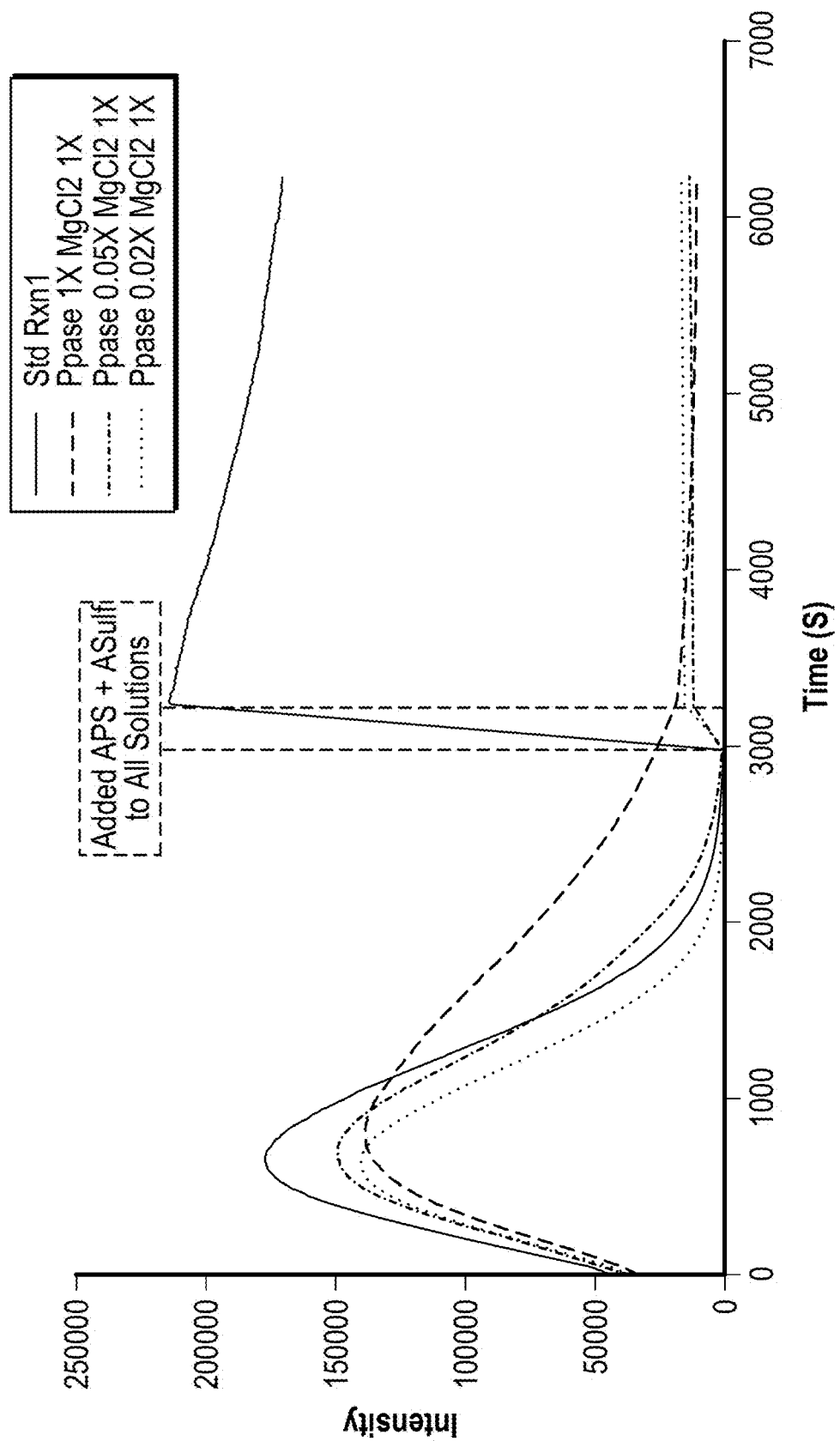
FIG. 7 shows the results of adding ATP and APS to a Luciferase reaction with varying amounts of inorganic pyrophosphatase.

In this example, a standard reaction corresponding to a luciferase reaction alone using and luciferin as substrates is shown as the solid line plot in FIG. 7. In FIG. 7, the solid line plot shows a rise and decay of luminescence signal as expected from a regular luciferase reaction. At time 3000 s, ATP-Sulfurylase and APS was added to the standard reaction, which as can be seen in FIG. 7, started the ATP Sulfurylase/Luciferase Signal Amplification Loop and caused amplification of the signal (see FIG. 7, solid line plot starting at 3000s). These results indicate that the luminescence signal generated by the invention nucleic acid target sequence detection methods can be amplified by the addition of an ATP regenerating enzyme (ATP Sulfurylase in this example) and its cognate ATP regenerating enzyme substrate (APS in this example), which initiates an ATP Sulfurylase/Luciferase Signal Amplification Loop.

Three other reactions similar to the standard reaction were carried out, where varying relative dilutions of inorganic pyrophosphate were added in the amounts of 0.02× (1:50 dilution), 0.05× (1:20 dilution) and 1× (no dilution) of pyrophosphatase 1×, along with 1× of MgCl2. As seen in FIG. 7, the loop signal is diminished with addition of inorganic pyrophosphatase (0.02× Ppase dotted plot and 0.05× Ppase dashed plot). In higher concentrations of inorganic pyrophosphatase, the loop is completely diminished (1× Ppase dashed plot). This indicates that the level of luminescence signal amplified by the ATP Sulfurylase/Luciferase Signal Amplification Loop results from the continuous and repeated generation of PPi, which can be abolished by pyrophosphatase.

Example 2C—Effect of Adding Coenzyme a to the ATP Sulfurylase/Luciferase Signal Amplification Loop Reaction on Luminescence Signal The effect of adding Coenzyme A to the ATP sulfurylase/luciferase signal amplification loop on the luminescent signal level was studied by running a standard luciferase reaction as in Example 2B. The reactions were performed in 1×TAE Buffer with 750 ng of Luciferase, 5 µg of Cyc-Luc luciferin, 1.2 µM of ATP, 2 mM of Coenzyme A, 1 mM MgCl2 0.15 units of ATP Sulfurylase, 200 µM of APS. The Luciferase, ATP, Coenzyme A, and APS were obtained from Sigma. The ATP Sulfurylase and MgCl2 were obtained from NEB. Initially ATP Sulfurylase, APS, Coenzyme A and MgCl2 were dispensed into the relevant wells in a 384-well microplate. Then a mastermix of buffer, Luciferase and Cyc-Luc luciferin was prepared, mixed and dispensed into the relevant wells in equal amounts. Then ATP was added to each well. The plate was then shaken for 15 seconds before measurements were taken from a FLUOstar Optima plate reader.

Figure 8:
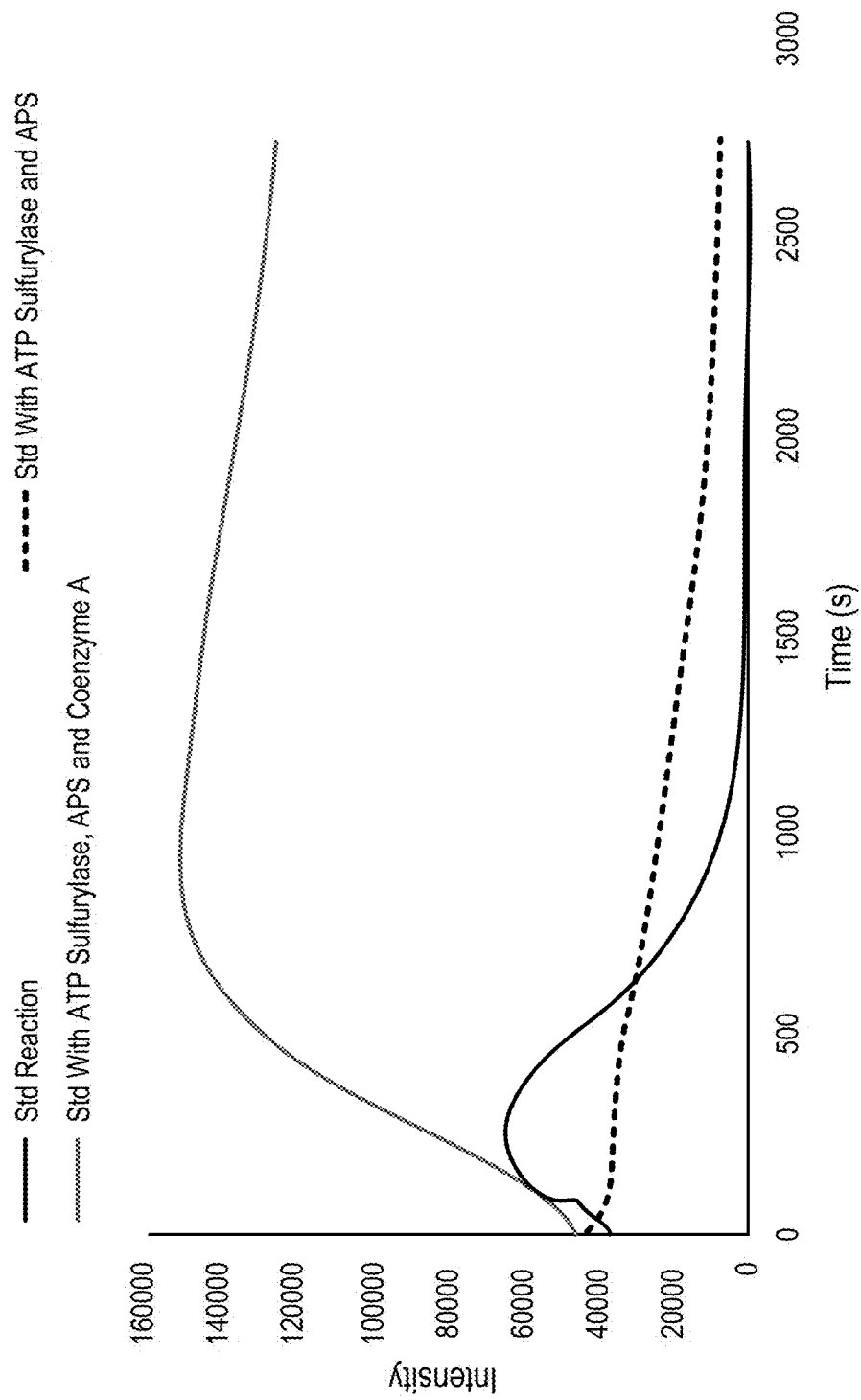
FIG. 8 shows the effect of Adding Coenzyme A to the ATP Sulfurylase/Luciferase Signal Amplification Loop Reaction on Luminescence Signal.

The results of the luminescence emission of standard luciferase reaction, which contains Luciferase, Luciferin and ATP, are shown in the dark solid line plot of FIG. 8. In FIG. 8, the dark solid line plot shows a rise and decay of luminescent signal as expected from a regular luciferase reaction. The dashed line plot show the luciferase reaction with ATP Sulfurylase and APS. The light line plot of FIG. 8 shows the case for the luciferase-ATP Sulfurylase concatenate together with APS and Coenzyme A. In this example of APS and Coenzyme co-administration, the luminescence signal level is much higher and signal is more durable. These results indicate that Coenzyme A, has a positive effect on the signal, which is believed to occur by preventing damage to the luciferase and stabilizing the luciferase/luciferin couple thereby improving the loop efficiency.

While the present embodiments have been particularly shown and described with reference to example embodiments herein, it will be understood by those of ordinary skill in the art that various changes in form and details may be made therein without departing from the spirit and scope of the present embodiments as defined by the following claims. Those skilled in the art will recognize, or be able to ascertain using no more than routine experimentation, numerous equivalents to the specific procedures described herein. Such equivalents are considered to be within the scope of the present invention and are covered by the following claims. The contents of all non-patent literature publications, patents, and patent applications cited throughout this application are hereby incorporated by reference in their entirety for all purposes. The appropriate components, processes, and methods of those patents, applications and other documents may be selected for the present invention and embodiments thereof.

What is claimed is:

1. A method for enriching or isolating a target-nucleic acid from a nucleic acid-containing sample, said method comprising:
    a) receiving an electrolytic fluid solution including ions and a nucleic acid-containing sample in a fluid chamber having a first and second electrode, wherein at least one electrode has attached thereto a plurality of capture-probes or capture/primer probes complementary to the target-nucleic acid, wherein the capture probes are at the electrode-solution interface;
    b) applying an annealing-voltage to the electrolytic fluid in proximity to the electrode-solution interface to generate an annealing-pH level by the interface, wherein the annealing-pH level causes annealing of any number of complementary base pairs between nucleic acid within the nucleic acid-containing sample and the capture-probes or capture/primer probes;
    c) applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture probes or capture/primer probes and target-nucleic acids, that are either a particular number of base pairs shorter or a particular range of base pairs shorter than the full-length of a double-stranded capture-probe or capture/primer probe; and
    d) modulating voltages between the annealing-voltage and denaturing-voltage, wherein multiple cycles of modulation are performed on the entire nucleic acid-containing sample while it is inside the fluid chamber, wherein after the final application of the corresponding pH level, the target-nucleic acid is enriched or isolated from the nucleic acid-containing sample by remaining bound to the capture-probes or capture/primer probes on the at least one electrode, wherein the modulating voltages between the annealing-voltage and denaturing-voltage is at a modulation frequency in the range of 0.1-1000 Khz.

2. The method of claim 1, wherein the target-nucleic acid is SARS-COV2.

3. The method of claim 1, wherein the target-nucleic acid is detected by a method selected from the group consisting of: LACES, direct detection, PCR, rolling circle amplification, combinations of ligation and PCR, and amplification followed by a detection step, labelled probes, and intercalating fluorescent dye.

4. The method of claim 3, wherein material not bound to the capture-probe from the nucleic acid-containing sample is washed away prior to detection.

5. The method of claim 1,
    wherein the pH level is generated via migration of ions in solution;
    wherein the density of capture-probes on the electrode is 100 to 1,000,000 oligonucleotide probes per cm2; and
    wherein the nucleic acid-containing sample is selected from cells, saliva, urine, blood, hair, semen, saliva, bone, tissue, teeth, cell-lysates, viruses, cellular nucleic acid or genomic nucleic acid.

6. The method of claim 1, wherein the nucleic acid-containing sample is obtained by dielectrophoresis of a cell-lysate.

7. The method of claim 1, wherein the number of complementary base pairs denatured during the modulating step is selected from a range of 1-20 base pair double-strands for capture-probes or capture/primer probes that are about 20 oligonucleotides or longer; or 1-15, 1-10, or 1-5 base pair double-strands for capture-probes or capture/primer probes that are about 20 oligonucleotides or shorter.

8. A method for detecting the presence of a target-nucleic acid sequence in a nucleic acid-containing sample comprising:

a) receiving an electrolytic fluid solution including ions and a nucleic acid-containing sample in a fluid chamber having a first and second electrode, wherein at least one electrode has attached thereto a plurality of capture/primer-probes complementary to the target-nucleic acid, wherein the capture/primer-probes are at the electrode-solution interface;

b) applying an annealing-voltage to the electrolytic fluid in proximity to the electrode-solution interface to generate an annealing-pH level by the interface, wherein the annealing-pH level causes annealing of any number of complementary base pairs between nucleic acid within the nucleic acid-containing sample and the capture/primer-probes;

c) applying a denaturing-voltage to the electrolytic fluid in proximity to the electrode-solution interface to generate a denaturing-pH level by the interface, wherein the denaturing-pH level causes the denaturation of double-stranded nucleic acids, including hybridized pairs of capture/primer-probes and target-nucleic acids, that are either a particular number of base pairs shorter or a particular range of base pairs shorter than the full-length of a double-stranded capture-probe; and d) modulating the annealing-voltage and denaturing-voltage, wherein multiple cycles of modulation are performed on the entire nucleic acid-containing sample while it is inside the fluid chamber, and wherein after the final application of the corresponding pH level, the target-nucleic acid is enriched or isolated from the nucleic acid-containing sample by remaining bound to the capture/primer-probe on the at least one electrode, wherein the bound target-nucleic acid is a template strand for template directed elongation synthesis, wherein the modulating voltages between the annealing-voltage and denaturing-voltage is at a modulation frequency in the range of 0.1-1000 Khz;

e) providing an elongation mixture comprising (i) a polymerase enzyme, (ii) an ATP regenerating enzyme, (iii) a luminescence enzyme, and (iv) a polymerase-ATP regenerating enzyme-luminescence reagent solution having the components for carrying out template directed elongation synthesis of a growing nucleic acid strand, wherein said reagent solution includes an ATP-regenerating-enzyme-substrate, a luminescence-substrate; and a plurality of types of dNTPs or nucleotide analogs, wherein each type of nucleotide analog has a leaving group that is cleavable by the polymerase, wherein the leaving group is cleaved upon polymerase-dependent binding of a respective nucleotide analog to the template strand;

f) carrying out nucleic acid elongation synthesis such that one or a plurality of nucleotide analogs are added sequentially to the template strand if the capture/primer-probe hybridizes to the target nucleic acid sequence, whereby: a) a nucleotide analog associates with the polymerase, b) the nucleotide analog is incorporated on the template strand by the polymerase when the leaving group on that nucleotide analog is cleaved by the polymerase, wherein the leaving group is combined with an ATP-regenerating-enzyme-substrate by the ATP regenerating enzyme yielding ATP, then c) binding the ATP to a luminescence-enzyme, wherein a luminescence-substrate is catalyzed by the luminescence-enzyme to produce luminescence while regenerating the respective leaving group; and g) detecting light from the luminescence while nucleic acid synthesis is occurring, whereby detection of light indicates the presence of the particular target nucleic acid sequence.

9. The method of claim 8, wherein the target-nucleic acid is SARS-COV2.

10. The method of claim 8, wherein material not bound to the capture/primer-probe from the nucleic acid-containing sample is washed away prior to providing an elongation reaction mixture of step (e).

11. The method of claim 8, wherein the leaving group is a pyrophosphate,
wherein the luminescence-enzyme is firefly luciferase,
wherein the luminescence-substrate is luciferin, reverse transcriptase, and
wherein the polymerase enzyme is selected from DNA polymerase, RNA polymerase or
wherein the ATP regenerating enzyme is selected from ATP Sulfurylase, AGPPase, and PPDK.

12. The method of claim 8, wherein the ATP-regenerating-enzyme-substrate is selected from APS, ADP-glucose, and AMP+PEP.

13. The method of claim 8, wherein the leaving group is combined with APS by ATP Sulfurylase; with ADP-glucose by AGPPase; or with AMP+PEP by PPDK.

14. The method of claim 8, wherein types of nucleotide analogs comprise dATP, dTTP, dGTP, dCTP, dUTP, dGTPαS, dCTPαS, dTTPαS and dATPαS.

15. The method of claim 8, wherein the capture/primer-probes have a length in nucleotide bases selected from the group consisting of: 20-100, 20-90, 20-80, 20-70, 20-60, 20-50, 20-40, 20-30, 5-100, 10-100, 30-100, 40-100, 50-100, 60-100, 70-100, 80-100, 90-100, 15-150, 10-200, 5-300, 20-200, 20-300, 20-400, 20-500, 20-600, 20-700, 20-800, 20-900, 20-1000, at least 5, at least 10, at least 15, at least 20, at least 30, at least 40, at least 50, at least 60, at least 70, at least 80, at least 90, at least 100, at least 150, at least 200, at least 300, at least 400, at least 500, at least 600, at least 700, at least 800, at least 900 at least 1000 nucleotide bases.

16. The method of claim 8, further comprising adding Coenzyme A to the polymerase-ATP regenerating enzyme-luminescence reagent solution, in a ratio of Coenzyme A to luciferase effective to increase the intensity of signal of an ATP regenerating enzyme/luciferase amplification loop.

17. The method of claim 8, wherein a plurality of polymerase enzymes are used.

18. The method of claim 8, wherein the nucleic acid-containing sample is obtained by dielectrophoresis of a cell-lysate.

19. The method of claim 8, wherein the number of complementary base pairs denatured during the modulating step is selected from a range of 1-20 base pair double-strands for capture-probes or capture/primer probes that are about 20 oligonucleotides or longer; or 1-15, 1-10, or 1-5 base pair double-strands for capture-probes or capture/primer probes that are about 20 oligonucleotides or shorter.

* * * * *